US008729113B2

(12) United States Patent
Galley et al.

(10) Patent No.: US 8,729,113 B2
(45) Date of Patent: *May 20, 2014

(54) 4,5-DIHYDRO-OXAZOL-2YL DERIVATIVES

(75) Inventors: Guido Galley, Rheinfelden (DE);
Annick Goergler, Colmar (FR); Katrin Groebke Zbinden, Liestal (CH); Roger Norcross, Olsberg (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/033,645

(22) Filed: Feb. 24, 2011

(65) Prior Publication Data

US 2011/0144333 A1 Jun. 16, 2011

Related U.S. Application Data

(63) Continuation of application No. 12/558,772, filed on Sep. 14, 2009, which is a continuation-in-part of application No. 12/504,702, filed on Jul. 17, 2009, now abandoned.

(30) Foreign Application Priority Data

Jul. 24, 2008 (EP) .................................. 08161060

(51) Int. Cl.
*A61K 31/421* (2006.01)
*C07D 263/08* (2006.01)

(52) U.S. Cl.
USPC ............ 514/377; 548/215; 548/233; 514/374

(58) Field of Classification Search
USPC .......................... 548/215, 233; 514/374, 377
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Specter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Eble | |
| 3,577,428 A | 5/1971 | Suh et al. | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,311,840 A | 1/1982 | Condon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 6,268,389 B1 | 7/2001 | Esser et al. | |
| 7,834,044 B2 | 11/2010 | Galley et al. | |
| 7,858,652 B2 | 12/2010 | Galley et al. | |
| 7,858,653 B2 | 12/2010 | Galley et al. | |
| 7,875,645 B2 | 1/2011 | Galley et al. | |
| 7,902,238 B2 * | 3/2011 | Galley et al. .................. 514/374 |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |

(Continued)

FOREIGN PATENT DOCUMENTS

| | | |
|---|---|---|
| CA | 2246027 | 2/2000 |
| DE | 842 065 | 6/1952 |

(Continued)

OTHER PUBLICATIONS

Deutch et al , (1999) Neurotransmitters. In Fundamental Neuroscience (2nd ed.) pp. 193-234, Academic Press.

(Continued)

*Primary Examiner* — Golam M M Shameem
(74) *Attorney, Agent, or Firm* — George W. Johnston; Patricia S. Rocha-Tramaloni; Kimberly J. Prior

(57) ABSTRACT

The invention relates to compounds of formula I wherein
$R^1$, $R^2$, X, Y, and n are defined in the specification and to pharmaceutically acceptable acid addition salts thereof. The invention also provides pharmaceutical compositions and methods of manufacture of such compounds. The compounds are useful for the treatment of diseases related to the biological function of the trace amine associated receptors, which diseases are depression, anxiety disorders, bipolar disorder, attention deficit hyperactivity disorder, stress-related disorders, psychotic disorders, schizophrenia, neurological diseases, Parkinson's disease, neurodegenerative disorders, Alzheimer's disease, epilepsy, migraine, substance abuse and metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

22 Claims, No Drawings

(56) References Cited

U.S. PATENT DOCUMENTS

| | | | |
|---|---|---|---|
| 2007/0197620 | A1 | 8/2007 | Galley et al. |
| 2007/0197622 | A1 | 8/2007 | Galley et al. |
| 2008/0096906 | A1 | 4/2008 | Galley et al. |
| 2008/0119535 | A1 | 5/2008 | Galley et al. |

FOREIGN PATENT DOCUMENTS

| | | |
|---|---|---|
| DE | 1795517 | 2/1972 |
| DE | 2203373 | 8/1972 |
| DE | 2253555 | 11/1972 |
| DE | 2446758 | 4/1976 |
| DE | 2849537 | 5/1980 |
| EP | 0024829 | 3/1981 |
| EP | 096297 | 12/1983 |
| EP | 0125410 | 11/1984 |
| EP | 0166937 | 1/1986 |
| EP | 0167459 | 1/1986 |
| EP | 0331374 | 9/1989 |
| EP | 0424059 | 4/1991 |
| EP | 0717037 | 6/1996 |
| EP | 0857483 | 8/1998 |
| EP | 0924209 | 6/1999 |
| EP | 1103243 | 5/2001 |
| EP | 1413576 | 4/2004 |
| ES | 323985 | 12/1966 |
| FR | 1355049 | 3/1964 |
| FR | 6551 | 12/1968 |
| GB | 877306 | 9/1961 |
| GB | 1016514 | 1/1996 |
| WO | 199622768 | 8/1996 |
| WO | 9712874 | 4/1997 |
| WO | 9812183 | 3/1998 |
| WO | 0130762 | 5/2001 |
| WO | 0181334 | 11/2001 |
| WO | 200222801 | 3/2002 |
| WO | 200240453 | 5/2002 |
| WO | 02076950 | 10/2002 |
| WO | 03092374 | 11/2003 |
| WO | 2004014898 | 2/2004 |
| WO | 2006119411 | 11/2006 |
| WO | 2007024944 | 3/2007 |
| WO | 2007085556 | 8/2007 |
| WO | 2008/071574 | 6/2008 |
| WO | 2008092785 | 8/2008 |

OTHER PUBLICATIONS

Wong, et al., (2001) Nat Rev. Neurosci. 2, pp. 343-351.
Carlsson et al. (2001) Annu. Rev. Pharmacol. Toxicol. 41, pp. 237-260.
Tuite et al. (2003) Expert Opin. Investig. Drugs 12, pp. 1335-1352.
Castellanos et al., (2002) Nat. Rev. Neurosci. 3, pp. 617-628.
Usdin, E. and Sandler. M.; Editors. Psychopharmacology Series, vol. 1: Trace Amines and the Brain. [Proceedings of a Study Group at the 14th Annual Meeting of the American College of Neuropsychoparmacology, San Juan, Puerto Rico] (1976) pp. 1-281.
Lindemann et al., (2005) Trends in Pharmacol. Sci. 26, pp. 274-281.
Branchek et al., (2003) Curr. Opin. Pharmaccl. 3, pp. 90-97.
Premont et al. (2001) Proc. Natl. Acad. Sci. U. S. A. 98, pp. 9474-9475.
Mosseau et al,, (1995) Prog. Brain Res, 106, pp. 285-291.
McCormack et al (1986) J. Neurosci. 6, pp. 94-101.
Dyck, L.E. (1989) Life Sci. 44, pp. 1149-1156.
Parker et al., (1988) J. Pharmacol. Exp. Ther. 245, pp. 109-210.
Lindemann et al. (2005) Genomics 85, pp. 372-385.
Habib et al., Synthesis, 1984, pp. 825-827.
Trani et al., J. Heterocycl. Chem. 11, pp. 257-262 (1974).
Bunzow, J.R., et al,, Molecular Pharmacology, vol. 60(6), pp. 1181-1188 (2001), XP008008060.
Holt, Andrew, J. of Psychiatry & Neuroscience, vol. 28(6), pp. 409-414 (2003), XP002438693.
Timmermans, P B M W M, et al., Life Sciences, vol. 28, No. 6, pp. 653-660 (1981), XP002442517.
Prisinzano, Thomas, et al., Bioorganic & Medicinal Chemistry Letters, vol. 14, No. 18, pp. 4697-4699 (2004), XP002442518.
Olmos, G., et al., European Journal of Pharmacology, vol, 262, No. ½, pp. 41-48 (1994), XP000567119.
McLennan, P.L., European Journal of Pharmacology, vol. 69, No. 4, pp. 477-482 (1981), XP002442519.
Nathanson, J.A., Molecular Pharmacology, vol. 28., No. 3, pp, 254-268 (1985), XP009085722.
Hirashima, et al., Bioorganic and Medicinal Chemistry, vol. 10, No. 1, pp. 117-123 (2002), XP002442520.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Melloni et al., Eur. J. Med. Chem. vol. 26, pp. 207-213 (1991).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol, 39, pp. 2937-2940 (1998).
Nakamura et al., J. Chem. Soc. Perkin Trans. 1, pp. 1061-1066 (2002).
Yoshiya, et al., J. of Medicinal Chemistry, vol. 35(4), pp. 750-755 (1992), XP002151512.
Faust, J.A., et al., J. of Organic Chemistry, vol. 26, pp. 4044-4047 (1961), XP002442336.
Savola, J.M., et al., Drug Research, vol. 38(1), pp. 29-35 (1988), XP002033085.
Cordi et al., Journal of Med Chem., 44(50) pp. 787-805 (2001).
Matsunaga, et al., Bioorganic & Medicinal Chemistry, p. 4314-4336 (2004), XP002444990.
Matsunaga, et al., Tetrahedron: Asymmetry, Elsevier Science Publishers, vol. 5, No. 13, pp. 2021-2028 (2004), XP004520137.
Ojida, A., et al., Tetrahedron: Asymmetry, Elsevier Science Publishers, vol. 15, No, 10, pp. 1555-1559 (2004), XP004508431.
Zhang, et al., Journal of Medicinal Chemistry, vol. 40, pp. 3014-3024 (1997), XP002108693.
Ojida et al., Org. Lett, 2002, 4, pp. 3051-3054 (Supporting document attached).
Khimiya Geterotsiklicheskikh Soedinenii, 1988, pp. 77-79 (English language abstract attached).
RE1MANN et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Debernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at α—Adrenoceptors, J. Med. Chem. (1987), 30:1011-1017.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing α1A-Adrenoceptor Agonist, J. Med. Chem. (2004), 47:3220-3235.
Carroll et al., In Vitro and In Vivo Characterization of Alpha-1A Selective Agonists and Their Utility For Stress Incontinence, Med. Chem. Res. (2004), 13:134-148.
Jetter et al., Synthesis of 4-Substituted Imidazoles via Palladium-Catalyzed Cross-Coupling Reactions, Synthesis (1998), 829-831.

(56) References Cited

OTHER PUBLICATIONS

Bagley et al., Synthesis and α2-Adrenegeric Activities of Imidazole and Imidazolidine Analogues: In Vitro and In Vivo Selectivity, Medicinal Chemistry Research (1994), 4:346-364.
Lee et al., 4-[(N-Imidazol-2-ylmethyl)aniline]pyranopyridine Analogs as Novel Anti-Angiogenic Agents, Bull. Korean Chem. Soc. (2005), 25: 619-628.
Agami et al., Tetrahedron 2001, vol. 57(1) pp. 195-200.
Ueda et al., Bioorganic & Medicinal Chem. Letters 2004, vol. 14(2) pp. 313-316.
Ma et al., Synlett (2006) vol. 8 pp. 1181-1184.
Juaristi et al., Tetrahedron Asymmetry (1999)vol. 10 pp. 2441-2495.
Davis et al., Heterocycles (2002) vol. 58 pp. 251-258.
Vassiliou et al, Synlett (2003) pp. 2398-2400.
Schollkopf, U., Topics Curr. Chem (1983), vol. 109, pp. 65-84.
Dandanpani et al., Journal of Organic Chemistry (2005) vol. 70(23) p. 9447.
Takahata et al., J. Org. Chem. (2003) vol. 68 p. 3603.
Turner, et al., J. Org. Chem. (1991), 56, pp. 5739-5740.
Costa Rican Opposition Notice dated May 19, 2011.
(Translation of Taiwanese Off Act in Corres Taiwan App 098124766 Jan. 27, 2012).
Kohn, H. et al., Tetrahedron Letters 37(18):3195-3201 (1981).
(New Zealand Examination Report in Corres Appl 589292 Sep. 4, 2012).
Von Rohrscheidt, C et al., Tetrahedron Letters 3:215-218 (1979).
Jarry, C. et al., "Synthesis and Structural Study of 5-alkyloxymethyl-2-amino-delta-2-oxazolines" Annales Pharmaceutiques Francaises (Translation attached), 43(2):183-188 (1985).
Matga, M et al., Journal of Chromatography 984(2):253-260 (2003).
Lima et al., Current Med Chem 12(1):23-49 (2005).
(English Translation of Columbian Off Act in Corres Col App 10148408 Nov. 6, 2012).

\* cited by examiner

4,5-DIHYDRO-OXAZOL-2YL DERIVATIVES

PRIORITY TO RELATED APPLICATION(S)

This application is a continuation of U.S. application Ser. No. 12/558,772, filed Sep. 14, 2009, now pending; which is a continuation-in-part of U.S. application Ser. No. 12/504,702, filed Jul. 17, 2009, now pending; which claims the benefit of European Patent Application No. 08161060.2, filed Jul. 24, 2008. The entire contents of the above-identified applications are hereby incorporated by reference.

BACKGROUND OF THE INVENTION

2-Aminooxazolines are described in the literature as hypertensive agents with good affinity to the adrenergic receptor or as intermediates in processes for preparation of pharmaceutical active agents, for example in EP 0 167 459, U.S. Pat. No. 4,311,840, DE 2,253, 555, Tetrahedron (2001), 57(1), 195-200 or in Bioorganic and Medicinal Chemistry Letters (2004), 14(2), 313-316.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1—4) highly conserved between human and rodents. TAs activate TAAR1 via Gas. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

References Used:
1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;
2 Wong, M. L. and Licinio, J. (2001) Research and treatment approaches to depression. *Nat. Rev. Neurosci.* 2, 343-351;
3 Carlsson, A. et al. (2001) Interactions between monoamines, glutamate, and GABA in schizophrenia: new evidence. *Annu. Rev. Pharmacol. Toxicol.* 41, 237-260;
4 Tuite, P. and Riss, J. (2003) Recent developments in the pharmacological treatment of Parkinson's disease. *Expert Opin. Investig. Drugs* 12, 1335-1352,
5 Castellanos, F. X. and Tannock, R. (2002) Neuroscience of attention-deficit/hyperactivity disorder: the search for endophenotypes. *Nat. Rev. Neurosci.* 3, 617-628;
6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychoparmacology*, San Juan, Puerto Rico] (1976);
7 Lindemann, L. and Hoener, M. (2005) A renaissance in trace amines inspired by a novel GPCR family. *Trends in Pharmacol. Sci.* 26, 274-281;
8 Branchek, T. A. and Blackburn, T. P. (2003) Trace amine receptors as targets for novel therapeutics: legend, myth and fact. *Curr. Opin. Pharmacol.* 3, 90-97;
9 Premont, R. T. et al. (2001) Following the trace of elusive amines. *Proc. Natl. Acad. Sci. U.S.A.* 98, 9474-9475;
10 Mousseau, D. D. and Butterworth, R. F. (1995) A high-affinity [3H] tryptamine binding site in human brain. *Prog. Brain Res.* 106, 285-291;
11 McCormack, J. K. et al. (1986) Autoradiographic localization of tryptamine binding sites in the rat and dog central nervous system. *J. Neurosci.* 6, 94-101;
12 Dyck, L. E. (1989) Release of some endogenous trace amines from rat striatal slices in the presence and absence of a monoamine oxidase inhibitor. *Life Sci.* 44, 1149-1156;
13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14 Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides compounds of formula I

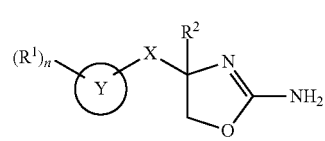

wherein

R$^1$ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;

X is —O—(CH$_2$)$_2$—, —O—CHR"—CH$_2$—, —O—CH$_2$—CHR', —O—CR"$_2$—CH$_2$—, —(CH$_2$)$_2$—CHR', —CHR'—(CH$_2$)$_2$—, —CR"$_2$—(CH$_2$)$_2$—, —CH$_2$—CHR"—CH$_2$—, —CH$_2$—CR"$_2$—CH$_2$—, —CHR"—O—CH$_2$—, —CH$_2$—O—CH$_2$—, —CR"$_2$—O—CH$_2$—, —CF$_2$(CH$_2$)$_2$—, —CR"$_2$—CH$_2$—, —SiR"$_2$—(CH$_2$)$_2$—, —S—(CH$_2$)$_2$—, —S(O)$_2$—(CH$_2$)$_2$—, —(CH$_2$)$_4$—, —CH$_2$—O—(CH$_2$)$_2$—,

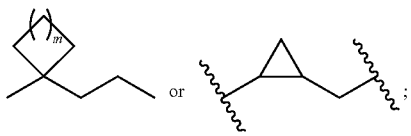

wherein m is 0, 1, 2 or 3;

R' is lower alkyl, lower alkoxy or lower alkyl substituted by halogen;

R" is lower alkyl or lower alkyl substituted by halogen;

R$^2$ is hydrogen or lower alkyl;

Y is aryl, cycloalkyl or heteroaryl; and n is 1, 2 or 3;

or to a pharmaceutically suitable acid addition salt.

The invention includes all racemic mixtures, all their corresponding enantiomers and/or optical isomers.

In addition, all tautomeric forms of compounds of formula I are also encompassed by the present invention.

The invention also provides pharmaceutical compositions that comprise a compound of formula I or a pharmaceutically acceptable salt thereof and a pharmaceutically acceptable carrier. The invention further provides methods for the manufacture of the compounds and compositions of the invention.

Compounds of formula I have a good affinity to the trace amine associated receptors (TAARs), especially for TAAR1. Compounds of the present invention have selectivity for TAAR1 receptor over adrenergic receptors, in particular good selectivity vs the human and rat alpha1 and alpha2 adrenergic receptors.

The compounds disclosed in the present formula I can be used for the treatment of diseases related to the biological function of the trace amine associated receptors, which diseases are depression, anxiety disorders, bipolar disorder, attention deficit hyperactivity disorder, stress-related disorders, psychotic disorders, schizophrenia, neurological diseases, Parkinson's disease, neurodegenerative disorders, Alzheimer's disease, epilepsy, migraine, hypertension, substance abuse and metabolic disorders, such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, diabetes and attention deficit hyperactivity disorder (ADHD).

DETAILED DESCRIPTION OF THE INVENTION

As used herein, the term "lower alkyl" denotes a saturated straight-or branchedhydrocarbon chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl residue as defined above which is attached via an oxygen atom.

As used herein, the term "lower alkyl substituted by halogen" denotes an alkyl group as defined above, wherein at least one hydrogen atom is replaced by halogen, for example CF$_3$, CHF$_2$, CH$_2$F, CH$_2$CF$_3$, CH$_2$CH$_2$CF$_3$, CH$_2$CF$_2$CF$_3$ and the like.

As used herein, the term "lower alkoxy substituted by halogen" denotes an alkoxy group as defined above, wherein at least one hydrogen atom is replaced by halogen, for example OCF$_3$, OCHF$_2$, OCH$_2$F, OCH$_2$CF$_3$, OCH$_2$CH$_2$CF$_3$, OCH$_2$CF$_2$CF$_3$ and the like.

The term "halogen" denotes chlorine, iodine, fluorine and bromine.

The term "cycloalkyl" is an alkylene ring, containing from 3 to 6 carbon ring atoms.

The term "aryl" denotes a monocyclic or bicyclic aromatic ring, for example phenyl or naphthyl. Preferred is phenyl.

The term "heteroaryl" denotes an aromatic one or two membered ring system, having at least one heteroatom selected from N, O, or S, for example pyridine-2-or 3-yl, pyrimidine-2-yl or quinoline-6 or 7-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following compounds are disclosed by the present invention:

A compound of formula I-1

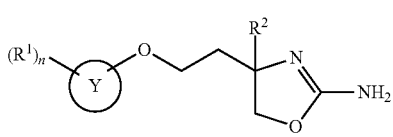

I-1 wherein

R$^1$ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;

R$^2$ is hydrogen or lower alkyl;

Y is aryl, cycloalkyl or heteroaryl; and n is 1, 2 or 3;

or a pharmaceutically suitable acid addition salt.

Preferred compounds from formula I-1 are the followings:
(S)-4-(2-phenoxy-ethyl)-4,5-dihydro-oxazol-2-ylamine;
(S)-4-[2-(4-fluoro-phenoxy)-ethyl]-4,5-dihydro-oxazol-2-ylamine;
(S)-4-[2-(4-chloro-phenoxy)-ethyl]-4,5-dihydro-oxazol-2-ylamine;
(S)-4-[2-(3-trifluoromethyl-phenoxy)-ethyl]-4,5-dihydro-oxazol-2-ylamine;
(S)-4-[2-(3-chloro-phenoxy)-ethyl]-4,5-dihydro-oxazol-2-ylamine;
(S)-4-[2-(2-chloro-phenoxy)-ethyl]-4,5-dihydro-oxazol-2-ylamine;
(S)-4-[2-(3-chloro-4-fluoro-phenoxy)-ethyl]-4,5-dihydro-oxazol-2-ylamine;
(S)-4-[2-(3,4-difluoro-phenoxy)-ethyl]-4,5-dihydro-oxazol-2-ylamine;
(S)-4-[2-(2-chloro-4-fluoro-phenoxy)-ethyl]-4,5-dihydro-oxazol-2-ylamine;
(S)-4-[2-(2,4-difluoro-phenoxy)-ethyl]-4,5-dihydro-oxazol-2-ylamine;
(S)-4-[2-(3-trifluoromethoxy-phenoxy)-ethyl]-4,5-dihydro-oxazol-2-ylamine;
(S)-4-[2-(3-methoxy-phenoxy)-ethyl]-4,5-dihydro-oxazol-2-ylamine;
(S)-4-[2-(3-isopropyl-phenoxy)-ethyl]-4,5-dihydro-oxazol-2-ylamine;
(RS)-4-methyl-4-(2-phenoxy-ethyl)-4,5-dihydro-oxazol-2-ylamine;
(S)-4-(2-m-tolyloxy-ethyl)-4,5-dihydro-oxazol-2-ylamine;
(S)-4-[2-(biphenyl-3-yloxy)-ethyl]-4,5-dihydro-oxazol-2-ylamine;
(S)-4-[2-(3-benzyloxy-phenoxy)-ethyl]-4,5-dihydro-oxazol-2-ylamine;
(S)-4-[2-(3-bromo-phenoxy)-ethyl]-4,5-dihydro-oxazol-2-ylamine;
(S)-4-[2-(4-phenoxy-phenoxy)-ethyl]-4,5-dihydro-oxazol-2-ylamine;
(RS)-4-[2-(4-fluoro-phenoxy)-ethyl]-4-methyl-4,5-dihydro-oxazol-2-ylamine;
(RS)-4-[2-(3,4-difluoro-phenoxy)-ethyl]-4-methyl-4,5-dihydro-oxazol-2-ylamine;
(S)-4-[2-(4-benzyl-phenoxy)-ethyl]-4,5-dihydro-oxazol-2-ylamine;
(S)-4-[2-(4'-fluoro-biphenyl-4-yloxy)-ethyl]-4,5-dihydro-oxazol-2-ylamine;
(S)-4-[2-(4-chloro-3-fluoro-phenoxy)-ethyl]-4,5-dihydro-oxazol-2-ylamine;
(S)-4-[2-(4-bromo-phenoxy)-ethyl]-4,5-dihydro-oxazol-2-ylamine;
(S)-4-[2-(3,4-dichloro-phenoxy)-ethyl]-4,5-dihydro-oxazol-2-ylamine;
(S)-4-[2-(4-chloro-2-fluoro-phenoxy)-ethyl]-4,5-dihydro-oxazol-2-ylamine;
(S)-4-[2-(4-methoxy-phenoxy)-ethyl]-4,5-dihydro-oxazol-2-ylamine;
3-[2-((S)-2-amino-4,5-dihydro-oxazol-4-yl)-ethoxy]-benzonitrile;
(S)-4-[2-(4-trifluoromethyl-phenoxy)-ethyl]-4,5-dihydro-oxazol-2-ylamine;
3-[2-((S)-2-amino-4,5-dihydro-oxazol-4-yl)-ethoxy]-benzoic acid methyl ester;
(S)-4-[2-(3,5-difluoro-phenoxy)-ethyl]-4,5-dihydro-oxazol-2-ylamine; and
3-[2-((S)-2-amino-4,5-dihydro-oxazol-4-yl)-ethoxy]-benzoic acid benzyl ester.

A compound of formula I-2,

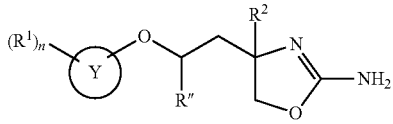

wherein
$R^1$ is hydrogen, lower alkyl, lower alkoxy, lower alkyl substituted by halogen, lower alkoxy substituted by halogen, halogen, cyano, nitro, hydroxy, C(O)O-lower alkyl, $S(O)_2$-lower alkyl, $C(O)OCH_2$-phenyl, $OCH_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
$R^2$ is hydrogen or lower alkyl;
Y is aryl, cycloalkyl or heteroaryl; and
n is 1, 2 or 3;
or a pharmaceutically suitable acid addition salt.
Preferred compounds of formula I-2 are
(4S)-4-(2-phenoxy-propyl)-4,5-dihydro-oxazol-2-ylamine;
(4S)-4-[2-(4-chloro-phenoxy)-propyl]-4,5-dihydro-oxazol-2-ylamine;
(4S)-4-(2-m-tolyloxy-propyl)-4,5-dihydro-oxazol-2-ylamine;
(S)-4-[(S)-2-(4-chloro-phenoxy)-propyl]-4,5-dihydro-oxazol-2-ylamine;
((S)-4-[(S)-2-(4-fluoro-phenoxy)-propyl]-4,5-dihydro-oxazol-2-ylamine;
(S)-4-[(S)-2-(3-chloro-phenoxy)-propyl]-4,5-dihydro-oxazol-2-ylamine;
(S)-4-[(S)-2-(3,4-difluoro-phenoxy)-propyl]-4,5-dihydro-oxazol-2-ylamine;
(S)-4-[(S)-2-(4-chloro-3-fluoro-phenoxy)-propyl]-4,5-dihydro-oxazol-2-ylamine;
(S)-4-[(S)-2-(4-bromo-phenoxy)-propyl]-4,5-dihydro-oxazol-2-ylamine;
(S)-4-[(S)-2-(3-chloro-4-fluoro-phenoxy)-propyl]-4,5-dihydro-oxazol-2-ylamine;
(S)-4-[(S)-2-(4-chloro-2-fluoro-phenoxy)-propyl]-4,5-dihydro-oxazol-2-ylamine;
(S)-4-[(S)-2-(2,4-difluoro-phenoxy)-propyl]-4,5-dihydro-oxazol-2-ylamine;
(S)-4-[(S)-2-(3,4-dichloro-phenoxy)-propyl]-4,5-dihydro-oxazol-2-ylamine;
3-[(S)-2-(S)-2-amino-4,5-dihydro-oxazol-4-yl)-1-methyl-ethoxy]-benzonitrile;
(S)-4-[(S)-2-(4-phenoxy-phenoxy)-propyl]-4,5-dihydro-oxazol-2-ylamine;
(S)-4-((S)-2-phenoxy-propyl)-4,5-dihydro-oxazol-2-ylamine;
(S)-4-[(R)-2-(3-chloro-phenoxy)-propyl]-4,5-dihydro-oxazol-2-ylamine;
(S)-4-[(R)-2-(3-chloro-4-fluoro-phenoxy)-propyl]-4,5-dihydro-oxazol-2-ylamine;
(S)-4-[(R)-2-(3,4-dichloro-phenoxy)-propyl]-4,5-dihydro-oxazol-2-ylamine;
(S)-4-[(S)-2-(4-chloro-phenoxy)-butyl]-4,5-dihydro-oxazol-2-ylamine;
(S)-4-((S)-2-phenoxy-butyl)-4,5-dihydro-oxazol-2-ylamine;

(S)-4-[(S)-2-(4-bromo-phenoxy)-butyl]-4,5-dihydro-oxazol-2-ylamine;

((S)-4-[(S)-2-(3-chloro-phenoxy)-butyl]-4,5-dihydro-oxazol-2-ylamine;

(S)-4-[(S)-2-(4-chloro-3-fluoro-phenoxy)-butyl]-4,5-dihydro-oxazol-2-ylamine;

(S)-4-[(S)-2-(2,4-difluoro-phenoxy)-butyl]-4,5-dihydro-oxazol-2-ylamine;

(S)-4-[(S)-2-(4-fluoro-phenoxy)-butyl]-4,5-dihydro-oxazol-2-ylamine;

(S)-4-[(S)-2-(3,4-difluoro-phenoxy)-butyl]-4,5-dihydro-oxazol-2-ylamine;

(S)-4-[(S)-2-(3-chloro-4-fluoro-phenoxy)-butyl]-4,5-dihydro-oxazol-2-ylamine;

(S)-4-[(S)-2-(4-trifluoromethyl-phenoxy)-butyl]-4,5-dihydro-oxazol-2-ylamine;

(S)-4-[(S)-2-(3,4-dichloro-phenoxy)-butyl]-4,5-dihydro-oxazol-2-ylamine;

(S)-4-[(S)-2-(4-chloro-2-fluoro-phenoxy)-butyl]-4,5-dihydro-oxazol-2-ylamine;

(S)-4-[(S)-2-(3-benzyloxy-phenoxy)-butyl]-4,5-dihydro-oxazol-2-ylamine;

3-[(S)-1-((S)-2-amino-4,5-dihydro-oxazol-4-ylmethyl)-propoxy]-phenol;

(S)-4-[(S)-2-(2,4,5-trifluoro-phenoxy)-butyl]-4,5-dihydro-oxazol-2-ylamine;

(S)-4-[(S)-2-(naphthalen-2-yloxy)-butyl]-4,5-dihydro-oxazol-2-ylamine;

(S)-4-[(S)-2-(2,4-dichloro-phenoxy)-butyl]-4,5-dihydro-oxazol-2-ylamine; and (S)-4-[(S)-2-(quinolin-6-yloxy)-butyl]-4,5-dihydro-oxazol-2-ylamine.

A compound of formula I-3

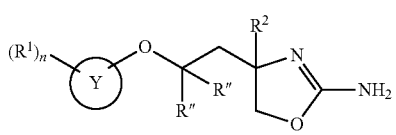

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
R² is hydrogen or lower alkyl;
Y is aryl, cycloalkyl or heteroaryl; and
n is 1, 2 or 3;
or a pharmaceutically suitable acid addition salt.

A compound of formula I-4

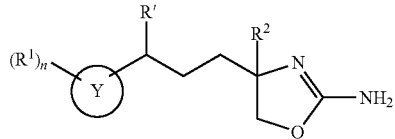

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R' is lower alkyl, lower alkoxy or lower alkyl substituted by halogen;
R² is hydrogen or lower alkyl;
Y is aryl, cycloalkyl or heteroaryl; and
n is 1, 2 or 3;
or a pharmaceutically suitable acid addition salt.

The following specific compounds are preferred:
(4S)-4-(4,4,4-trifluoro-3-phenyl-butyl)-4,5-dihydro-oxazol-2-ylamine;
(4S)-4-(3-phenyl-butyl)-4,5-dihydro-oxazol-2-ylamine;
(4S)-4-(3-phenyl-pentyl)-4,5-dihydro-oxazol-2-ylamine;
(4S)-4-[3-(4-fluoro-phenyl)-butyl]-4,5-dihydro-oxazol-2-ylamine;
(4S)-4-[3-(4-fluoro-phenyl)-pentyl]-4,5-dihydro-oxazol-2-ylamine;
(4S)-4-methyl-4-(3-phenyl-butyl)-4,5-dihydro-oxazol-2-ylamine;
(4S)-4-[3-(4-chloro-phenyl)-pentyl]-4,5-dihydro-oxazol-2-ylamine;
(4S)-4-[3-(3-trifluoromethyl-phenyl)-pentyl]-4,5-dihydro-oxazol-2-ylamine;
(4S)-4-(3-m-tolyl-pentyl)-4,5-dihydro-oxazol-2-ylamine;
(S)-4-[(S)-3-(4-fluoro-phenyl)-butyl]-4,5-dihydro-oxazol-2-ylamine;
(S)-4-[(R)-3-(4-fluoro-phenyl)-butyl]-4,5-dihydro-oxazol-2-ylamine; and
(4S)-4-[3-(3,5-difluoro-phenyl)-pentyl]-4,5-dihydro-oxazol-2-ylamine.

A compound of formula I-5

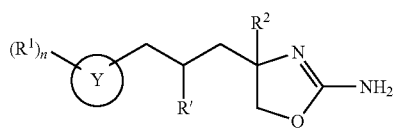

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;

R' is lower alkyl, lower alkoxy or lower alkyl substituted by halogen;
$R^2$ is hydrogen or lower alkyl;
Y is aryl, cycloalkyl or heteroaryl; and
n is 1, 2 or 3;
or a pharmaceutically suitable acid addition salt.

The following specific compound is preferred:
(4S)-4-(2-methyl-3-phenyl-propyl)-4,5-dihydro-oxazol-2-ylamine.

A compound of formula I-6

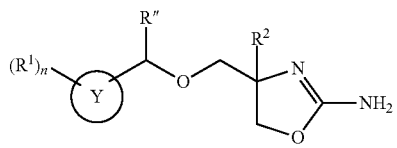

wherein
$R^1$ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
$R^2$ is hydrogen or lower alkyl;
Y is aryl, cycloalkyl or heteroaryl; and
n is 1, 2 or 3;
or a pharmaceutically suitable acid addition salt.

The following specific compound is preferred:
(4S)-4-(1-phenyl-ethoxymethyl)-4,5-dihydro-oxazol-2-ylamine;
(S)-4-[(S)-1-(4-fluoro-phenyl)-ethoxymethyl]-4,5-dihydro-oxazol-2-ylamine; and
(S)-4-((S)-1-phenyl-propoxymethyl)-4,5-dihydro-oxazol-2-ylamine.

A compound of formula I-7

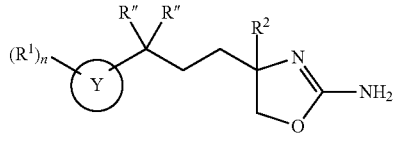

wherein
$R^1$ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
$R^2$ is hydrogen or lower alkyl;
Y is aryl, cycloalkyl or heteroaryl; and
n is 1, 2 or 3;
or a pharmaceutically suitable acid addition salt.

The following specific compounds are preferred:
(S)-4-(3-methyl-3-phenyl-butyl)-4,5-dihydro-oxazol-2-ylamine;
(S)-4-[3-(4-fluoro-phenyl)-3-methyl-butyl]-4,5-dihydro-oxazol-2-ylamine; and
(S)-4-[3-(4-chloro-phenyl)-3-methyl-butyl]-4,5-dihydro-oxazol-2-ylamine.

A compound of formula I-8

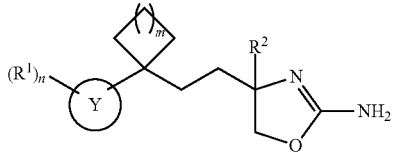

wherein
$R^1$ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
m is 0, 1, 2 or 3;
$R^2$ is hydrogen or lower alkyl;
Y is aryl, cycloalkyl or heteroaryl; and
n is 1, 2 or 3;
or a pharmaceutically suitable acid addition salt.

The following specific compounds are preferred:
(S)-4-{2-[1-(4-chloro-phenyl)-cyclopropyl]-ethyl}-4,5-dihydro-oxazol-2-ylamine;
(S)-4-[2-(1-phenyl-cyclopropyl)-ethyl]-4,5-dihydro-oxazol-2-ylamine;
(S)-4-{2-[1-(4-fluoro-phenyl)-cyclopropyl]-ethyl}-4,5-dihydro-oxazol-2-ylamine;
(S)-4-{2-[1-(2,4-difluoro-phenyl)-cyclopropyl]-ethyl}-4,5-dihydro-oxazol-2-ylamine;
(S)-4-{2-[1-(3-chloro-4-fluoro-phenyl)-cyclopropyl]-ethyl}-4,5-dihydro-oxazol-2-ylamine;
(S)-4-{2-[1-(3,4-difluoro-phenyl)-cyclopropyl]-ethyl}-4,5-dihydro-oxazol-2-ylamine;
(S)-4-{2-[1-(4-chloro-phenyl)-cyclobutyl]-ethyl}-4,5-dihydro-oxazol-2-ylamine;
(S)-4-{2-[1-(3,5-difluoro-phenyl)-cyclopropyl]-ethyl}-4,5-dihydro-oxazol-2-ylamine;
(S)-4-{2-[1-(3-chloro-5-fluoro-phenyl)-cyclopropyl]-ethyl}-4,5-dihydro-oxazol-2-ylamine; and
(S)-4-{2-[1-(4-bromo-phenyl)-cyclopropyl]-ethyl}-4,5-dihydro-oxazol-2-ylamine.

A compound of formula I-9

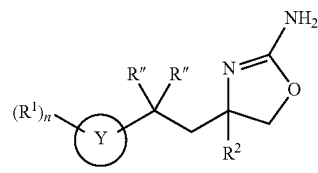

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
R² is hydrogen or lower alkyl;
Y is aryl, cycloalkyl or heteroaryl; and
n is 1, 2 or 3;
or a pharmaceutically suitable acid addition salt.

A compound of formula I-10

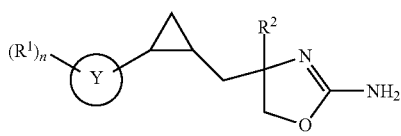

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.

The following specific compound is preferred:
(4S)-4-(2-phenyl-cyclopropylmethyl)-4,5-dihydro-oxazol-2-ylamine.

A compound of formula I-11

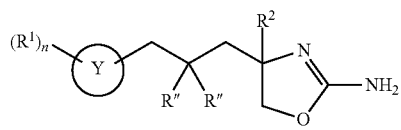

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
R² is hydrogen or lower alkyl;
Y is aryl, cycloalkyl or heteroaryl; and
n is 1, 2 or 3;
or a pharmaceutically suitable acid addition salt.

The following specific compound is preferred: (RS)-4-(2,2-dimethyl-3-phenyl-propyl)-4,5-dihydro-oxazol-2-ylamine.

A compound of formula I-12

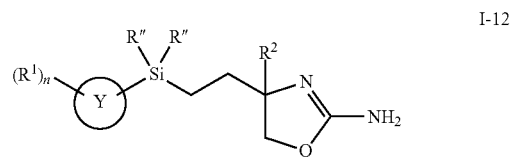

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
R² is hydrogen or lower alkyl;
Y is aryl, cycloalkyl or heteroaryl; and
n is 1, 2 or 3;
or a pharmaceutically suitable acid addition salt.

The following specific compounds are preferred:
(S)-4-[2-(dimethyl-phenyl-silanyl)-ethyl]-4,5-dihydro-oxazol-2-ylamine;
(S)-4-{2-[(3-chloro-phenyl)-dimethyl-silanyl]-ethyl}-4,5-dihydro-oxazol-2-ylamine; and
(S)-4-{2-[(4-chloro-phenyl)-dimethyl-silanyl]-ethyl}-4,5-dihydro-oxazol-2-ylamine.

A compound of formula I-13

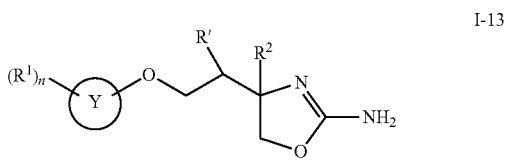

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R' is lower alkyl, lower alkoxy or lower alkyl substituted by halogen;
R² is hydrogen or lower alkyl;
Y is aryl, cycloalkyl or heteroaryl; and
n is 1, 2 or 3;
or a pharmaceutically suitable acid addition salt.

A compound of formula I-14

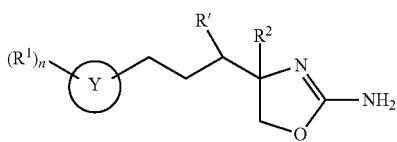

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R' is lower alkyl, lower alkoxy or lower alkyl substituted by halogen;
R² is hydrogen or lower alkyl;
Y is aryl, cycloalkyl or heteroaryl; and
n is 1, 2 or 3;
or a pharmaceutically suitable acid addition salt.
The following specific compound is preferred:
(4S)-4-(1-methyl-3-phenyl-propyl)-4,5-dihydro-oxazol-2-ylamine.

A compound of formula I-15

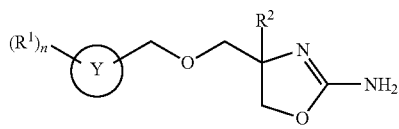

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, or benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.

A compound of formula I-16

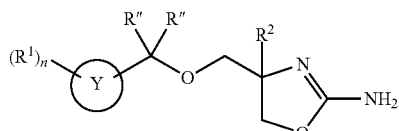

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R" is lower alkyl or lower alkyl substituted by halogen;
R² is hydrogen or lower alkyl;
Y is aryl, cycloalkyl or heteroaryl; and
n is 1, 2 or 3;
or a pharmaceutically suitable acid addition salt.
The following specific compound is preferred:
(S)-4-[1-(4-Fluoro-phenyl)-1-methyl-ethoxymethyl]-4,5-dihydro-oxazol-2-ylamine.

A compound of formula I-17

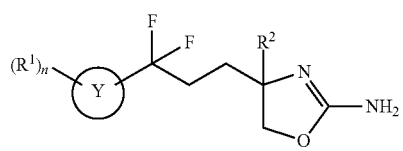

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.
The following specific compound is preferred:
(S)-4-[3,3-difluoro-3-(4-fluoro-phenyl)-propyl]-4,5-dihydro-oxazol-2-ylamine.

A compound of formula I-18

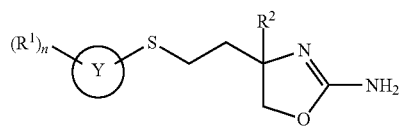

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)₂-lower alkyl, C(O)OCH₂-phenyl, OCH₂-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.

The following specific compound is preferred:
(S)-4-[2-(4-fluoro-phenylsulfanyl)-ethyl]-4,5-dihydro-oxazol-2-ylamine.

A compound of formula I-19

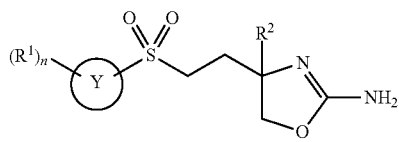

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.

A compound of formula I-20

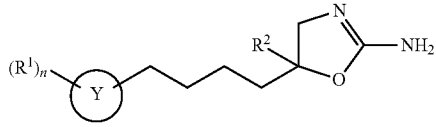

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.

The following specific compound is preferred:
(S)-4-(4-Phenyl-butyl)-4,5-dihydro-oxazol-2-ylamine.

A compound of formula I-21

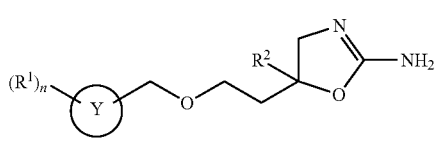

wherein
R¹ is hydrogen, lower alkyl, lower alkoxy, lower alkyl substituted by halogen, lower alkoxy substituted by halogen, halogen, cyano, nitro, hydroxy, C(O)O-lower alkyl, S(O)$_2$-lower alkyl, C(O)OCH$_2$-phenyl, OCH$_2$-phenyl, tetrazol-1-yl, phenyl optionally substituted by halogen, phenyloxy optionally substituted by halogen, benzyl optionally substituted by halogen or benzyloxy optionally substituted by halogen, wherein the substituents for n>1 are the same or different;
R² is hydrogen or lower alkyl;
Y is aryl, cycloalkyl or heteroaryl; and
n is 1, 2 or 3;
or a pharmaceutically suitable acid addition salt.

The following specific compound is preferred:
(S)-4-(2-Benzyloxy-ethyl)-4,5-dihydro-oxazol-2-ylamine.

A further embodiment of the invention are compounds of formula I

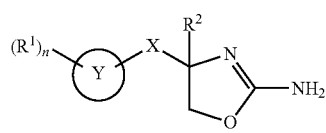

wherein
R¹ is hydrogen, lower alkyl, lower alkoxy, lower alkyl substituted by halogen, lower alkoxy substituted by halogen, halogen, phenyl optionally substituted by halogen, phenyloxy optionally substituted by halogen, benzyl optionally substituted by halogen or benzyloxy optionally substituted by halogen, wherein the substituents for n>1 are the same or different;
X is —O—(CH$_2$)$_2$—, —O—CHR″—CH$_2$—, —O—CR″$_2$—CH$_2$—, —CHR′—(CH$_2$)$_2$—, —CR″$_2$—(CH$_2$)$_2$—, —CH$_2$—CHR′—CH$_2$—, —CH$_2$—CR″$_2$—CH$_2$—, —CHR″—O—CH$_2$—, —CR″$_2$—CH$_2$—, —SiR″$_2$—(CH$_2$)$_2$—,

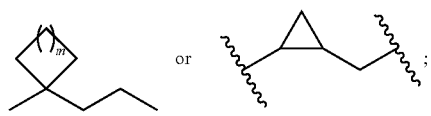

wherein m is 0, 1, 2 or 3;
R′ is lower alkyl, lower alkoxy or lower alkyl substituted by halogen;
R″ is lower alkyl or lower alkyl substituted by halogen;
R² is hydrogen or lower alkyl;
Y is aryl; and
n is 1, 2 or 3;
or a pharmaceutically suitable acid addition salt.

The present compounds of formula I and their pharmaceutically acceptable salts can be prepared by methods known in the art, for example, by processes described below, which processes comprise
a) Reacting a compound of formula

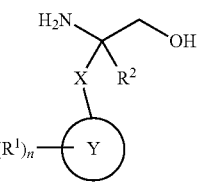

with cyanogen bromide
to obtain a compound of formula

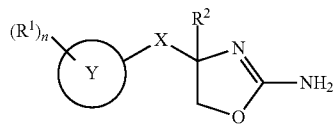

I wherein the definitions are as described above, or b) reacting a compound of formula

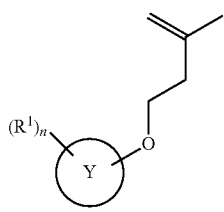

XXVII with AgOCN and I$_2$ and then with aqueous ammonia
to obtain a compound of formula

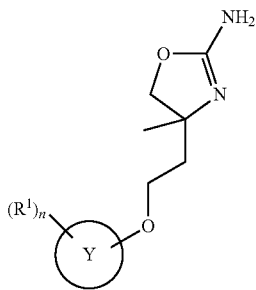

I-1-2 wherein the definitions are as described above, or c) reacting a compound of formula

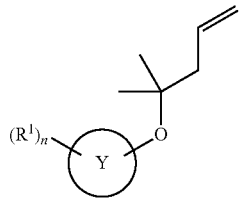

LVII with AgOCN and I$_2$ and then with aqueous ammonia
to obtain a compound of formula

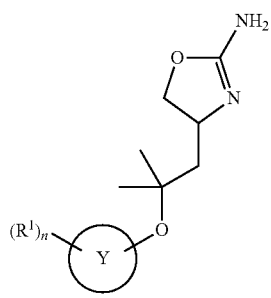

I-3 wherein the definitions are as described above, and if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-18. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 18, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

GENERAL PROCEDURE
Scheme 1

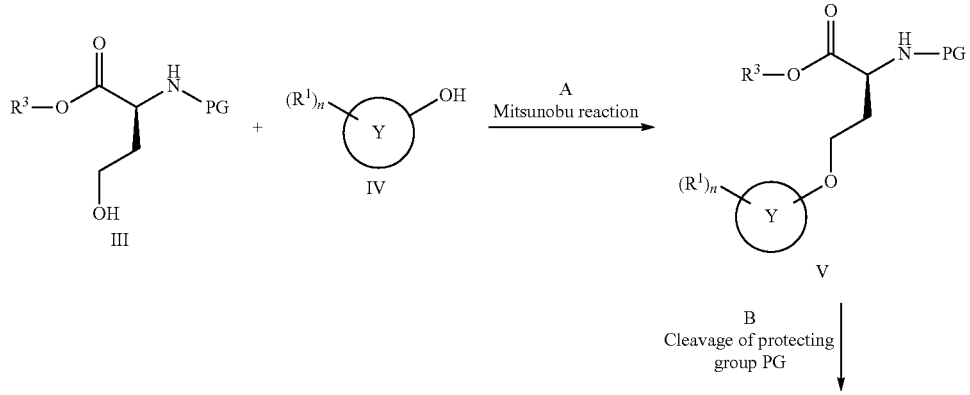

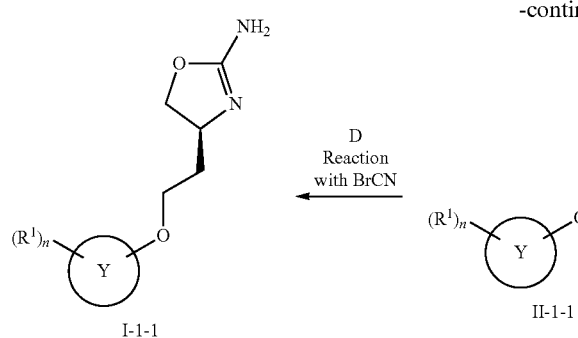

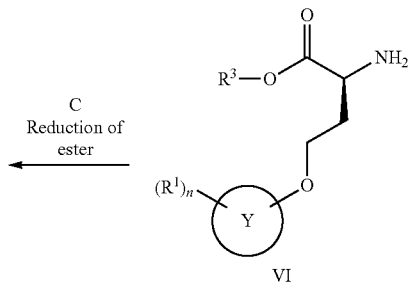

The substituents are as described above and R³ is methyl or ethyl.

Step A: Mitsunobu reaction of an N-protected (S)-4-hydroxybutyric acid alkyl ester III with phenol derivatives IV can be accomplished by using a phosphine such as triphenylphosphine and an azodicarboxylate reagent such as diethylazodicarboxylate, diisopropylazodicarboxylate, or di-tert-butylazodicarboxylate in a solvent such as THF at temperatures from room temperature to 100° C. for 1-18 hrs.

Preferred conditions are triphenylphosphine and diisopropylazodicarboxylate in THF at room temperature for 16 h. A preferred protecting group is the tert-butoxycarbonyl group, preferred alkyl groups R³ are methyl and ethyl.

Step B: Cleavage of the amino protecting group can be effected with a variety of methods known in the art. The tert-butoxycarbonyl group can be cleaved using a mineral acid such as HCl, H₂SO₄ or H₃PO₄ or an organic acid such as CF₃COOH, CHCl₂COOH, HOAc or p-toluonesulfonic acid in a solvent such as CH₂Cl₂, CHCl₃, THF, MeOH, EtOH or H₂O at 0 to 60° C. Preferred conditions are CF₃COOH in dichloromethane at room temperature overnight.

Step C: Reduction of an ester group (R³=methyl or ethyl) can be effected by treatment with LiAlH₄, LiBH₄, NaBH₄ or Red-Al in a suitable solvent such as 1,2-dimethoxyethane, THF, diethylether, toluene, MeOH or EtOH at −78° C.->reflux for 1-24 hrs. Preferred conditions are LiAlH₄ in THF at r.t. overnight or at 50° C. for 2 hours.

Step D: Cyclisation of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight.

Scheme 2

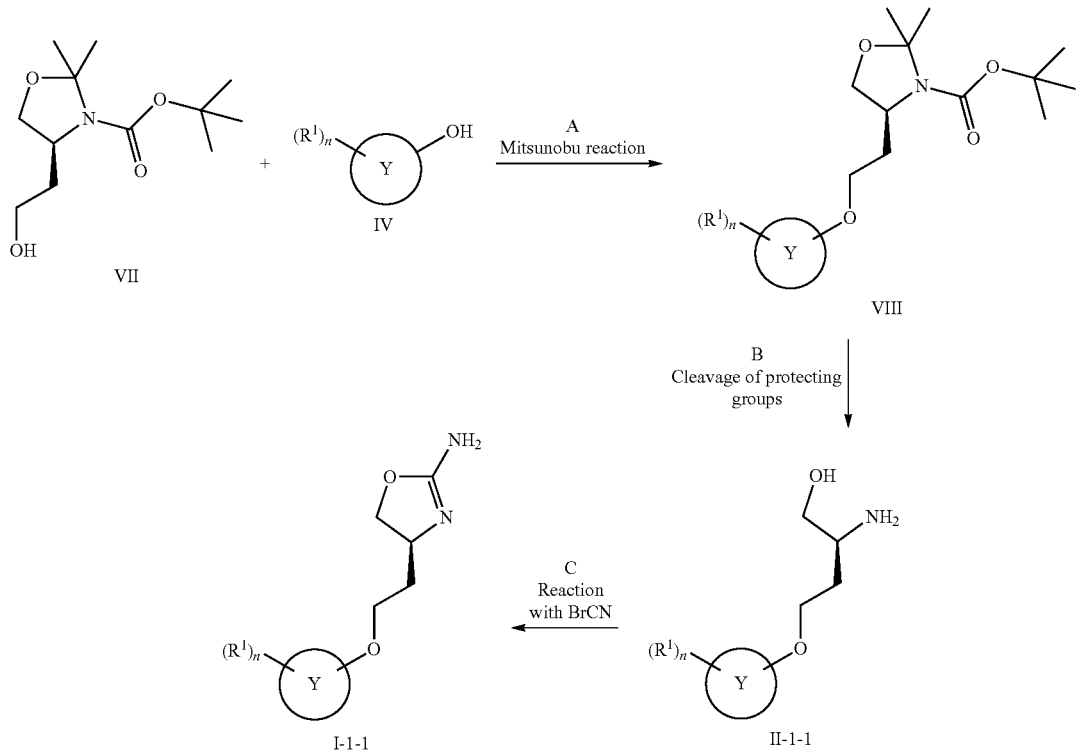

The substituents are as described above.

Step A: Mitsunobu reaction of tert-butyl (S)-4-(2-hydroxyethyl)-2,2-dimethyl-oxazolidine-3-carboxylate VII (CAS147959-18-0; synthesized according to Ma et al, Synthesis 2006, 8, 1181) with phenol derivatives IV can be accomplished by using a phosphine such as triphenylphosphine and an azodicarboxylate reagent such as diethylazodicarboxylate, diisopropylazodicarboxylate, or di-tert-butylazodicarboxylate in a solvent such as THF at temperatures from room temperature to 100° C. for 1-18 hrs. Preferred conditions are triphenylphosphine and diethyl azodicarboxylate in THF at 100° C. for 20 min in the microwave.

Step B: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C. Preferred conditions are 5.5 N HCl in EtOH at room temperature for 18 hrs.

Step C: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

be accomplished as a one-pot reaction or as a stepwise procedure by various methods known to people skilled in the art (this transformation is known as an Asymmetric or Diastereoselective Strecker reaction, see Juaristi et al, *Tetrahedron Asymmetry* 1999, 10, 2441).

Preferred conditions are a two step procedure using (S)-(+)-p-toluenesulfinamide and titanium ethoxide in dichloromethane at room temperature overnight as the first step followed by addition of diethylaluminium cyanide in tetrahydrofuran at −78° C. overnight as the second step as described for instance by Davis et al in Heterocycles 2002, 58, 251.

Step B: Cleavage of the auxiliary and saponification of the nitrile can be effected under acidic conditions in different solvents. Suitable acids are mineral acids such as HCl, $H_2SO_4$ or $H_3PO_4$ or organic acids such as $CF_3COOH$, $CHCl_2COOH$, HOAc or p-toluonesulfonic acid in a solvent such as MeOH or EtOH at −40 to 100° C. Preferred conditions are refluxing with 5.5 N HCl in EtOH for 4 hrs.

Step C: Reduction of an ester group ($R^3$=methyl or ethyl) can be effected by treatment with $LiAlH_4$, $LiBH_4$, $NaBH_4$ or Red-Al in a suitable solvent such as 1,2-dimethoxyethane, THF, diethylether, toluene, MeOH or EtOH at −78° C.->reflux for 1-24 hrs. Preferred conditions are $LiAlH_4$ in THF at r.t. or at 50° C. for several hours.

Scheme 3

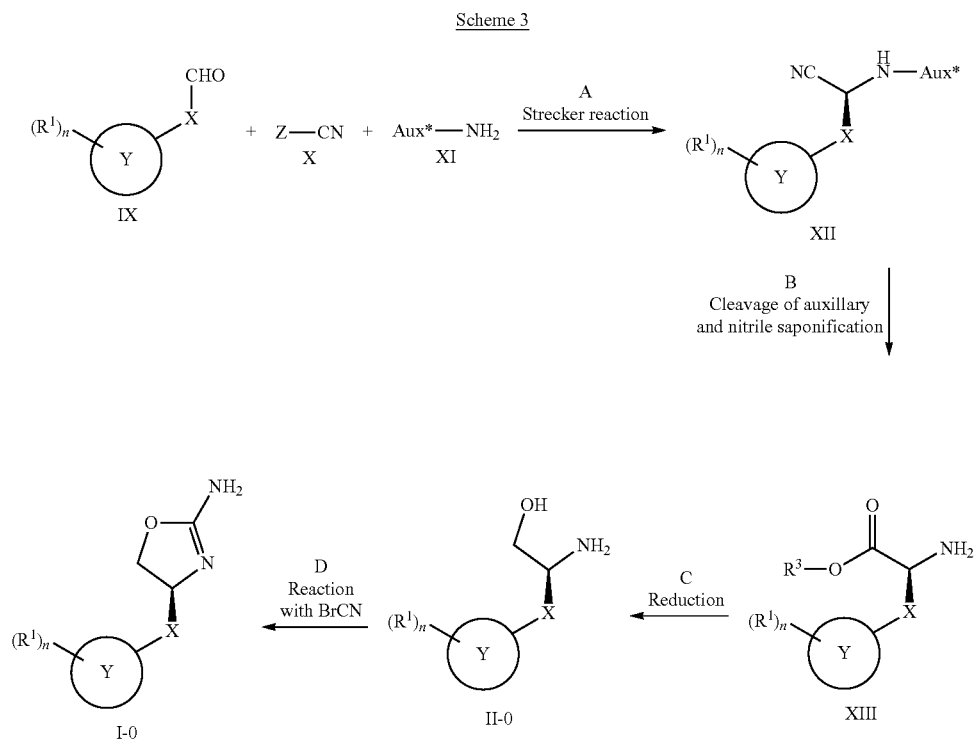

The substituents are as described above, $R^3$ is methyl or ethyl, Z is trimethylsilyl or diethylaluminum and Aux* is (S)-1-phenylethyl, (S)-1-(4-methoxyphenyl)ethyl or (S)-p-toluenesulfinyl.

Step A: Reaction of a suitable aldehyde IX, a cyanide source X and a chiral amine XI to form aminonitrile XII can Step D: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 4

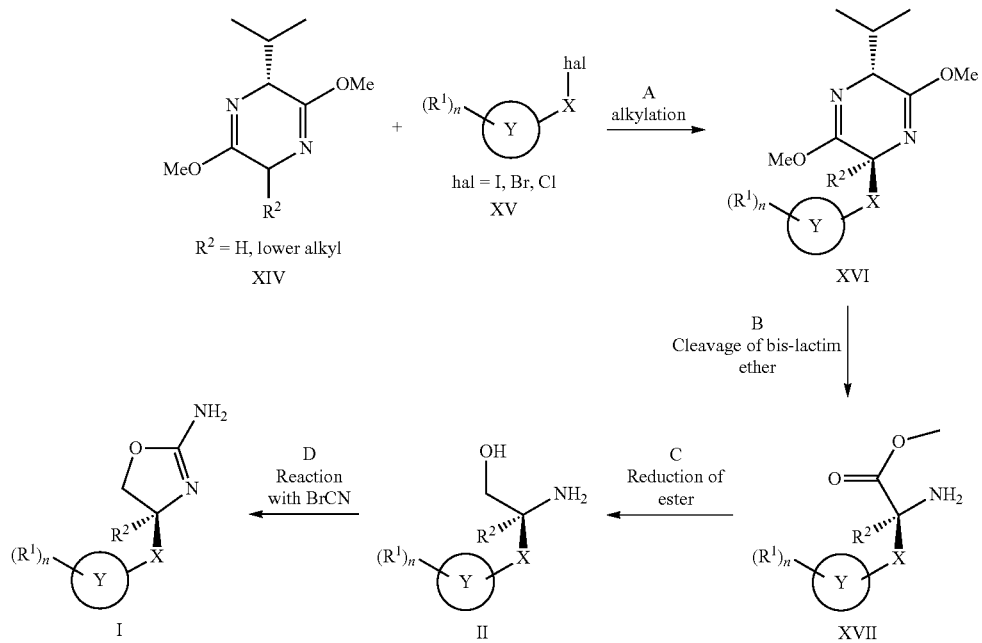

The substituents are as described above.

Step A: Deprotonation of bis-lactimether XIV (also called "Schöllkopf's chiral auxiliary") with a suitable base such as n-butyl-lithium or tert-butyl-lithium in an appropriate organic solvent such as tetrahydrofuran at a low temperature, optionally in the presence of an additive such as hexamethylphosphoramide, followed by addition of the organic halide XV and reaction for several hours leads to product XVI (Vassiliou, S. et at *Synlett* 2003, 2398-2400; Schöllkopf, U. *Topics Curr. Chem.* 1983, 109, 65).

Preferred conditions are the use of tert-butyllithium and an organic iodide in tetrahydrofuran at −78° C. and allowing the mixture to reach room temperature overnight.

Step B: Cleavage of bis-lactim ether product XVI under acidic conditions using a mineral acid such as HCl, $H_2SO_4$ or $H_3PO_4$ or an organic acid such as $CF_3COOH$, $CHCl_2COOH$, HOAc or p-toluonesulfonic acid in a solvent such as acetonitrile, $CH_2Cl_2$, $CHCl_3$, THF, MeOH, EtOH or $H_2O$ at 0 to 60° C. Preferred conditions are 10% trifluoroacetic acid in a mixture of water and acetonitrile (1:3) at 40° C. overnight.

Step C: Reduction of the ester XVII can be effected by treatment with $LiAlH_4$, $LiBH_4$, $NaBH_4$ or Red-Al in a suitable solvent such as 1,2-dimethoxyethane, THF, diethylether, toluene, MeOH or EtOH at −78° C.->reflux for 1-24 hrs. Preferred conditions for acids and esters are $LiAlH_4$ in THF at r.t. overnight.

Step D: Cyclization of the amino alcohol II to the corresponding 2-aminooxazoline I can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 5

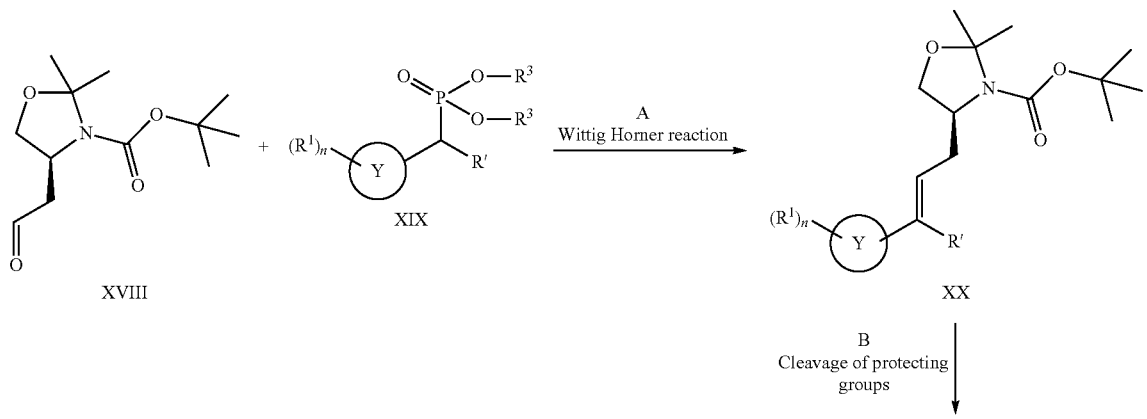

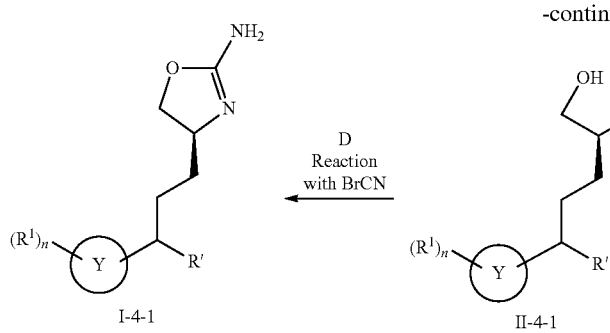

-continued

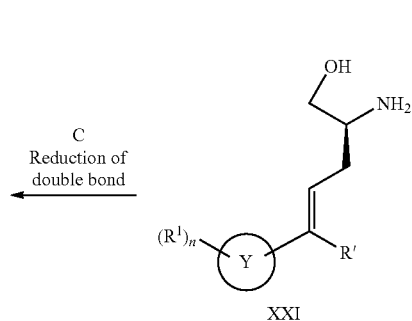

The substituents are as described above and R³ is methyl or ethyl.

Step A: Wittig Horner reaction between (S)-2,2-dimethyl-4-(2-oxo-ethyl)-oxazolidine-3-carboxylic acid tert-butyl ester XVIII (CAS147959-19-1) and a benzyl-substituted phosphonic acid dialkyl ester XIX can be accomplished by using a base such as NaH, KOtBu, NaOMe, NaOEt, n-BuLi, LiHMDS, NaHMDS, KHMDS, or LDA in a solvent such as THF, dioxane, acetonitrile, 1,2-dimethoxyethan, DMF, benzene, toluene or mixtures thereof at temperatures from −78° C. −80° C. for 15 min −8 hrs and if appropriate optional addition of a crown ether for ylide generation and then condensing the ylide with the carbonyl compound in the same solvent at a temperature between 0 and 80° C. for 1-24 hrs. Alternatively, the base, the carbonyl compound and the base and the optional crown ether can be added to the reaction mixture at the same time without preformation of the ylide at temperatures from −78° C. to 80° C.

Preferred conditions are ylide formation at −78° C. using LDA solution in hexane/THF as base and THF as solvent, reacting the phosphonic acid ester for 30 min at −78° C., and then condensation with the carbonyl component at −78° C. and then leaving to warm to room temperature overnight.

Step B: Simultaneous cleavage of the amino alcohol protecting groups can be effected with a mineral acid such as HCl, H₂SO₄ or H₃PO₄ or an organic acid such as CF₃COOH, CHCl₂COOH, HOAc or p-toluonesulfonic acid in a solvent such as CH₂Cl₂, CHCl₃, THF, MeOH, EtOH or H₂O at 0 to 60° C. Preferred conditions are 4 N HCl in dioxane at room temperature for 18 hrs.

Step C: Reduction of the alkene can be effected by hydrogenation with hydrogen under normal or elevated pressure or by transfer hydrogenation using ammonium formate or cyclohexadiene as hydrogen source with a catalyst such as PtO₂, Pd—C or Raney nickel in solvents such as MeOH, EtOH, H₂O, dioxane, THF, HOAc, EtOAc CH₂Cl₂, CHCl₃, DMF or mixtures thereof. Alternatively, the reduction of the alkene can be effected by Mg in MeOH or by LiAlH₄ in THF or diethylether.

Preferred conditions for R¹ iodine, bromine or chlorine are hydrogenation in the presence of Pd/C as catalyst with EtOH as solvent.

Preferred conditions for R¹ iodine, bromine or chlorine are hydrogenation in the presence of PtO₂ as catalyst with THF or EtOAc as solvent.

Step D: Cyclization of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight.

Scheme 6

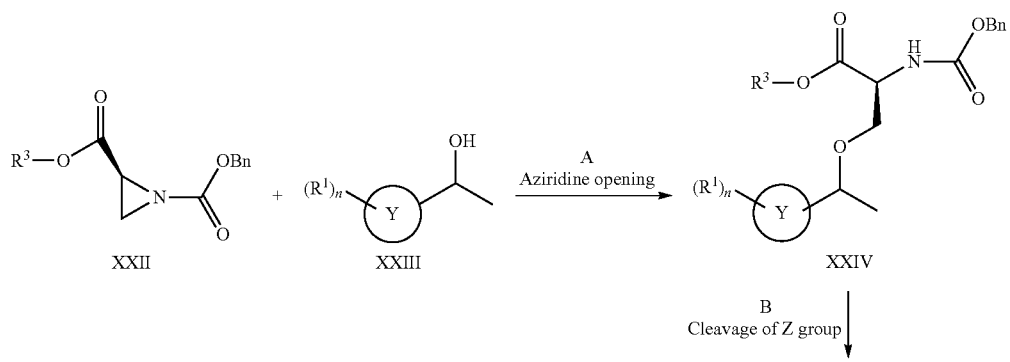

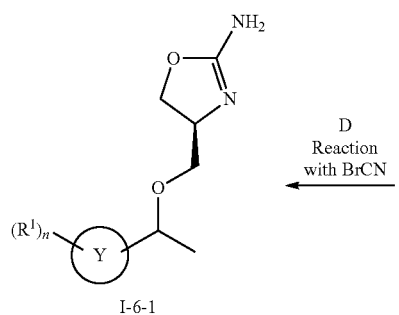

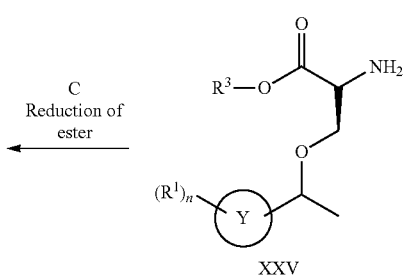

The substituents are as described above and R³ is methyl or ethyl.

Step A: Reaction of aziridine XXII with benzyl alcohol XXIII can be accomplished by treating the components with a suitable catalyst, for instance a Lewis acid with or without the addition of solvent. Preferred conditions are stirring the components with boron trifluoride etherate for several hours at room temperature in dichloromethane.

Step B: Cleavage of the N-protecting group can be effected by careful hydrogenation. Preferred conditions are hydrogenation using 5% palladium on charcoal and addition of ammonia.

Step C: Reduction of an ester group (R³=methyl or ethyl) can be effected by treatment with LiAlH₄, LiBH₄, NaBH₄ or Red-Al in a suitable solvent such as 1,2-dimethoxyethane, THF, diethylether, toluene, MeOH or EtOH at −78° C.->reflux for 1-24 hrs. Preferred conditions are LiAlH₄ in THF at r.t. for 2 hours.

Step D: Cyclization of the amino alcohol to the corresponding 2-aminooxazoline can be accomplished by treatment with cyanogen bromide in THF as solvent and K₂CO₃ as base at r.t. overnight, or by treatment with cyanogen bromide in methanol as solvent and sodium acetate as base at 0° C. to r.t. overnight.

Scheme 7

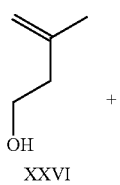

XXVI

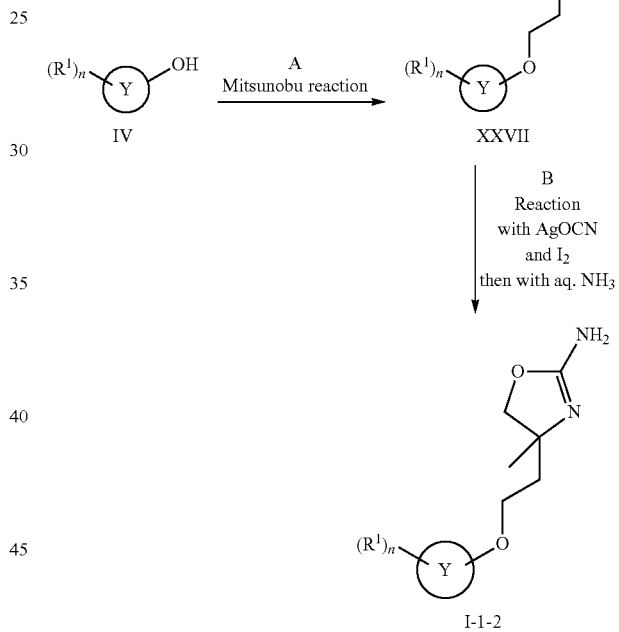

The substituents are as described above.

Step A: Mitsunobu reaction of 3-methyl-3-buten-1-ol XXVI with phenol derivatives IV can be accomplished by using a phosphine such as triphenylphosphine and an azodicarboxylate reagent such as diethylazodicarboxylate, diisopropylazodicarboxylate, or di-tert-butylazodicarboxylate in a solvent such as THF at temperatures from room temperature to 100° C. for 1-18 hrs. Preferred conditions are triphenylphosphine and diethyl azodicarboxylate in THF at 70° C. for 16 hours.

Step B: Amino-oxazioline ring formation can be accomplished by a two-step procedure comprising treatment of alkene XXVII with silver cyanate and iodine in a solvent mixture such as ethyl acetate/acetonitrile at temperatures from 0° C. to room temperature for 1-18 hrs, followed by reaction with aqueous ammonia at room temperature.

Scheme 8

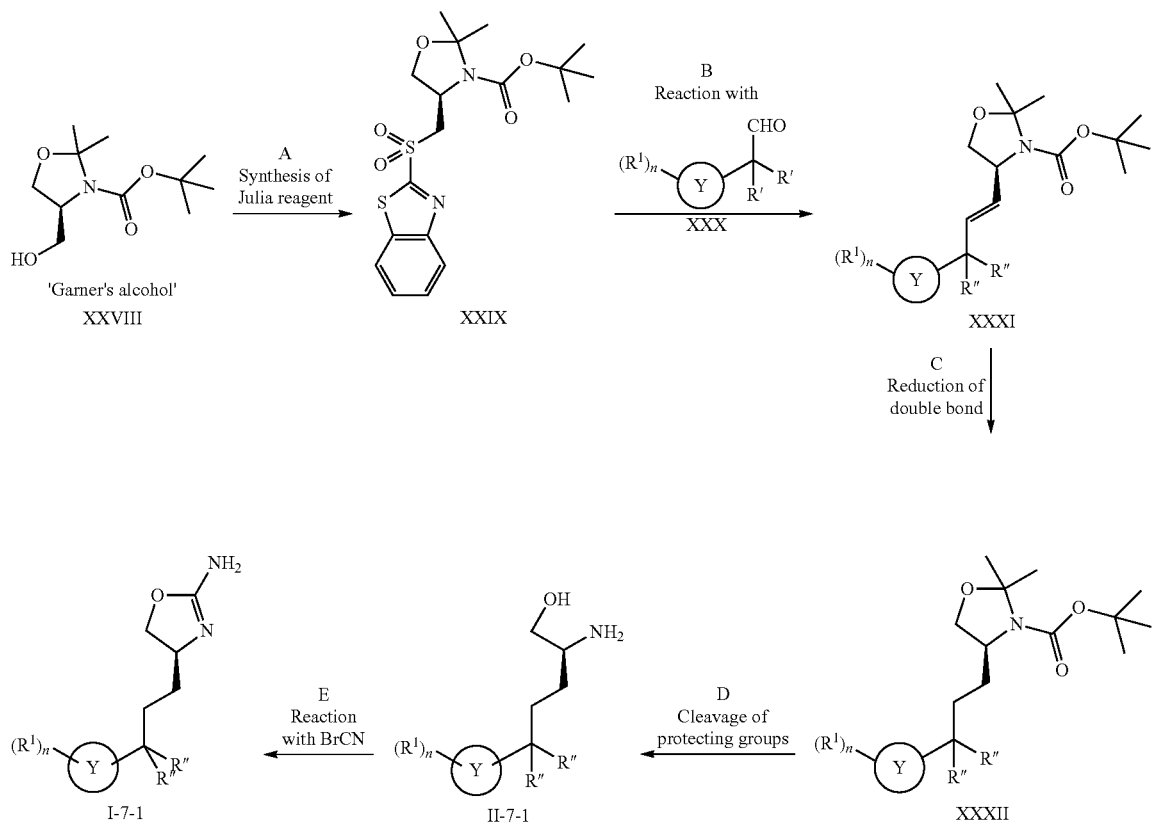

The substituents are as described above.

Step A: The synthesis of the Julia reagent (benzothiazole-2-sulfonyl derivative) XXIX from 'Garner's alcohol' XXVIII was accomplished as described in the literature (Dandanpani, S. et al., *Journal of Organic Chemistry* 2005, 70(23), 9447).

Step B: Julia reaction between an aldehyde XXX and the benzothiazole sulfonyl compound can be accomplished by using a base such as LiHMDS, NaHMDS, KHMDS, LDA, KOtBu, or DBU in a solvent such as THF, diethyl ether, 1,2-dimethoxyethane, dichloromethane, DMF or mixtures thereof at temperatures from −100° C. –r.t. for 15 min-8 hrs for anion generation and then condensing the glide with the carbonyl compound in the same solvent at temperatures between −100° C. and r.t. for 1-24 hrs.

Preferred conditions are anion generation with LiHMDS at −78° C. in THF and subsequent condensation with the carbonyl component under the same conditions.

Step C: Reduction of the alkene can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Alternatively, the reduction of the alkene can be effected by Mg in MeOH or by $LiAlH_4$ in THF or diethylether.

Preferred conditions for $R^1$ iodine, bromine or chlorine are hydrogenation in the presence of Pd/C as catalyst with EtOH as solvent.

Preferred conditions for $R^1$ iodine, bromine or chlorine are hydrogenation in the presence of $PtO_2$ as catalyst with THF or EtOAc as solvent.

Step D: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are 2N HCl in EtOH at reflux for 1-3 hrs or 4N HCl in dioxane at r.t. overnight.

Step E: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 9

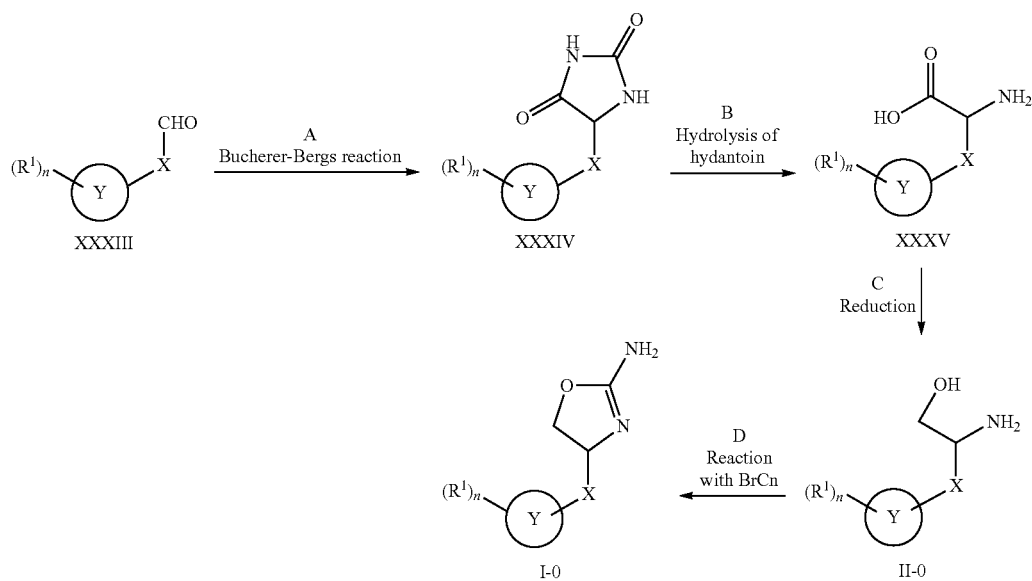

The substituents are as described above.

Step A: A hydantoin XXXIV is prepared by treatment of the appropriate aldehyde XXXIII with ammonium carbonate and sodium cyanide or potassium cyanide in a mixture of EtOH or MeOH and water at r.t.–>100° C. for several hours to several days.

Step B: Hydrolysis of the hydantoin XXXIV is effected by treatment with 1N-4N NaOH at 60° C. –120° C. for several hours to several days.

Step C: Reduction of the amino acid XXXV to the corresponding amino alcohol II-0 can be effected by treatment with LiAlH$_4$, Red-Al, DIBAH, BH$_3$ or LiBH$_4$/TMS-Cl in a suitable solvent such as 1,2-dimethoxyethane, THF, diethylether or toluene at −78° C.->reflux for 1-24 hrs. Preferred conditions are LiBH$_4$/TMSCl in THF at r.t. or at 0° C.->r.t. for several hours.

Step D: Cyclization of the amino alcohol to the corresponding 2-aminooxazoline can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight.

Scheme 10

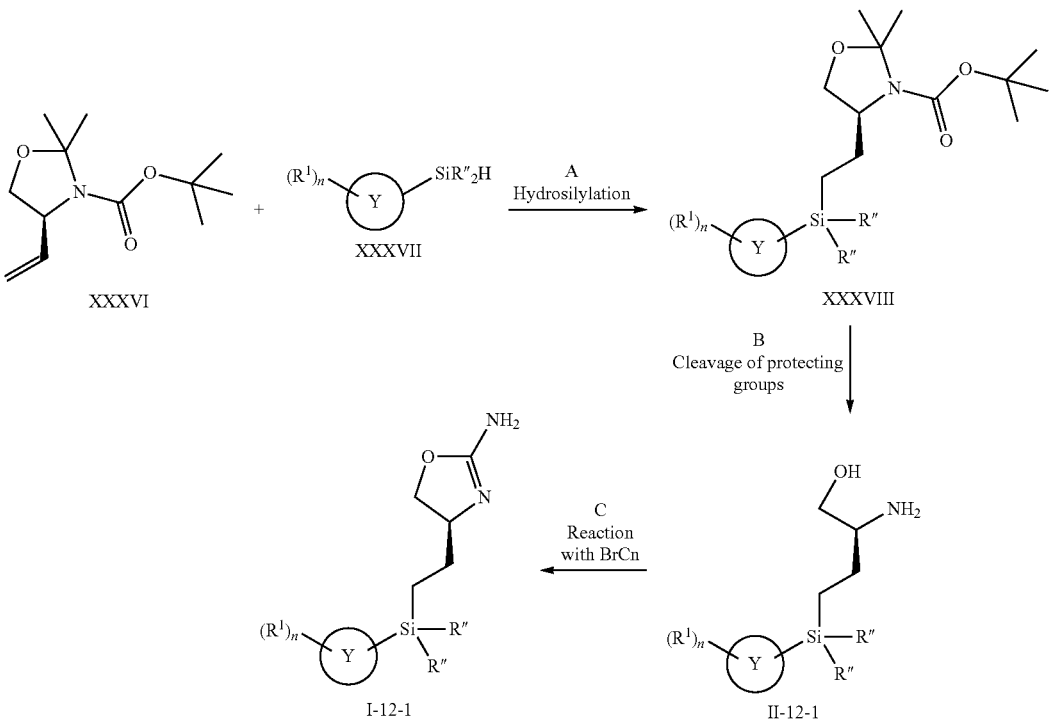

The substituents are as described above.

Step A: Hydrosilylation of (S)-2,2-dimethyl-4-vinyl-oxazolidine-3-carboxylic acid tert-butyl ester XXXVI (see Takahata et al J. Org. Chem. 2003, 68, 3603) with silane XXXVII can be accomplished by using a catalyst such as platinum(VI)-oxide, various rhenium or rhodium complexes or chloroplatinic(VI) acid in a solvent such as dichloroethane, dichloromethane, toluene, hexane, benzene or solvent-free at temperatures from 0° C. to 100° C. for 1-72 hrs. Preferred conditions are platinum(VI)-oxide without solvent at room temparature overnight.

Step B: Simultaneous cleavage of the amino alcohol protecting groups can be effected with a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C. Preferred conditions are 5.5 N HCl in EtOH at room temperature for 2 hrs.

Step C: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 11

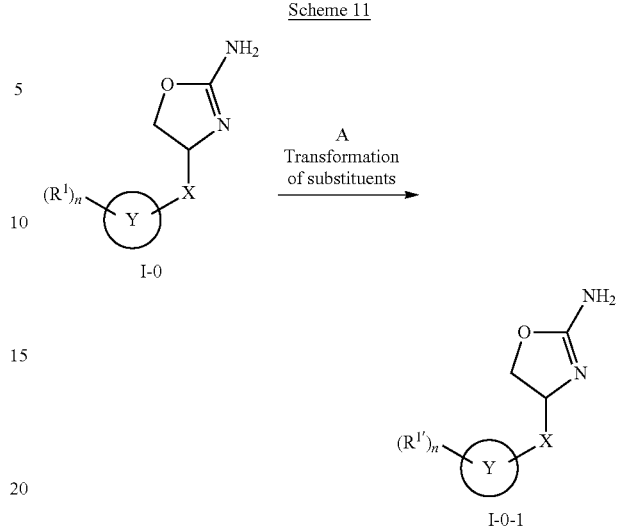

Step A: Compounds I-0 with suitable substituents $R^1$ can be transformed into new compounds I-0-1 carrying other substituents R". Such transformation can be a debenzylation (R'=O-benzyl transformed into $R^{1'}$=OH). A debenzylation can be accomplished by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof.

Preferred conditions for a debenzylation are the use of 1 atmosphere of hydrogen and palladium on charcoal in methanol at room temperature for 1 hour.

Scheme 12

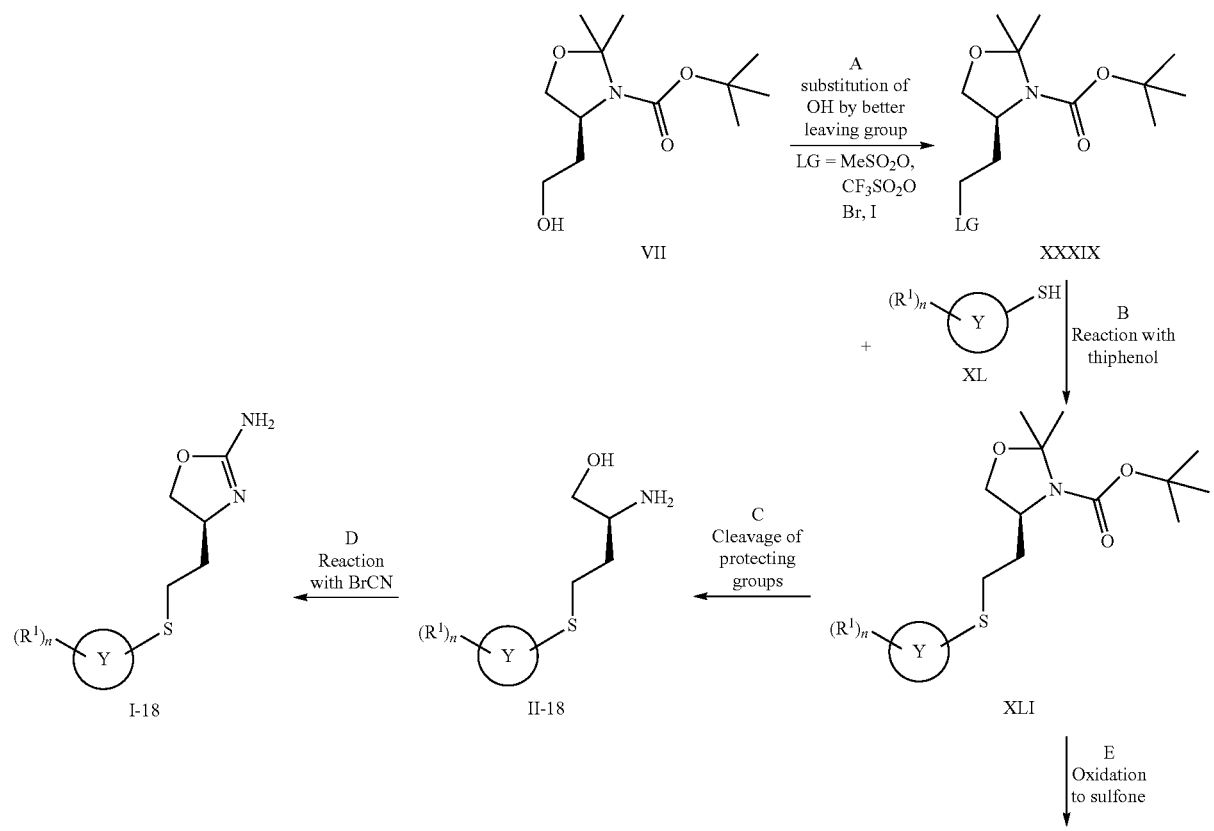

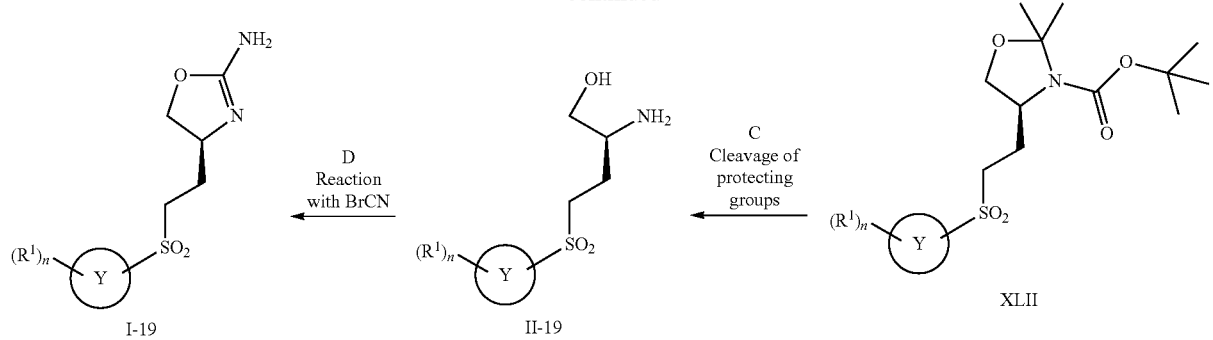

Step A: The alkohol tert-butyl (S)-4-(2-hydroxyethyl)-2,2-dimethyl-oxazolidine-3-carboxylate VII is transformed into compound XXXIX with a better leaving group. This group can be a methanesulfonate, trifluoromethanesulfonate, iodide, bromide or the like. Transformation to the methanesulfonate can be effected by using methanesulfonylchloride or methanesulfonic anhydride and a base such as triethylamine, pyridine, N-ethyldiisopropylamine or the like in a suitable solvent such as dichloromethane, ethyl acetate, tetrahydrofuran or the like. Transformation to the iodide can be accomplished by using iodine, imidazole and a phosphine such as triphenylphosphine and is described for instance in Bioorg. Med. Chem. Lett. 12, 2002, 997.

Preferred conditions are methanesulfonylchloride and N-ethyldiisopropylamine in dichloromethane at 0° C. for several hours.

Step B: The reaction of compound XXXIX with a thiophenol XL to form thioether XLI can be accomplished by stirring these compounds together in a suitable solvent with or without an additional base. Suitable solvents are tetrahydrofuran, ethyl acetate, dichloromethane, dimethylformamide, diethyl ether, 1,2-dimethoxyethane, or mixtures thereof. Suitable bases are amines like triethylamine, pyridine, ethyl-diisopropylamine or morpholine, but may also be of inorganic nature such as potassium carbonate, cesium carbonate, sodium hydride and the like.

Preferred conditions are stirring the components together with triethylamine in tetrahydrofuran at room temperature for 18 hrs.

Step C: Simultaneous cleavage of the amino alcohol protecting groups can be effected with a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are 5.5 N HCl in EtOH at room temperature for 18 hrs.

Step D: Cyclization of the amino alcohol to the corresponding 2-aminooxazoline can be accomplished by treatment with cyanogen bromide in THF as solvent and $K_2CO_3$ as base at room temperature overnight, or by treatment with cyanogen bromide in methanol as solvent and sodium acetate as base at 0° C. to room temperature overnight.

Step E: To form sulfone XLII, compound XLI can be oxidized by various reagents such peracids, hydrogen peroxide, potassium permanganate, oxone, hydroperoxides or the like in different suitable solvents such as dichloromethane, 1,2-dichloroethane, ethyl acetate, alkanes or water.

Preferred conditions are meta-chloroperoxybenzoic acid in ethyl acetate at room temperature for 18 hrs.

Compound XLII is transformed to sulfone 1-19 using reactions already described for steps C and D.

Scheme 13

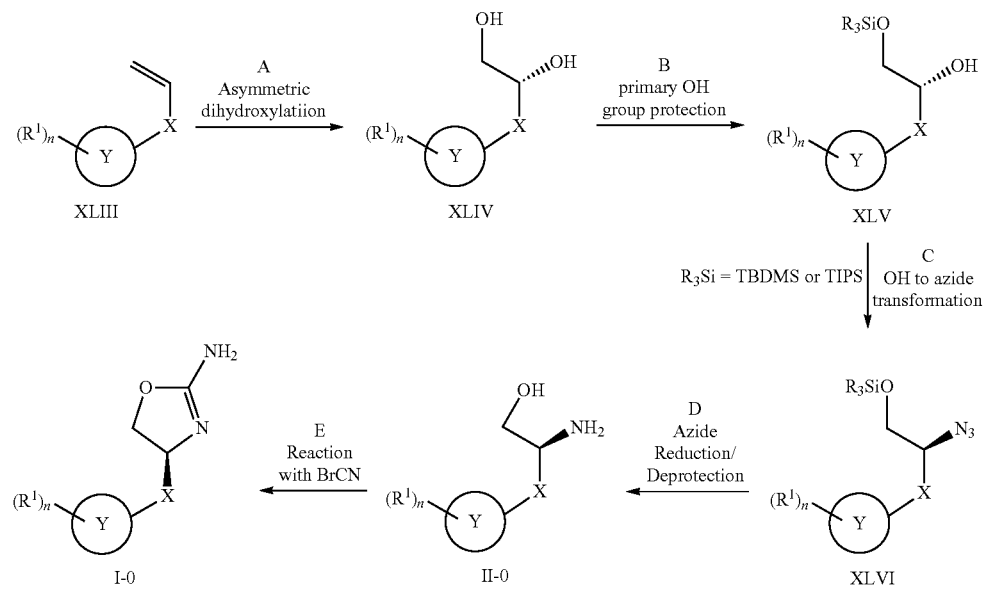

Step A: Asymmetric dihydroxylation of olefin XLIII can be achieved by reaction with osmium(IV) compound such as osmium tetroxide or potassium osmate, an oxidant such as potassium ferricyanide and a chiral ligand such as (DHQ)2PHAL in a suitable solvent such as a tert-butanol-water mixture as described by Sharpless at al in Chem. Reviews 1994, 94, 2483-2547. These reagents can be purchased separately or as a pre-formed mixture called AD-mix alpha. Preferred conditions are stirring the olefin with AD-mix alpha in tert-butanol and water for 2 days at 0° C.

Step B: Diol XLIV can be transformed into silyl compound XLV by reaction with a suitable silylating agents such as tert.-butyldimethylsilyl chloride or triisopropylsilyl chloride and a base such as imidazole, triethylamine, N-ethyldiisopropylamine, pyridine or dimethylaminopyridine in a suitable solvent such as tetrahydrofuran, dichloromethane, dimethylformamide or ethyl acetate.

Preferred conditions are tert.-butyldimethylsilyl chloride, imidazole and dimethylaminopyridine in tetrahydrofuran at 0° C. for 2 hours followed by stirring overnight at room temperature.

Step C: Formation of azide XLVI can be accomplished by first transforming the OH group of silyl compound XLV into a better leaving group followed by reaction with an inorganic azide such as sodium azide. This better leaving group can be a methanesulfonate, trifluoromethanesulfonate, iodide, bromide or the like. Transformation to the methanesulfonate can be effected by using methanesulfonylchloride or methanesulfonic anhydride and a base such as triethylamine, pyridine, N-ethyldiispropylamine or the like in a suitable solvent such as dichloromethane or tetrahydrofuran. Transformation to the iodide can be accomplished by using iodine, imidazole and a phosphine such as triphenylphosphine. Reaction with an inorganic azide can be accomplished by reacting the methanesulfonate with sodium azide in a suitable solvent such as dimethylformamide or dimethylsulfoxide at room temperature or elevated temperature.

Preferred conditions are transformation of the alcohol into the mesylate by using methanesulfonylchloride and triethylamine in dichloromethane at 0° C. for 2 hours followed by reaction with sodium azide overnight at 100° C. in dimethylformamide.

Step D: Transformation of the azide XLVI to aminoalcohol II-0 can be accomplished by using a tetrahydridoaluminate such as lithiumaluminiumhydride in a suitable solvent like tetrahydrofuran, diethylether or dioxane at temperatures between 0° C. and the boiling point of the solvent used. During aqueous work-up the silyl group can already be removed or it is removed later by stirring with acid or a fluoride source such as tetrabutylammonium fluoride in a suitable solvent such as tetrahydrofuran. Alternatively a reaction of the azide XLVI with a phosphine such as triphenylphosphine and water in a solvent such as methanol or tetrahydrofuran (known as Staudinger reaction) followed by removal of the silyl group with acid or a fluoride source can be used. Another method would be hydrogenation of the azide XLVI using a catalyst such as palladium on charcoal followed by removal of the silyl group with acid or a fluoride source.

Preferred conditions are lithiumaluminiumhydride in THF at room temperature for 24 hours.

Step E: Cyclization of the amino alcohol to the corresponding 2-aminooxazoline can be accomplished by treatment with cyanogen bromide in THF as solvent and $K_2CO_3$ as base at room temperature overnight, or by treatment with cyanogen bromide in methanol as solvent and sodium acetate as base at 0° C. to room temperature overnight.

Scheme 14

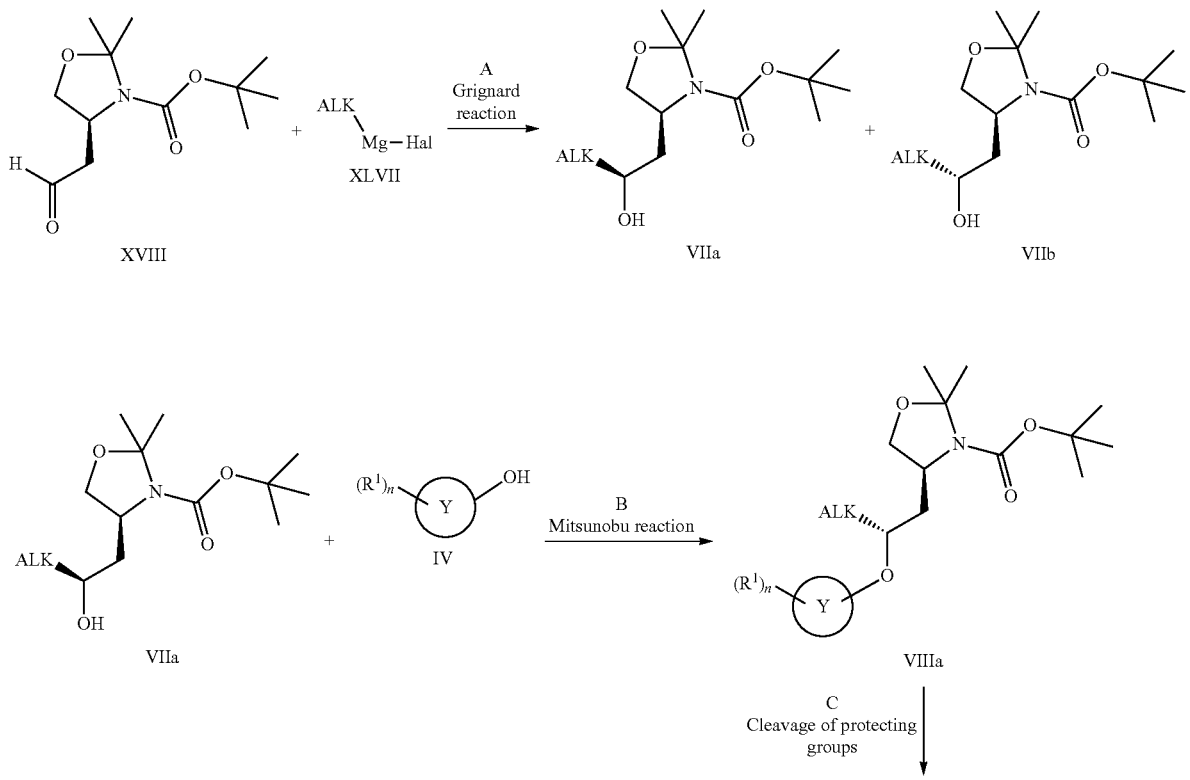

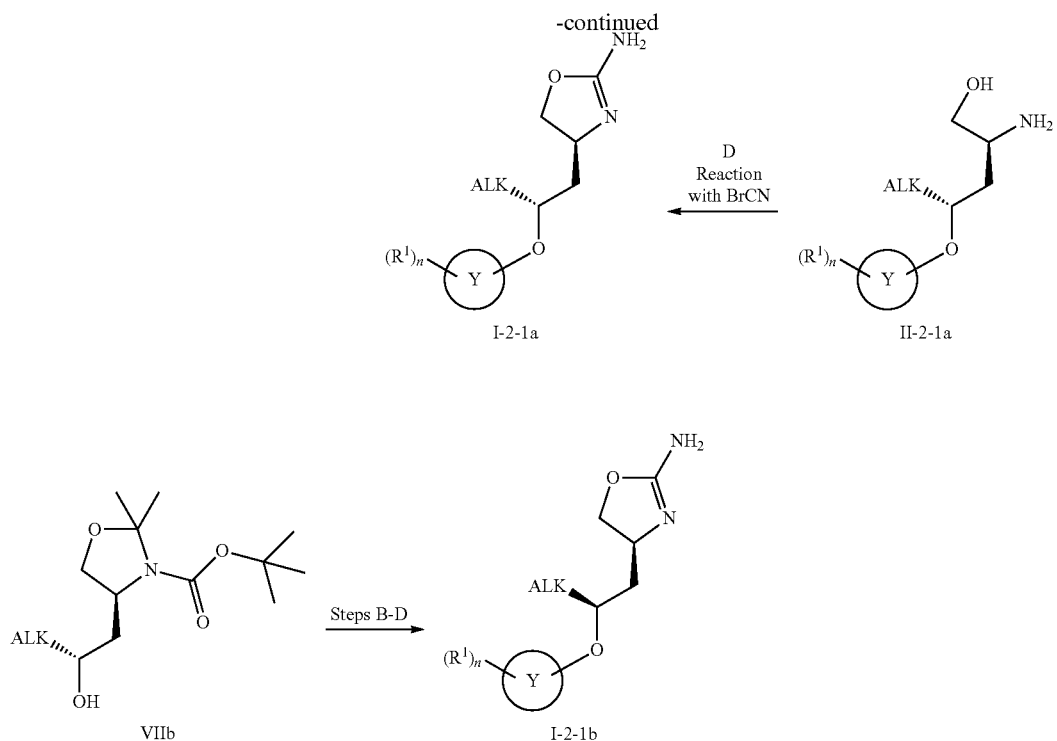

The substituents are as described above.

Step A: Grignard reaction of aldehyde XVIII with organomagnesium reagents XLVII can be accomplished in non protic ethereal solvents such as diethyl ether, THF, dioxane or dimethoxyethane at temperatures from 0° C. to the reflux temperature of the solvent for 1-18 hrs.

The reaction typically affords a mixture of diastereomeric product alcohols VIIa and VIIb which can be separated using flash column chromatography on silica gel, or by using HPLC. Preferred conditions are diethyl ether at room temperature overnight.

Step B: Mitsunobu reaction of secondary alcohol VIIa (or VIIb) with phenol derivatives IV can be accomplished by using a phosphine such as triphenylphosphine and an azodicarboxylate reagent such as diethylazodicarboxylate, diisopropylazodicarboxylate, or di-tert-butylazodicarboxylate in a solvent such as THF at temperatures from room temperature to 100° C. for 1-18 hrs. Preferred conditions are triphenylphosphine and di-tert-butyl azodicarboxylate in THF at 70° C. overnight.

Step C: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_3CN$, $CH_2Cl_2$, $CHCl_3$, THF, MeOH, EtOH or $H_2O$ at 0 to 80° C. Preferred conditions are $CF_3COOH$ in aqueous acetonitrile at 80° C. for 4 hrs.

Step D: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 15

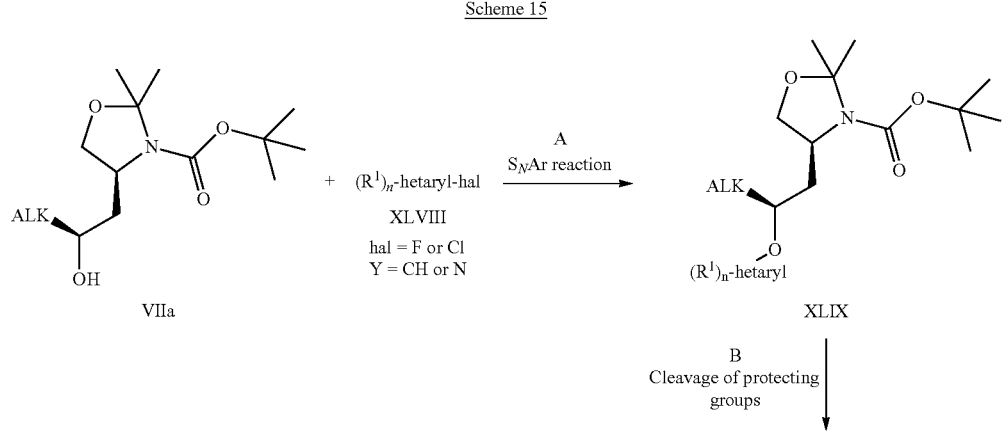

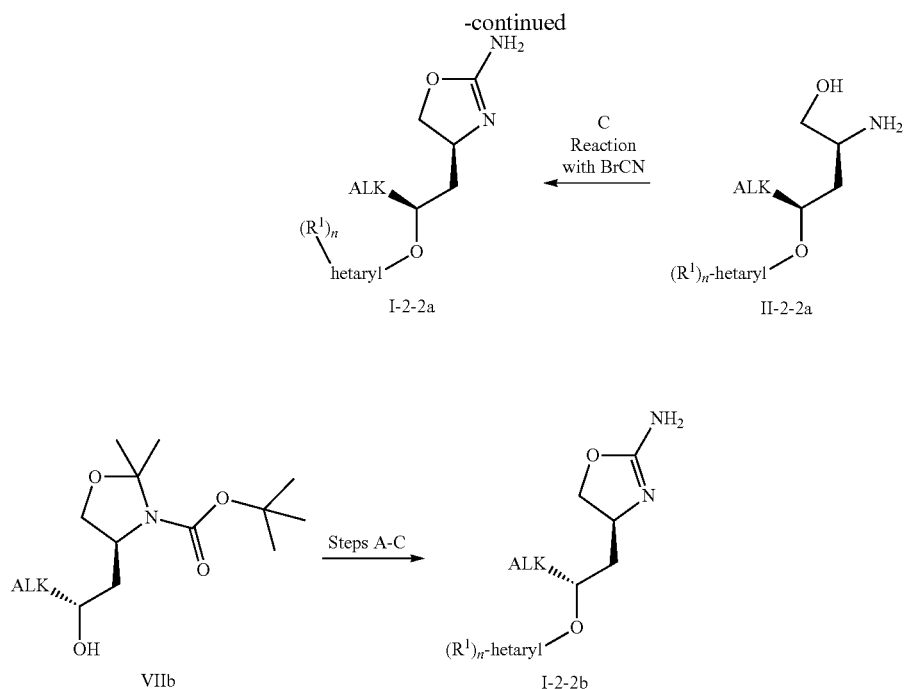

The substituents are as described above.

Step A: Aromatic nucleophilic substitution ($S_NAr$) reaction of a halogen-substituted heteroaromatic XLVIII with alcohol VIIa (or VIIb) in the presence of a base such as sodium hydride or potassium hexamethyldisilazide (KHMDS) can be accomplished in non protic ethereal solvents such as diethyl ether, THF, dioxane or dimethoxyethane at temperatures from room temperature to the reflux temperature of the solvent for 1-18 hrs. Preferred conditions are sodium hydride in THF at 70° C. for 3 hours.

Step B: Simultaneous cleavage of the amino alcohol protecting groups can be effected with a mineral acid such as HCl, $H_2SO_4$ or $H_3PO_4$ or an organic acid such as $CF_3COOH$, $CHCl_2COOH$, HOAc or p-toluonesulfonic acid in a solvent such as $CH_3CN$, $CH_2Cl_2$, $CHCl_3$, THF, MeOH, EtOH or $H_2O$ at 0 to 80° C.

Preferred conditions are $CF_3COOH$ in aqueous acetonitrile at 80° C. for 90 min.

Step C: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 16

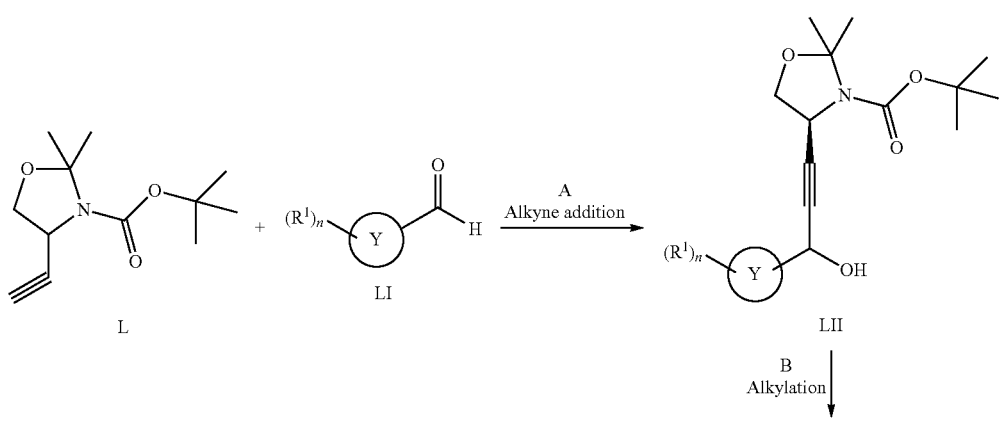

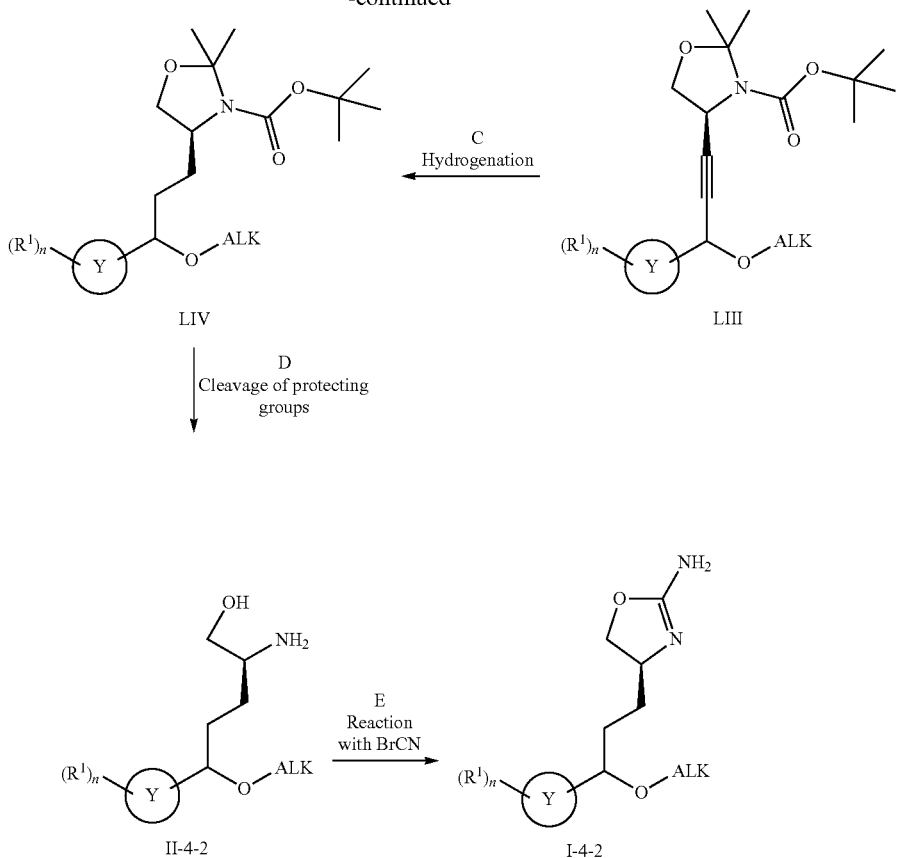

The substituents are as described above.

Step A: Addition reaction between alkyne L (CAS 173065-16-2) and an aldehyde LI can be accomplished by treating the alkyne with a base such as BuLi, LiHMDS, NaHMDS, KHMDS, LDA, KOtBu, or DBU in a solvent such as THF, diethyl ether, 1,2-dimethoxyethane, dichloromethane, DMF or mixtures thereof at temperatures between −100° C. and room temperature for a period between 15 min and 8 hrs for anion generation and then condensing the anion with the aldehyde compound in the same solvent at temperatures between −100° C. and room temperature for a period between 1 and 24 hrs.

Preferred conditions are anion generation with BuLi at −78° C. in THF for 30 min and subsequent condensation with the aldehyde component under the same conditions for 2 h.

Step B: Alkylation of alcohol LII can be accomplished by treatment with alkylating agents such as an alkyl bromide or alkyl iodide in the presence of a base such as $Ag_2O$, BuLi, LiHMDS, NaHMDS, KHMDS, LDA, KOtBu, or DBU in a solvent such as THF, diethyl ether, 1,2-dimethoxyethane, dichloromethane, DMF or mixtures thereof at temperatures between −100° C. and the reflux temperature of the solvent for a period between 1 and 24 hrs.

Preferred conditions are $Ag_2O$ in combination with an excess of alkyl iodide in the absence of additional solvent at 70° C. for 2 hours Step C: Reduction of the alkyne LIII can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Preferred conditions for Rid iodine, bromine or chlorine are hydrogenation in the presence of Pd/C as catalyst with EtOH as solvent.

Preferred conditions for $R^1$=iodine, bromine or chlorine are hydrogenation in the presence of $PtO_2$ as catalyst with THF or EtOAc as solvent.

Step D: Simultaneous cleavage of the amino alcohol protecting groups can be effected with a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are $CF_3COOH$ in aqueous acetonitrile at 80° C. for 4 hrs.

Step E: Cyclization of the amino alcohol to the corresponding 2-aminooxazoline can be accomplished by treatment with cyanogen bromide in THF as solvent and $K_2CO_3$ as base at r.t. overnight, or by treatment with cyanogen bromide in methanol as solvent and sodium acetate as base at 0° C. to r.t. overnight.

Scheme 17

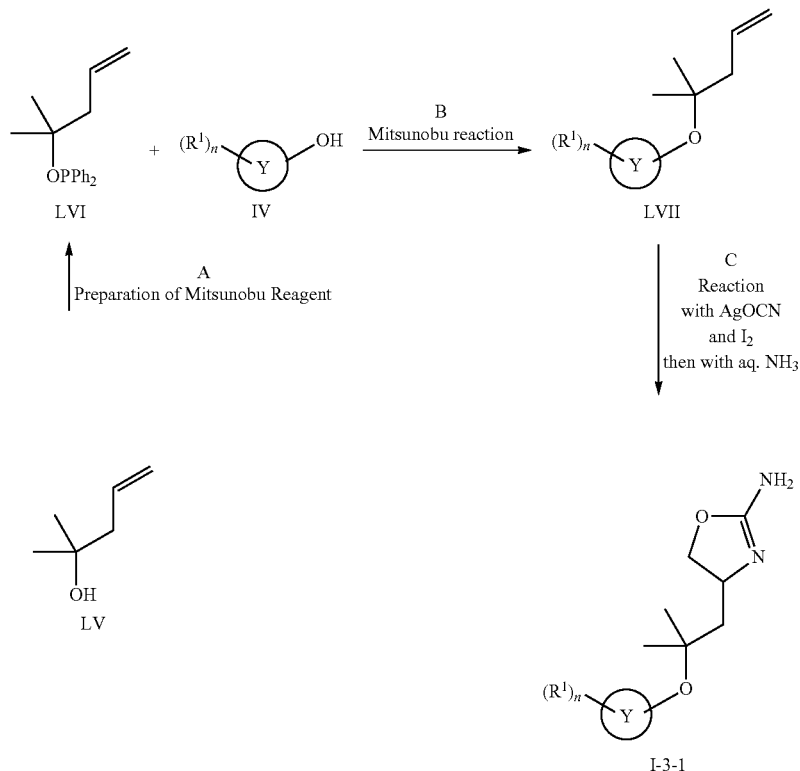

The substituents are as described above.

Step A: Preparation of the Mitsunobu reagent LVI from 2-methyl-pent-4-en-2-ol LV (CAS 624-97-5) can be accomplished by treatment with chlorodiphenylphosphine in the presence of a catalyst such as 4-dimethylaminopyridine and a base such as triethylamine in a solvent such as THF at room temperature as described in Tetrahedron 2003, 63, 6358-6364.

Step B: Mitsunobu reaction of phenol derivatives IV with the freshly prepared reagent LVI can be accomplished by using an activating agent such as 2,6-dimethylbenzoquinone in an inert solvent such as dichloroethane at temperatures from room temperature to 100° C. for 1-24 hrs as described in *J. Am. Chem. Soc.* 2004, 126(23), 7359-7367. Preferred conditions are 95° C. for 24 hours.

Step C: Amino-oxazioline ring formation can be accomplished by a two-step procedure comprising treatment of alkene LVII with silver cyanate and iodine in a solvent mixture such as ethyl acetate/acetonitrile at temperatures from 0° C. to room temperature for 1-18 hrs, followed by reaction with aqueous ammonia at room temperature.

Scheme 18

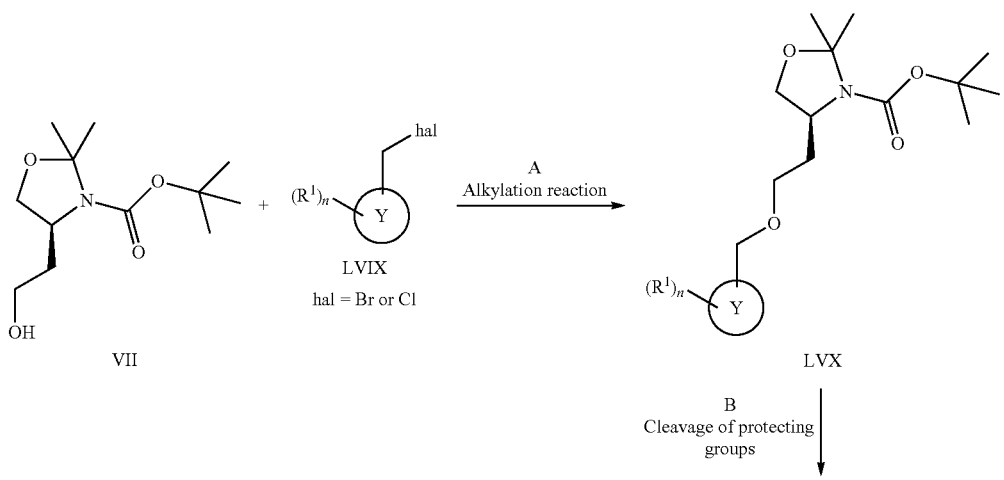

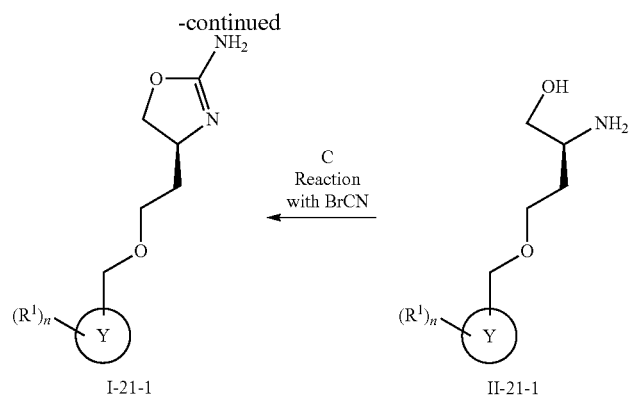

The substituents are as described above.

Step A: Alkylation of alcohol VII can be accomplished by treatment with benzyl halide derivative LVIX in the presence of a base such as Ag$_2$O, NaH, BuLi, LiHMDS, NaHMDS, KHMDS, LDA, KOtBu, or DBU in a solvent such as THF, diethyl ether, 1,2-dimethoxyethane, dichloromethane, DMF or mixtures thereof at temperatures between −100° C. and the reflux temperature of the solvent for a period between 1 and 24 hrs. Where the benzyl halide derivative LVIX is an benzyl bromide derivative, a catalyst such as tetrabutylammonium iodide may optionally be used. Preferred conditions are sodium hydride in combination with tetrabutylammonium iodide in THF at room temperature for 16 hours Step B: Simultaneous cleavage of the amino alcohol protecting groups can be effected with a mineral acid such as HCl, H$_2$SO$_4$ or H$_3$PO$_4$ or an organic acid such as CF$_3$COOH, CHCl$_2$COOH, HOAc or p-toluonesulfonic acid in a solvent such as CH$_3$CN, CH$_2$Cl$_2$, CHCl$_3$, THF, MeOH, EtOH or H$_2$O at 0 to 80° C. Preferred conditions are CF$_3$COOH in aqueous acetonitrile at 80° C. for 90 min.

Step C: Cyclization of the amino alcohol to the corresponding 2-aminooxazoline can be accomplished by treatment with cyanogen bromide in THF as solvent and K$_2$CO$_3$ as base at r.t. overnight, or by treatment with cyanogen bromide in methanol as solvent and sodium acetate as base at 0° C. to r.t. overnight.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thicklayer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1—TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1, 2,3,4-tetrahydro-1-naphthyl)-2-imidazoline bound in the presence of the appropriate unlabelled ligand (10 μM). Competing ligands were tested in a wide range of concentrations (10 μM-30 μM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a Ki value (μM) in mouse on TAAR1 in the range of <0.01 μM. Ki values for representative compounds of the invention are shown in the table below.

| Example | Ki (μM) mouse |
|---|---|
| 1 | 0.0017 |
| 2 | 0.0028 |
| 3 | 0.0005 |
| 4 | 0.0009 |
| 5 | 0.0003 |
| 6 | 0.0041 |
| 7 | 0.0032 |
| 8 | 0.0002 |
| 9 | 0.0012 |
| 10 | 0.0021 |
| 11 | 0.0011 |
| 13 | 0.0073 |
| 14 | 0.0056 |
| 17 | 0.0012 |
| 18 | 0.0026 |
| 19 | 0.0021 |
| 20 | 0.0025 |
| 21 | 0.0017 |
| 23 | 0.0031 |
| 24 | 0.0084 |
| 25 | 0.003 |
| 26 | 0.0007 |
| 27 | 0.0017 |
| 28 | 0.0013 |
| 30 | 0.0004 |
| 31 | 0.0005 |
| 32 | 0.0007 |
| 33 | 0.0018 |
| 34 | 0.0008 |
| 35 | 0.0001 |
| 36 | 0.0039 |
| 45 | 0.0028 |
| 47 | 0.0048 |
| 48 | 0.0016 |
| 54 | 0.0014 |
| 55 | 0.0025 |
| 57 | 0.0003 |
| 58 | 0.0041 |
| 59 | 0.0076 |
| 60 | 0.0025 |
| 61 | 0.0055 |
| 63 | 0.001 |
| 64 | 0.0076 |
| 67 | 0.0046 |
| 68 | 0.0012 |
| 69 | 0.008 |
| 70 | 0.0036 |
| 71 | 0.0024 |
| 72 | 0.0024 |
| 73 | 0.0021 |
| 74 | 0.004 |
| 75 | 0.001 |
| 77 | 0.0091 |
| 79 | 0.0086 |
| 81 | 0.0064 |
| 84 | 0.0076 |
| 85 | 0.0059 |
| 88 | 0.0048 |
| 89 | 0.0059 |
| 90 | 0.008 |
| 91 | 0.0006 |
| 96 | 0.0062 |
| 107 | 0.001 |
| 108 | 0.0014 |
| 109 | 0.0016 |
| 110 | 0.0059 |
| 111 | 0.001 |
| 112 | 0.0012 |
| 113 | 0.0037 |
| 114 | 0.0019 |
| 115 | 0.0031 |
| 116 | 0.0011 |
| 117 | 0.0032 |
| 119 | 0.0017 |
| 120 | 0.0014 |
| 121 | 0.0038 |
| 122 | 0.0007 |
| 123 | 0.0065 |
| 124 | 0.001 |
| 127 | 0.008 |
| 130 | 0.0007 |
| 136 | 0.0004 |
| 140 | 0.0009 |
| 141 | 0.0037 |
| 142 | 0.0013 |

-continued

| Example | Ki (µM) mouse |
|---|---|
| 143 | 0.0009 |
| 144 | 0.0005 |
| 150 | 0.0007 |
| 152 | 0.0029 |
| 153 | 0.0011 |
| 155 | 0.0032 |
| 156 | 0.0073 |
| 158 | 0.0011 |
| 159 | 0.0063 |
| 162 | 0.0022 |
| 172 | 0.0015 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment or prevention of depression, psychosis, Parkinson's disease, anxiety and attention deficit hyperactivity disorder (ADHD).

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

(S)-4-(2-Phenoxy-ethyl)-4,5-dihydro-oxazol-2-ylamine

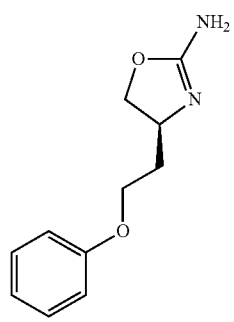 [SMILES: NC1=N[C@@H](CCOc2ccccc2)CO1]

a) (S)-2-tert-Butoxycarbonylamino-4-phenoxy-butyric acid methyl ester

To a stirred solution of (S)-(tert-butoxycarbonylamino)-4-hydroxybutyric acid methyl ester (1.43 g; CAS 120042-11-7)

in THF (4 ml) were added phenol (692 mg), triphenylphosphine (1.77 g) and diisopropyl azodicarboxylate (1.36 g). The resulting yellow solution was stirred at room temperature overnight. The reaction mixture was evaporated and purified by column chromatography (SiO₂; gradient: heptane/EtOAc 100:0->90:10) to give (S)-2-tert-butoxycarbonylamino-4-phenoxy-butyric acid methyl ester (1.16 g, 61%) as a light yellow oil. MS (ISP): 210.1 ([M+H-BOC]⁺)).

b) (S)-2-Amino-4-phenoxy-butyric acid methyl ester

To a solution of (S)-2-tert-butoxycarbonylamino-4-phenoxy-butyric acid methyl ester (1.15 g) in dichloromethane (3 ml) was added under an argon atmosphere trifluoroacetic acid (4.2 ml). The mixture was stirred for 16 h. The mixture was concentrated. The residue was treated with sodium bicarbonate solution until the pH was basic and extracted with dichloromethane twice. The combined organic layers were dried (MgSO₄) and evaporated. The product was used without purification for the next step, yellow oil. MS (ISP): 210.3 ([M+H]⁺)).

c) (S)-2-Amino-4-phenoxy-butan-1-ol

To a suspension of lithium aluminum hydride (282 mg) in tetrahydrofuran (4 ml) was added a solution of (S)-2-amino-4-phenoxy-butyric acid methyl ester (778 mg) in tetrahydrofuran (3 ml) and the mixture was stirred for 2 hours at 50° C. Sodium hydroxide solution (4N) was added until gas evolution ceased and the suspension was filtered through Celite. The solvent was evaporated and the residue was purified by chromatography (column: Isolute® Flash-NH₂ from Separtis; eluent: ethyl acetate/MeOH=98:2) to yield a colourless oil, (180 mg, 27%); MS (ISP): 182.3 ((M+H)⁺).

d) (S)-4-[2-2-Chloro-phenyl)-ethyl]-4-methyl-4,5-dihydro-oxazol-2-ylamine

To a stirred mixture of (S)-2-amino-4-phenoxy-butan-1-ol (175 mg) and K₂CO₃ (200 mg) in THF (5 ml) under an argon atmosphere was added a solution of cyanogen bromide (123 mg) in THF (1 ml). The mixture was stirred for 18 hours, then water and ethyl acetate were added. The organic layer was washed with water, dried over MgSO₄ and evaporated over Isolute® Flash-NH₂ silica gel. Chromatography (column: Isolute® Flash-NH₂ from Separtis; eluent: ethyl acetate/MeOH=95:5) yielded the title compound as a white solid, (62 mg, 31%); MS (ISP): 207.1 ((M+H)⁺).

EXAMPLE 2

(S)-4-[2-(4-Fluoro-phenoxy)-ethyl]-4,5-dihydro-oxazol-2-ylamine

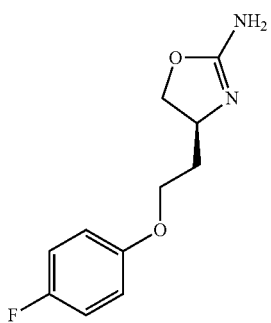 [SMILES: NC1=N[C@@H](CCOc2ccc(F)cc2)CO1]

The title compound was obtained in analogy to example 1 starting from 4-fluorophenol instead of phenol. Light brown oil. MS (ISP): 225.1 ([M+H]⁺)

EXAMPLE 3

(S)-4-[2-(4-Chloro-phenoxy)-ethyl]-4,5-dihydro-oxazol-2-ylamine

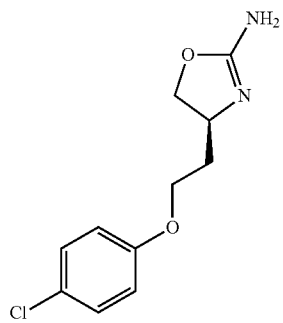 [SMILES: NC1=N[C@@H](CCOc2ccc(Cl)cc2)CO1]

a) (S)-4-[2-(4-Chloro-phenoxy)-ethyl]-2,2-dimethyl-oxazolidine-3-carboxylic acid tert-butyl ester To a stirred solution of tert-butyl (S)-4-(2-hydroxyethyl)-2,2-dimethyl-oxazolidine-3-carboxylate (411 mg; CAS 147959-18-0) in THF (6 ml) were added 4-chlorophenol (283 mg), triphenylphosphine (630 mg) and diethyl azodicarboxylate (40% in toluene, 0.92 ml). The resulting yellow solution was placed in a microwave oven at 100° C. for 20 min. Sodium hydroxide solution (1M) and ethyl acetate were added, after separation the organic layer was washed a second time with 1M sodium hydroxide solution, dried over magnesium sulphate and concentrated in vacuo. The crude product was purified by column chromatography (SiO₂; gradient: heptane/EtOAc 100:0->90:10) to give (S)-4-[2-(4-chloro-phenoxy)-ethyl]-2,2-dimethyl-oxazolidine-3-carboxylic acid tert-butyl ester (540 mg, 76%) as a light yellow oil. MS (ISP): 356.1 ([M+H]⁺)).

b) (S)-2-Amino-4-(4-chloro-phenoxy)-butan-1-ol

To (S)-4-[2-(4-chloro-phenoxy)-ethyl]-2,2-dimethyl-oxazolidine-3-carboxylic acid tert-butyl ester (530 mg) was added under an argon atmosphere 5.5 M HCl solution in ethanol (2 ml). The mixture was stirred for 16 h. The mixture was concentrated. The residue was dissolved in dichloromethane and an excess of ammonia in methanol and some silica gel was added. The solvents were evaporated and the crude product was purified by column chromatography (column: Isolute® Flash-NH₂ from Separtis; eluent: dichloromethane/methanol=90:10) to give (S)-2-amino-4-(4-chloro-phenoxy)-butan-1-ol (185 mg, 58%) as a white solid. MS (ISP): 216.3 ([M+H]⁺)).

c) (S)-4-[2-(4-Chloro-phenoxy)-ethyl]-4,5-dihydro-oxazol-2-ylamine

In analogy to example 1d (S)-2-amino-4-(4-chloro-phenoxy)-butan-1-ol was reacted with cyanogen bromide to give (S)-4-[2-(4-chloro-phenoxy)-ethyl]-4,5-dihydro-oxazol-2-ylamine. White solid. MS (ISP): 240.9 ([M+H]⁺))

EXAMPLE 4

(S)-4-[2-(3-Trifluoromethyl-phenoxy)-ethyl]-4,5-dihydro-oxazol-2-ylamine

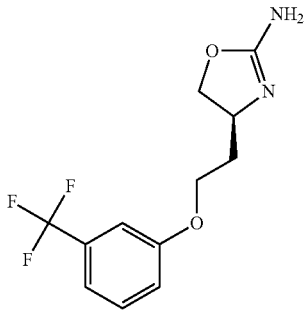 [SMILES: NC1=N[C@@H](CCOc2cccc(C(F)(F)F)c2)CO1]

The title compound was obtained in analogy to example 3 starting from 3-trifluoromethyl-phenol instead of 4-chlorophenol. Light brown oil. MS (ISP): 275.3 ([M+H]$^+$)

EXAMPLE 5

(S)-4-[2-(3-Chloro-phenoxy)-ethyl]-4,5-dihydro-oxazol-2-ylamine

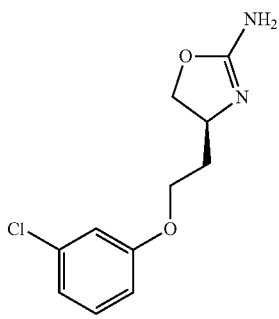 [SMILES: NC1=N[C@@H](CCOc2cccc(Cl)c2)CO1]

The title compound was obtained in analogy to example 3 starting from 3-chloro-phenol instead of 4-chlorophenol. Light yellow oil. MS (ISP): 241.4 ([M+H]$^+$)

EXAMPLE 6

(S)-4-[2-(2-Chloro-phenoxy)-ethyl]-4,5-dihydro-oxazol-2-ylamine

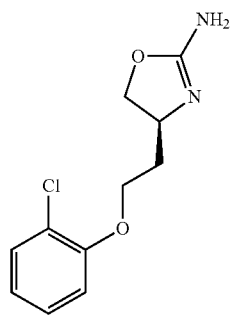 [SMILES: NC1=N[C@@H](CCOc2ccccc2Cl)CO1]

The title compound was obtained in analogy to example 3 starting from 2-chloro-phenol instead of 4-chlorophenol. Light yellow oil. MS (ISP): 241.4 ([M+H]$^+$)

EXAMPLE 7

(S)-4-(3-Methyl-3-phenyl-butyl)-4,5-dihydro-oxazol-2-ylamine

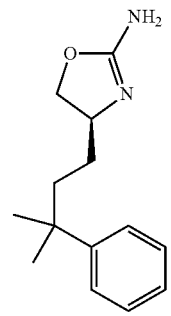 [SMILES: CC(C)(CC[C@H]1COC(N)=N1)c1ccccc1]

a) (S)-4-Methyl-benzenesulfinic acid [4-methyl-4-phenyl-pent-(E)-ylidene]-amide

To a stirred solution of (S)-(+)-p-toluenesulfinamide (1.89 g) in dichloromethane (10 ml) were added 4-methyl-4-phenyl-1-pentanal (1.65 g; CAS 120384-23-8) in dichloromethane (25 ml) and titanium(IV)-ethoxide (11.64 g). After stirring the mixture overnight it was cooled to 4° C. and water (50 ml) was added. The suspension was filtered through Celite. The solution was washed with sodium chloride solution, dried (MgSO$_4$) and concentrated. The crude product was purified by column chromatography (SiO$_2$; gradient: heptane/EtOAc 100:0->90:10) to give (S)-4-methyl-benzenesulfinic acid ((S)-1-cyano-4-methyl-4-phenyl-pentyl)-amide (1.29 g, 44%) as a light yellow oil which was used directly for the next step.

b) (S)-4-methyl-benzenesulfinic acid ((S)-1-cyano-4-methyl-4-phenyl-pentyl)-amide (S)-4-methyl-benzenesulfinic acid [4-methyl-4-phenyl-pent-(E)-ylidene]-amide (1.29 g) was dissolved in tetrahydrofuran (35 ml) and cooled to -78° C. In a second flask diethylaluminium cyanide solution (1N in toluene, 9.5 ml) was diluted with tetrahydrofuran (35 ml). After cooling down to -78° C. isopropanol (0.31 ml) was added and the mixture was stirred additional 30 min at room temperature. This mixture was added slowly to the imine solution in the first flask at -78° C. and stirred overnight while warming up to room temperature. After cooling down to -78° C. saturated ammonium chloride solution (18 ml) was added. The suspension was filtered through Celite. Ethyl acetate was added and the solution was washed with sodium chloride solution, dried (MgSO$_4$) and concentrated. The crude product was purified by column chromatography (SiO$_2$; heptane/EtOAc 4:1) to give (S)-4-methyl-benzenesulfinic acid ((S)-1-cyano-4-methyl-4-phenyl-pentyl)-amide (0.6 g, 43%) as a light yellow oil.

c) (S)-2-Amino-5-methyl-5-phenyl-hexanoic acid ethyl ester

To (S)-4-methyl-benzenesulfinic acid ((S)-1-cyano-4-methyl-4-phenyl-pentyl)-amide (600 mg) was added under an argon atmosphere 5.5 M HCl solution in ethanol (50 ml). The mixture was refluxed for 4 h. The mixture was concentrated, water was added and the mixture was brought to neutral pH by adding aqueous ammonia. The mixture was extracted with ethyl acetate. The combined organic layers were dried (MgSO$_4$) and evaporated. The crude product was purified by column chromatography (SiO$_2$; heptane/ethyl acetate=4:1) to give (S)-2-amino-5-methyl-5-phenyl-hexanoic acid ethyl ester (280 mg, 63%) as a light yellow liquid. MS (ISP): 250.2 ([M+H]$^+$)).

d) (S)-2-Amino-5-methyl-5-phenyl-hexan-1-ol

To a suspension of lithium aluminum hydride (68 mg) in tetrahydrofuran (3 ml) was added a solution of (S)-2-amino-5-methyl-5-phenyl-hexanoic acid ethyl ester (280 mg) in tetrahydrofuran (1 ml) and the mixture was stirred for 3 hours at room temperature. Sodium sulphate solution (1N) was added until gas evolution ceased and the suspension was filtered through Celite. The solvent was evaporated and the residue was purified by chromatography (column: Isolute® Flash-NH$_2$ from Separtis; eluent: dichloromethane/MeOH=90:10) to yield a light yellow oil, (122 mg, 52%); MS (ISP): 208.2 ((M+H)$^+$).

e) (S)-4-(3-Methyl-3-phenyl-butyl)-4,5-dihydro-oxazol-2-ylamine

In analogy to example 1d (S)-2-amino-5-methyl-5-phenyl-hexan-1-ol was reacted with cyanogen bromide to give (S)-4-(3-methyl-3-phenyl-butyl)-4,5-dihydro-oxazol-2-ylamine. White solid. MS (ISP): 233.1 ([M+H]$^+$))

EXAMPLE 8

(S)-4-[2-(3-Chloro-4-fluoro-phenoxy)-ethyl]-4,5-dihydro-oxazol-2-ylamine

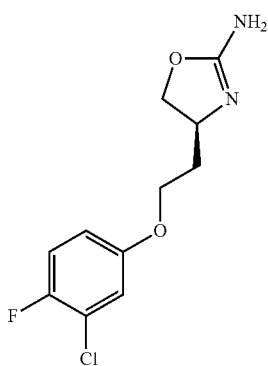 [SMILES: NC1=N[C@@H](CCOc2ccc(F)c(Cl)c2)CO1]

The title compound was obtained in analogy to example 3 starting from 3-chloro-4-fluoro-phenol instead of 4-chlorophenol. Light yellow solid. MS (ISP): 258.8 ([M+H]$^+$)

EXAMPLE 9

(S)-4-[2-(3,4-Difluoro-phenoxy)-ethyl]-4,5-dihydro-oxazol-2-ylamine

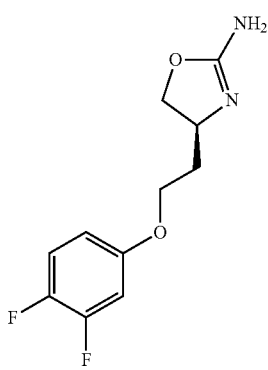 [SMILES: NC1=N[C@@H](CCOc2ccc(F)c(F)c2)CO1]

The title compound was obtained in analogy to example 3 starting from 3,4-difluoro-phenol instead of 4-chlorophenol. Light yellow solid. MS (ISP): 243.1 ([M+H]$^+$)

EXAMPLE 10

(S)-4-[2-(2-Chloro-4-fluoro-phenoxy)-ethyl]-4,5-dihydro-oxazol-2-ylamine

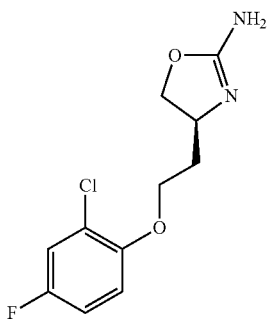 [SMILES: NC1=N[C@@H](CCOc2ccc(F)cc2Cl)CO1]

The title compound was obtained in analogy to example 3 starting from 2-chloro-4-fluoro-phenol instead of 4-chlorophenol. White solid. MS (ISP): 259.1 ([M+H]$^+$)

EXAMPLE 11

(S)-4-[2-(2,4-Difluoro-phenoxy)-ethyl]-4,5-dihydro-oxazol-2-ylamine

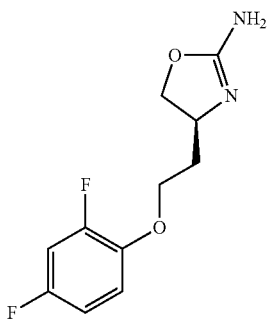

The title compound was obtained in analogy to example 3 starting from 2,4-difluoro-phenol instead of 4-chlorophenol. White solid. MS (ISP): 243.3 ([M+H]$^+$)

EXAMPLE 12

(4S)-4-(4,4,4-Trifluoro-3-phenyl-butyl)-4,5-dihydro-oxazol-2-ylamine

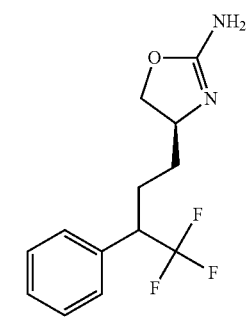 [SMILES: NC1=N[C@@H](CCC(c2ccccc2)C(F)(F)F)CO1]

a) rac-(3-Iodo-1-trifluoromethyl-propyl)-benzene

To a stirred solution of triphenylphosphine (3.93 g) and imidazole (1.02 g) in dichloromethane (20 ml) under an argon atmosphere was added slowly iodine (3.81 g) and rac-4,4,4-trifluoro-3-phenyl-butan-1-ol (2.04 g, CAS 65948-16-5). The mixture was stirred for 2 hours at room temperature, then dichloromethane (50 ml) was added and mixture was extracted with saturated sodium thiosulfate solution (50 ml) and hydrochloric acid (1N, 25 ml). The organic layer was dried over MgSO$_4$ and evaporated. The residue was suspended in ether and filtered to remove insoluble triphenylphosphine oxide. The ether was evaporated and the residue was purified by column chromatography (SiO$_2$, heptane/EtOAc=9:1) to yield a light yellow liquid, (1.99 g, 63%).

b) (2R,5S)-2-Isopropyl-3,6-dimethoxy-5-(4,4,4-trifluoro-3-phenyl-butyl)-2,5-dihydro-pyrazine A solution of (R)-(−)-2,5-dihydro-3,6-dimethoxy-2-isopropylpyrazine (1.1 g) in tetrahydrofuran (25 ml) was cooled to −70° C., then tert.butyllithium (1.7 M in pentane, 3.88 ml) was added and the mixture was stirred for 1 hour. A solution of (3-iodo-1-trifluoromethylpropyl)-benzene (1.98 g) in tetrahydrofuran (7 ml) was added slowly and the mixture was stirred overnight at −70° C. At room temperature saturated ammonium chloride solution was added and the mixture was extracted three times with ether. The combined organic layers were dried (MgSO$_4$), filtered and evaporated. The residue was purified by column chromatography (SiO$_2$, heptane/EtOAc=9:1 to yield a yellow liquid, (1.86 g, 83%).

c) (S)-2-Amino-6,6,6-trifluoro-5-phenyl-hexanoic acid methyl ester

To a solution of (2R,5S)-2-isopropyl-3,6-dimethoxy-5-(4,4,4-trifluoro-3-phenyl-butyl)-2,5-dihydro-pyrazine (1.86 g) in acetonitrile (18 ml) were added water (7 ml) and trifluoroacetic acid (3.8 ml). The mixture was stirred overnight at 40° C. Saturated ammonium chloride solution was added and the mixture was extracted with dichloromethane three times. The combined organic layers were dried (MgSO$_4$), filtered and evaporated. The residue was purified by column chromatography (SiO$_2$, EtOAc/MeOH=98:2 to yield a light yellow solid, (0.98 g, 71%); MS (ISP): 276.1 ((M+H)$^+$).

d) (S)-2-Amino-6,6,6-trifluoro-5-phenyl-hexan-1-ol

To a suspension of lithium aluminum hydride (0.267 g) in tetrahydrofuran (30 ml) was added a solution of (S)-2-amino-6,6,6-trifluoro-5-phenyl-hexanoic acid methyl ester (0.97 g) in tetrahydrofuran (3 ml) and the mixture was stirred for 2 hours at 50° C. Sodium sulphate solution (2M, 0.3 ml) was added and the mixture was filtered through Celite. The solvent was evaporated and the residue was purified by chromatography (column: Isolute® Flash-NH$_2$ from Separtis; eluent: ethyl acetate/MeOH=98:2) to yield a light yellow liquid, (0.50 g, 57%) MS (ISP): 248.1 ((M+H)

e) (4S)-4-(4,4,4-Trifluoro-3-phenyl-butyl)-4,5-dihydro-oxazol-2-ylamine

In analogy to example 1d (S)-2-amino-6,6,6-trifluoro-5-phenyl-hexan-1-ol was reacted with cyanogen bromide to give (4S)-4-(4,4,4-trifluoro-3-phenyl-butyl)-4,5-dihydro-oxazol-2-ylamine. White solid. MS (ISP): 273.1 ([M+H]$^+$))

EXAMPLE 13

(4S)-4-(3-Phenyl-butyl)-4,5-dihydro-oxazol-2-ylamine

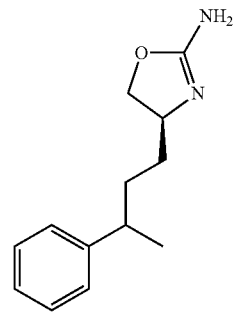 [SMILES: CC(CC[C@H]1COC(N)=N1)c1ccccc1]

a) (4S)-2,2-Dimethyl-4-((E)-3-phenyl-but-2-enyl)-oxazolidine-3-carboxylic acid tert-butyl ester To a stirred solution of N,N-diisopropylamine (1.74 ml) in tetrahydrofuran (8 ml) at −78° C. was added dropwise a solution of n-butyllithium (7.71 ml, 1.6 M in hexane) and the reaction mixture was then warmed to 0° C. for 15 min. After re-cooling to −78° C., a solution of diethyl 1-phenylethyl phosphonate (2.76 ml) in tetrahydrofuran (8 ml) was added dropwise. The mixture was stirred at −78° C. for 30 min and then a solution of (S)-2,2-dimethyl-4-(2-oxo-ethyl)oxazolidine-3-carboxylic acid tert-butyl ester (2.00 g, CAS 147959-19-1) in tetrahydrofuran (8 ml) was added dropwise over 20 min. The mixture was then allowed to warm to room temparature and stirring continued at room temperature for 48 hours. The mixture was then quenched by addition of aqueous hydrochloric acid (2N) and then made basic by addion of aqueous sodium hydroxide solution (1N). The mixture was taken up in ethyl acetate and the phases separated. The organic layer was washed sequentially with water and with saturated brine, dried over Na$_2$SO$_4$ and concentrated in vacuo. The residue was purified by column chromatography (SiO$_2$, heptane/EtOAc gradient) to yield a yellow oil, (1.16 g, 44%); MS (ISP): 332.1 ([M+H]$^+$).

b) (E)-(2S)-2-Amino-5-phenyl-hex-4-en-1-ol

To a stirred solution of (4S)-2,2-dimethyl-4-((E)-3-phenyl-but-2-enyl)-oxazolidine-3-carboxylic acid tert-butyl ester (1.15 g) in dioxane (10 ml) at room temperature was added a 4 M solution of hydrogen chloride in dioxane (17.4 ml solution) and stirring was continued at room temperature overnight. The mixture was taken up in ethyl acetate and washed sequentially with aqueous sodium hydroxide solution (1N), water and saturated brine. The organic layer was dried over Na$_2$SO$_4$ and concentrated in vacuo. The residue was purified by column chromatography (SiO$_2$, heptane/dichloromethane gradient; eluant containing 1% aq. ammonia) to yield a yellow oil, (185 mg, 28%); MS (ISP): 192.1 ([M+H]$^+$).

c) (2S)-2-Amino-5-phenyl-hexan-1-ol

To a solution of (E)-(2S)-2-amino-5-phenyl-hex-4-en-1-ol (180 mg) in methanol (25 ml) at room temperature was added 10% palladium on charcoal (50 mg). The mixture was stirred under an atmosphere of hydrogen (1 atm) at room temperature for 2 h. The catalyst was removed by filtration and the filtrate was concentrated in vacuo to yield a colourless oil, (160 mg, 88%); MS (ISP): 194.3 ([M+H]$^+$).

d) (4S)-4-(3-Phenyl-butyl)-4,5-dihydro-oxazol-2-ylamine

To a stirred solution of (2S)-2-amino-5-phenyl-hexan-1-ol (160 mg) in methanol (11 ml) at room temperature was added sodium acetate (136 mg). The mixture was cooled to 0° C. and a solution of cyanogen bromide (96 mg) in methanol (2 ml) was added dropwise. The mixture was stirred at 0° C. for 30 min and then at room temperature overnight before being concentrated in vacuo. The residue was resuspended in tetrahydrofuran/ethyl acetate (1/2) and washed sequentially with saturated aqueous sodium bicarbonate solution and saturated brine. The organic layer was dried over $Na_2SO_4$ and concentrated in vacuo. The residue was purified by column chromatography ($SiO_2$, heptane/dichloromethane/methanol gradient; eluant containing 1% aq. ammonia) to yield a colourless oil, (128 mg, 71%); MS (ISP): 219.2 ([M+H]$^+$).

EXAMPLE 14

(4S)-4-(3-Phenyl-pentyl)-4,5-dihydro-oxazol-2-ylamine

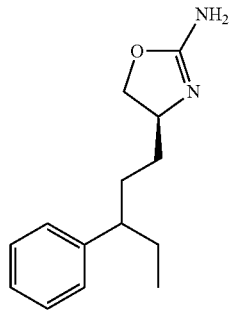 [SMILES: CCC(CC[C@H]1COC(N)=N1)c1ccccc1]

The title compound was obtained in analogy to example 13 starting from (1-phenylpropyl)-phosphonic acid diethyl ester. White solid. MS (ISP): 233.1 ([M+H]$^+$).

EXAMPLE 15

(4S)-4-(2-Methyl-3-phenyl-propyl)-4,5-dihydro-oxazol-2-ylamine

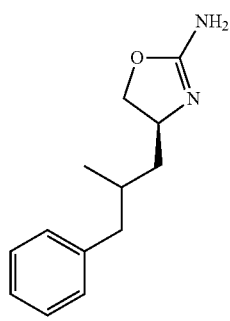 [SMILES: CC(Cc1ccccc1)C[C@H]1COC(N)=N1]

The title compound was obtained in analogy to example 12 starting from 2-methyl-3-phenyl-propan-1-ol instead of 4,4,4-trifluoro-3-phenyl-butan-1-ol. Light yellow solid. MS (ISP): 219.2 ([M+H]$^+$).

EXAMPLE 16

(4S)-4-(2-Phenoxy-propyl)-4,5-dihydro-oxazol-2-ylamine

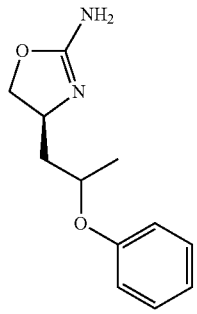 [SMILES: CC(C[C@H]1COC(N)=N1)Oc1ccccc1]

The title compound was obtained in analogy to example 12 starting from 2-phenoxypropan-1-ol instead of 4,4,4-trifluoro-3-phenyl-butan-1-ol. Light yellow oil. MS (ISP): 221.3 ([M+H]$^+$).

EXAMPLE 17

(4S)-4-[3-(4-Fluoro-phenyl)-butyl]-4,5-dihydro-oxazol-2-ylamine

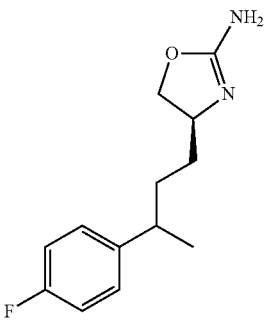

a) Rac-[1-(4-Fluoro-phenyl)-ethyl]-phosphonic acid diethyl ester

To a stirred solution of diethyl (4-fluoro-benzyl)phopshonate (5.3 g) in tetrahydrofuran (15 ml) at 0° C. was added dropwise a solution of methylmagnesium chloride (11.5 ml, 3 M in tetrahydrofuran) and the reaction mixture was then stirred at 0° C. for 30 min and then at room temperature for a further 30 min. After re-cooling to 0° C., a solution of dimethyl sulphate (2.25 ml) in tetrahydrofuran (5 ml) was added dropwise. The mixture was stirred at room temperature for 2.5 h and then the mixture was quenched by dropwise addition of aqueous hydrochloric acid (2N) followed by addition of aqueous hydrochloric acid (5N). The mixture was taken up in ethyl acetate and the phases separated. The organic layer was washed sequentially with water and with saturated brine, dried over $Na_2SO_4$ and concentrated in vacuo. The residue was purified by column chromatography (SiO$_2$, heptane/EtOAc gradient) to yield a colourless oil, (2.00 g, 36%); MS (ISP): 261.1 ([M+H]$^+$).

(b) (4S)-4-[3-(4-Fluoro-phenyl)-butyl]-4,5-dihydro-oxazol-2-ylamine

The title compound was obtained in analogy to the sequence of example 13 starting from rac-[1-(4-fluoro-phenyl)-ethyl]-phosphonic acid diethyl ester. Colourless oil. MS (ISP): 237.3 ([M+H]$^+$).

EXAMPLE 18

(4S)-4-[3-(4-Fluoro-phenyl)-pentyl]-4,5-dihydro-oxazol-2-ylamine

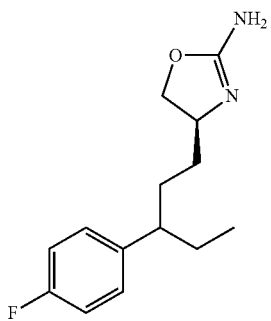 [SMILES: CCC(CC[C@H]1COC(N)=N1)c1ccc(F)cc1]

a) Rac [1-(4-Fluoro-phenyl)-propyl]-phosphonic acid diethyl ester

The title compound was obtained in analogy to the sequence of example 17(a) starting from diethyl (4-fluoro-benzyl)phopshonate and diethyl sulphate. Colourless oil. MS (ISP): 275.2 ([M+H]$^+$).

(b) (4S)-4-[3-(4-Fluoro-phenyl)-pentyl]-4,5-dihydro-oxazol-2-ylamine

The title compound was obtained in analogy to the sequence of example 13 starting from rac-[1-(4-fluoro-phenyl)-ethyl]-phosphonic acid diethyl ester. Colourless oil. MS (ISP): 251.2 ([M+H]$^+$).

EXAMPLE 19

(S)-4-[2-(3-Trifluoromethoxy-phenoxy)-ethyl]-4,5-dihydro-oxazol-2-ylamine

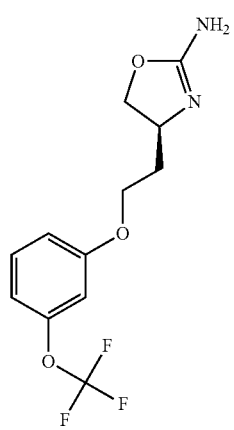 [SMILES: NC1=N[C@@H](CCOc2cccc(OC(F)(F)F)c2)CO1]

The title compound was obtained in analogy to example 3 starting from 3-trifluoromethoxy-phenol instead of 4-chlorophenol. Colourless oil. MS (ISP): 291.2 ([M+H]$^+$).

EXAMPLE 20

(S)-4-[2-(3-Methoxy-phenoxy)-ethyl]-4,5-dihydro-oxazol-2-ylamine

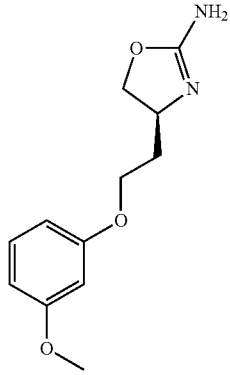 [SMILES: COc1cccc(OCC[C@H]2COC(N)=N2)c1]

The title compound was obtained in analogy to example 3 starting from 3-methoxyphenol instead of 4-chlorophenol. Colourless oil. MS (ISP): 237.1 ([M+H]$^+$).

EXAMPLE 21

(S)-4-[2-(3-Isopropyl-phenoxy)-ethyl]-4,5-dihydro-oxazol-2-ylamine

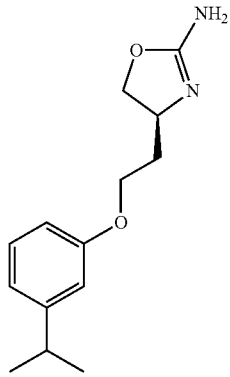 [SMILES: CC(C)c1cccc(OCC[C@H]2COC(N)=N2)c1]

The title compound was obtained in analogy to example 3 starting from 3-isopropylphenol instead of 4-chlorophenol. Colourless oil. MS (ISP): 249.3 ([M+H]$^+$)

EXAMPLE 22

(4S)-4-Methyl-4-(3-phenyl-butyl)-4,5-dihydro-oxazol-2-ylamine

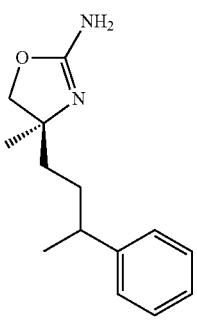 [SMILES: CC(CC[C@@]1(C)COC(N)=N1)c1ccccc1]

The title compound was obtained in analogy to example 12 starting from 3-phenyl-butan-1-ol instead of 4,4,4-trifluoro-3-phenyl-butan-1-ol in step a) and (R)-(−)-2,5-dihydro-3,6-dimethoxy-2-isopropyl-5-methylpyrazine instead of (R)-(−)-2,5-dihydro-3,6-dimethoxy-2-isopropylpyrazine in step b). Colourless oil. MS (ISP): 232.9 ([M+H]⁺).

EXAMPLE 23

(4S)-4-(2-Phenyl-cyclopropylmethyl)-4,5-dihydro-oxazol-2-ylamine

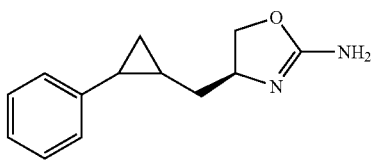 [SMILES: NC1=N[C@@H](CC2CC2c2ccccc2)CO1]

The title compound was obtained in analogy to example 12 starting from 2-phenylcyclopropanemethanol instead of 4,4,4-trifluoro-3-phenyl-butan-1-ol in step a). White solid. MS (ISP): 217.3 ([M+H]⁺).

EXAMPLE 24

(4S)-4-(1-Phenyl-ethoxymethyl)-4,5-dihydro-oxazol-2-ylamine

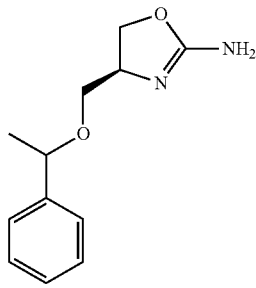 [SMILES: CC(OC[C@H]1COC(N)=N1)c1ccccc1]

a) (S)-2-Benzyloxycarbonylamino-3-(1-phenyl-ethoxy)-propionic acid methyl ester

To a stirred solution of 1-benzyl 2-methyl (S)-(−)-1,2-aziridinedicarboxylate (1.88 g) in dichloromethane (30 ml) were added at 0° C. 1-phenyl-ethanol (9.77 g) and boron trifluoride etherate (2.0 ml). After stirring the mixture for one hour the cooling bath was removed and stirring was continued overnight. Then the reaction mixture was poured onto saturated sodium bicarbonate solution and extracted with ethyl acetate. The combined organic layers were washed with brine, dried (MgSO₄) and concentrated. The crude product was purified by column chromatography (SiO₂; gradient: heptane/EtOAc 100:0->90:10) to give S)-2-benzyloxycarbonylamino-3-(1-phenyl-ethoxy)-propionic acid methyl ester (1.34 g, 47%) as a light yellow oil. MS (ISP): 358.2 ([M+H]⁺)).

b) (S)-2-Amino-3-(1-phenyl-ethoxy)-propionic acid methyl ester

To a solution of (S)-2-benzyloxycarbonylamino-3-(1-phenyl-ethoxy)-propionic acid methyl ester (1.1 g) in methanol (5 ml) were added ammonia in methanol (7 N solution, 0.22 ml) and palladium on charcoal (5%, 110 mg). The mixture was stirred vigorously under an atmosphere of hydrogen for 30 min. The catalyst was filtered off and the filtrate was evaporated. The crude product was purified by column chromatography (SiO₂; dichloromethane/MeOH=98:2) to give (R)-2-amino-3-(1-phenyl-ethoxy)-propan-1-ol (280 mg, 86%) as a light yellow liquid. MS (ISP): 224.2 ([M+H]⁺)).

c) (R)-2-Amino-3-(1-phenyl-ethoxy)-propan-1-ol

To a suspension of lithium aluminum hydride (212 mg) in tetrahydrofuran (5 ml) was added a solution of (S)-2-amino-3-(1-phenyl-ethoxy)-propionic acid methyl ester (280 mg) in tetrahydrofuran (5 ml) and the mixture was stirred for 2 hours at room temperature. Sodium hydroxide solution (4N) was added until gas evolution ceased, ether was added and the suspension was filtered through Celite. The solvent was evaporated and the residue was purified by chromatography (column: Isolute® Flash-NH₂ from Separtis; eluent: dichloromethane/MeOH=90:10) to yield a light yellow liquid, (130 mg, 24%); MS (ISP): 196.1 ((M+H)⁺).

d) (4S)-4-(1-Phenyl-ethoxymethyl)-4,5-dihydro-oxazol-2-ylamine

In analogy to example 1d (R)-2-amino-3-(1-phenyl-ethoxy)-propan-1-ol was reacted with cyanogen bromide to give (4S)-4-(1-phenyl-ethoxymethyl)-4,5-dihydro-oxazol-2-ylamine. Light yellow oil. MS (ISP): 221.3 ([M+H]⁺)).

EXAMPLE 25

(S)-4-[3-(4-Fluoro-phenyl)-3-methyl-butyl]-4,5-dihydro-oxazol-2-ylamine

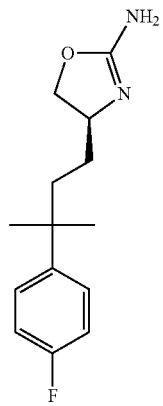

a) 2-(4-Fluoro-phenyl)-2-methyl-propionaldehyde

To a stirred solution of oxalyl chloride (2.81 ml) in dichloromethane (30 ml) at −60° C. was added dropwise a solution of dry dimethyl sulphoxide (4.84 ml) in dichloromethane (20 ml). The mixture was stirred for 15 min at −60° C. and then a solution of 2-(4-fluoro-phenyl)-2-methyl-propan-1-ol (4.59 g; CAS 703-10-6) in dichloromethane (20 ml) was added dropwise. The mixture was stirred at −60° C. for 2 hours and then triethylamine (18.9 ml) was added dropwise. The reaction mixture was allowed to warm to room temperature and diluted with water and with dichloromethane. The phases were separated and the organic phase was washed with water and then dried over Na₂SO₄ and concentrated in vacuo. The residue was purified by column chromatography (SiO₂, heptane/EtOAc gradient) to yield a colourless oil, (3.47 g, 77%).

b) (E)-4-(4-Fluoro-phenyl)-4-methyl-pent-2-enoic acid ethyl ester

To a stirred solution of triethyl phosphonoacetate (4.58 ml) in tetrahydrofuran (30 ml) was added portionwise sodium hydride (1.00 g, 60% dispersion in oil). The mixture was stirred for 1 hour at room temperature and then a solution of 2-(4-fluoro-phenyl)-2-methyl-propionaldehyde (3.46 g) in tetrahydrofuran (10 ml) was added dropwise at 0° C. The reaction mixture was allowed to warm to room temperature and stirred for 1 day. The mixture was then acidified by addition of 1 M aq. hydrochloric acid and taken up in ethyl acetate. The mixture was washed sequentially with water and with saturated brine, then dried over $Na_2SO_4$ and concentrated in vacuo. The residue was purified by column chromatography ($SiO_2$, heptane/EtOAc gradient) to yield a colourless oil, (4.14 g, 84%); MS (ISP): 237.3 ([M+H]$^+$).

c) 4-(4-Fluoro-phenyl)-4-methyl-pentanoic acid ethyl ester

To a solution of (E)-4-(4-fluoro-phenyl)-4-methyl-pent-2-enoic acid ethyl ester (4.10 g) in methanol (150 ml) at room temperature was added platinum(IV) oxide (788 mg). The mixture was stirred under an atmosphere of hydrogen (1 atm) at room temperature for 2 h. The catalyst was removed by filtration and the filtrate was concentrated in vacuo to yield a yellow oil, (3.97 g, 96%); MS (ISP): 239.2 ([M+H]$^+$).

d) 4-(4-Fluoro-phenyl)-4-methyl-pentanoic acid methoxy-methyl-amide

To a stirred solution of 4-(4-fluoro-phenyl)-4-methyl-pentanoic acid ethyl ester (3.97 g) and N,O-dimethylhydroxylamine hydrochloride (2.44 g) in tetrahydrofuran (40 ml) at −18° C. was added dropwise a solution of isopropylmagnesium chloride (25.0 ml, 2 M solution in THF). The mixture was stirred for 30 min at −15° C. and then quenched by addition of saturated ammonium chloride solution. The mixture was then acidified to pH 1 by addition of 1 M aq. hydrochloric acid and taken up in ethyl acetate. The mixture was washed sequentially with water and with saturated brine, then dried over $Na_2SO_4$ and concentrated in vacuo. The residue was purified by column chromatography ($SiO_2$, heptane/EtOAc gradient) to yield a colourless oil, (3.91 g, 93%); MS (ISP): 254.2 ([M+H]$^+$).

e) 4-(4-Fluoro-phenyl)-4-methyl-pentanal

To a solution of 4-(4-fluoro-phenyl)-4-methyl-pentanoic acid methoxy-methyl-amide (3.90 g) in tetrahydrofuran (70 ml) at −30° C. was added dropwise over 10 min a suspension of lithium aluminum hydride in tetrahydrofuran (15.4 ml, 1 M suspension). The mixture was stirred for a further 30 min at −30° C. and then cooled to −78° C. The mixture was quenched by dropwise addition of acetone (25 ml) and the mixture was then allowed to warm to room temperature. The mixture was then diluted with water and taken up in ethyl acetate. The mixture was washed sequentially with 1 N aq. hydrochloric acid and with saturated brine, then dried over $Na_2SO_4$ and concentrated in vacuo. The residue was purified by column chromatography ($SiO_2$, heptane/EtOAc gradient) to yield a colourless oil, (1.62 g, 54%).

f) (S)-4-[3-(4-Fluoro-phenyl)-3-methyl-butyl]-4,5-dihydro-oxazol-2-ylamine

The title compound was obtained in analogy to the sequence of example 7 starting from 4-(4-fluoro-phenyl)-4-methyl-pentanal. Colourless oil. MS (ISP): 251.2 ([M+H]$^+$)

EXAMPLE 26

(S)-4-[3-(4-Chloro-phenyl)-3-methyl-butyl]-4,5-dihydro-oxazol-2-ylamine

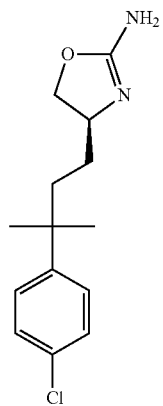 [SMILES: CC(C)(CC[C@H]1COC(N)=N1)c1ccc(Cl)cc1]

The title compound was obtained in analogy to the sequence of example 25 starting from of 2-(4-chloro-phenyl)-2-methyl-propan-1-ol (CAS 80854-14-4). Colourless oil. MS (ISP): 269.2 ([{$^{37}$Cl}M+H]$^+$), 267.2 ([{$^{35}$Cl}M+H]$^+$).

EXAMPLE 27

(4S)-4-[3-(4-Chloro-phenyl)-pentyl]-4,5-dihydro-oxazol-2-ylamine

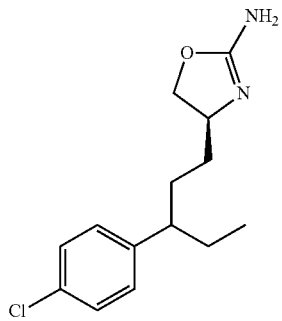 [SMILES: CCC(CC[C@H]1COC(N)=N1)c1ccc(Cl)cc1]

a) Rac-[1-(4-Chloro-phenyl)-propyl]-phosphonic acid diethyl ester

The title compound was obtained in analogy to example 17(a) starting from diethyl (4-chloro-benzyl)phopshonate and diethyl sulphate. Colourless oil. MS (ISP): 293.1 ([{$^{37}$Cl}M+H]$^+$), 291.1 ([{$^{35}$Cl}M+H]$^+$).

(b) (4S)-4-[3-(4-chloro-phenyl)-pentyl]-4,5-dihydro-oxazol-2-ylamine

The title compound was obtained in analogy to the sequence of example 13 starting from rac-[1-(4-chloro-phenyl)-propyl]-phosphonic acid diethyl ester, except that platinum(IV) oxide was used in place of palladium on charcoal

69 during the hydrogenation step. Colourless oil. MS (ISP): 269.2 ([{$^{37}$Cl}M+H]$^+$), 267.2 ([{$^{35}$Cl}M+H]$^+$).

EXAMPLE 28

(4S)-4-[3-(3-Trifluoromethyl-phenyl)-pentyl]-4,5-dihydro-oxazol-2-ylamine

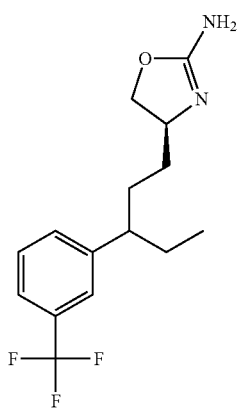 [SMILES: CCC(CC[C@H]1COC(N)=N1)c1cccc(C(F)(F)F)c1]

a) Rac-[1-(3-Trifluoromethyl-phenyl)-propyl]-phosphonic acid diethyl ester

The title compound was obtained in analogy to example 17(a) starting from diethyl 3-(trifluoromethyl)-benzylphosphonate and diethyl sulphate. Colourless oil. MS (ISP): 325.4 ([M+H]$^+$)

(b) (4S)-4-[3-(3-Trifluoromethyl-phenyl)-pentyl]-4,5-dihydro-oxazol-2-ylamine

The title compound was obtained in analogy to the sequence of example 13 starting from rac-[1-(3-trifluoromethyl-phenyl)-propyl]-phosphonic acid diethyl ester. Colourless oil. MS (ISP): 301.4 ([M+H]$^+$)

EXAMPLE 29

(RS)-4-Methyl-4-(2-phenoxy-ethyl)-4,5-dihydro-oxazol-2-ylamine

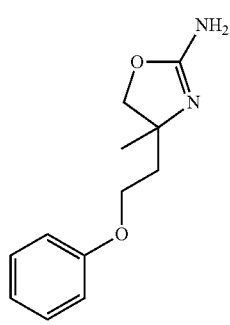 [SMILES: CC1(CCOc2ccccc2)COC(N)=N1]

a) (3-Methyl-but-3-enyloxy)-benzene

To a stirred solution of 3-methyl-3-buten-1-ol (1.17 ml) in tetrahydrofuran (30 ml) were added sequentially phenol (1.32 g), triphenylphosphine (3.85 g) and di-tert-butyl azodicarboxylate (3.27 g). The mixture was heated at 70° C. overnight and then was concentrated in vacuo. The residue was purified by column chromatography (SiO$_2$; gradient: heptane/EtOAc 100:0->70:30) to give (3-methyl-but-3-enyloxy)-benzene (2.06 g, quant.) as a colourless semi-solid which crystallized on standing.

(b) (RS)-4-Methyl-4-(2-phenoxy-ethyl)-4,5-dihydro-oxazol-2-ylamine

To a stirred solution of (3-methyl-but-3-enyloxy)-benzene (0.50 g) in ethyl acetate (18.5 ml) and acetonitrile (12.3 ml) was added silver cyanate (0.52 g). The resulting suspension was cooled to 0° C. and then a solution of iodine (0.94 g) in ethyl acetate (12.3 ml) was added dropwise. The reaction mixture was allowed to warm to room temperature overnight and was then filtered through decalite and the filter washed with ethyl acetate. The filtrate was treated with aqueous ammonia solution (15 ml, 25% solution) and the resulting mixture was stirred overnight at room temperature. The mixture was diluted with water and extracted twice with ethyl acetate. The combined organic phases were dried over Na$_2$SO$_4$ and concentrated in vacuo. The residue was purified by chromatography (column: Isolute® Flash-NH$_2$ from Separtis; eluent gradient: dichloromethane/MeOH 100:0->90:10) followed by triruration in ether to afford an off-white solid, (52 mg, 8%); MS (ISP): 221.2 ([M+H]$^+$).

EXAMPLE 30

(S)-4-{2-[1-(4-Chloro-phenyl)-cyclopropyl]-ethyl}-4,5-dihydro-oxazol-2-ylamine

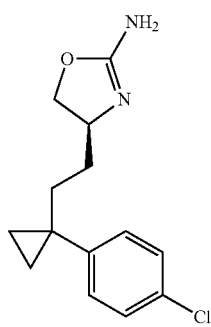 [SMILES: NC1=N[C@@H](CCC2(c3ccc(Cl)cc3)CC2)CO1]

a) (R)-4-(Benzothiazol-2-ylsulfanyl-methyl)-2,2-dimethyl-oxazolidine-3-carboxylic acid tert-butyl ester To a stirred, cooled (0° C.) solution of (S)-4-hydroxymethyl-2,2-dimethyl-oxazolidine-3-carboxylic acid tert-butyl ester (1.36 g), 2-mercaptobenzothiazole (1.48 g) and triphenylphosphine (2.32 g) in THF (80 ml) under an argon atmosphere was added diethyl azodicarboxylate (4.1 ml; 40% solution in toluene). The mixture (soon turning to a yellow suspension, slowly warming up to r.t.) was stirred for 18 h overnight, then diluted with EtOAc and washed with sat. aq. Na$_2$CO$_3$. The aqueous phase was back extracted with EtOAc. The combined organics were washed with brine, dried over MgSO$_4$, filtered and concentrated. The crude product was purified by column chromatography (SiO$_2$; gradient: cyclohexane ->cyclohexane/EtOAc 85:15) to give (R)-4-(benzothiazol-2-ylsulfanyl-methyl)-2,2-dimethyl-oxazolidine-3-carboxylic acid tert-butyl ester (2.1 g) as light yellow viscous oil.

b) (R)-4-(Benzothiazole-2-sulfonylmethyl)-2,2-dimethyl-oxazolidine-3-carboxylic acid tert-butyl ester To a stirred solution of (R)-4-(benzothiazol-2-ylsulfanyl-methyl)-2,2-dimethyl-oxazolidine-3-carboxylic acid tert-butyl ester (2.0 g) at 0° C. in dichloromethane (80 ml) under an argon atmosphere was added 3-chloroperbenzoic acid (2.29 g) in one portion. The mixture (slowly warming up to r.t.) was stirred overnight. The mixture was washed with 10% aq. sodium bisulfite (80 ml), sat. aq. Na$_2$CO$_3$ and brine, dried over MgSO$_4$, filtered and concentrated. The crude product was isolated by column chromatography (SiO$_2$; gradient: cyclohexane ->cyclohexane/EtOAc 3:2) to give (R)-4-(benzothiazole-2-sulfonylmethyl)-2,2-dimethyl-oxazolidine-3-carboxylic acid tert-butyl ester (1.6 g) as white solid. MS (ISP): 413.3 ([M+H]$^+$))

c) (S)-4-{(Z)-2-[1-(4-Chloro-phenyl)-cyclopropyl]-vinyl}-2,2-dimethyl-oxazolidine-3-carboxylic acid tert-butyl ester To a stirred, cooled (0° C.) solution of 1-(4-chloro-phenyl)-cyclopropanecarbaldehyde (0.36 g) in tetrahydrofuran (15 ml) was added under an argon atmosphere (R)-4-(benzothiazole-2-sulfonylmethyl)-2,2-dimethyl-oxazolidine-3-carboxylic acid tert-butyl ester (1.0 g) followed by a 1 M solution of LiHMDS in THF (4.8 ml). After 1 h at 0° C. the cooling bath was removed and stirring was continued overnight. The mixture was quenched by the addition of sat. aqueous NH$_4$Cl (15 ml) and H$_2$O (15 ml) and extracted with EtOAc. The aqueous phase was back extracted with EtOAc. The combined organics were washed with brine, dried over MgSO$_4$, filtered and concentrated. The crude product was purified by column chromatography (SiO$_2$; gradient: heptane ->heptane/EtOAc 2:1) to give (S)-4-{(Z)-2-[1-(4-chloro-phenyl)-cyclopropyl]-vinyl}-2,2-dimethyl-oxazolidine-3-carboxylic acid tert-butyl ester (0.72 g) as light yellow viscous oil. MS (ISP): 378.3 ([M+H]$^+$))

d) (S)-4-{2-[1-(4-Chloro-phenyl)-cyclopropyl]-ethyl}-2,2-dimethyl-oxazolidine-3-carboxylic acid tert-butyl ester To a stirred solution of (S)-4-{(Z)-2-[1-(4-chloro-phenyl)-cyclopropyl]-vinyl}-2,2-dimethyl-oxazolidine-3-carboxylic acid tert-butyl ester (0.55 g) at room temperature in methanol (2 ml) under an argon atmosphere was added platinum oxide (31 mg). The mixture was stirred at r.t. under a hydrogen atmosphere for 1 hour. The catalyst was filtered off, the filtrate was concentrated and purified by column chromatography (SiO$_2$; heptane/EtOAc) to give (S)-4-{2-[1-(4-chloro-phenyl)-cyclopropyl]-ethyl}-2,2-dimethyl-oxazolidine-3-carboxylic acid tert-butyl ester (0.5 g) as a white solid. MS (ISP): 380.4 ([M+H]$^+$))

e) (S)-2-Amino-4-[1-(4-chloro-phenyl)-cyclopropyl]-butan-1-ol

To (S)-4-{2-[1-(4-chloro-phenyl)-cyclopropyl]-ethyl}-2,2-dimethyl-oxazolidine-3-carboxylic acid tert-butyl ester (0.5 g) was added under an argon atmosphere 5.5 M HCl solution in ethanol (2 ml). The mixture was stirred for 16 h. The mixture was concentrated. The residue was dissolved in dichloromethane and an excess of ammonia in methanol and some silica gel was added. The solvents were evaporated and the crude product was purified by column chromatography (column: Isolute® Flash-NH$_2$ from Separtis; eluent: dichloromethane/methanol=90:10) to give (S)-2-amino-4-[1-(4-chloro-phenyl)-cyclopropyl]-butan-1-ol (0.27 g) as a white solid. MS (ISP): 240.2 ([M+H]$^+$)).

f) (S)-4-{2-[1-(4-Chloro-phenyl)-cyclopropyl]-ethyl}-4,5-dihydro-oxazol-2-ylamine In analogy to example 1d (S)-2-amino-4-[1-(4-chloro-phenyl)-cyclopropyl]-butan-1-ol was reacted with cyanogen bromide to give (S)-4-{2-[1-(4-chloro-phenyl)-cyclopropyl]-ethyl}-4,5-dihydro-oxazol-2-ylamine. White solid. MS (ISP): 265.1 ([M+H]$^+$))

EXAMPLE 31

(S)-4-[2-(1-Phenyl-cyclopropyl)-ethyl]-4,5-dihydro-oxazol-2-ylamine

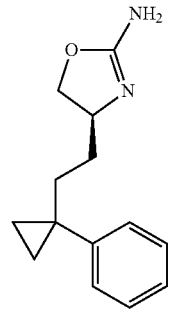 [SMILES: NC1=N[C@@H](CCC2(c3ccccc3)CC2)CO1]

The title compound was obtained in analogy to example 30 starting from 1-phenylcyclopropanecarbaldehyde instead of 1-(4-chloro-phenyl)-cyclopropanecarbaldehyde. Light yellow solid. MS (ISP): 206.2 ([M+H]$^+$).

EXAMPLE 32

(S)-4-(2-m-Tolyloxy-ethyl)-4,5-dihydro-oxazol-2-ylamine

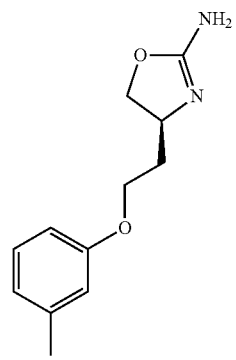 [SMILES: Cc1cccc(OCC[C@H]2COC(N)=N2)c1]

The title compound was obtained in analogy to example 3 starting from 3-methylphenol instead of 4-chlorophenol. White solid. MS (ISP): 221.2 ([M+H]$^+$).

EXAMPLE 33

(S)-4-[2-(Biphenyl-3-yloxy)-ethyl]-4,5-dihydro-oxazol-2-ylamine

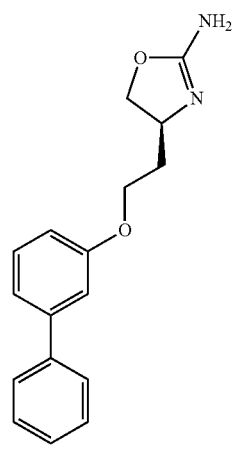 [SMILES: NC1=N[C@@H](CCOc2cccc(-c3ccccc3)c2)CO1]

The title compound was obtained in analogy to example 3 starting from biphenyl-3-ol instead of 4-chlorophenol. White solid. MS (ISP): 283.1 ([M+H]$^+$)

EXAMPLE 34

(S)-4-[2-(3-Benzyloxy-phenoxy)-ethyl]-4,5-dihydro-oxazol-2-ylamine

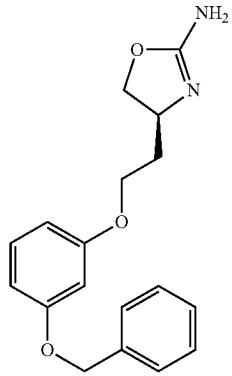 [SMILES: NC1=N[C@@H](CCOc2cccc(OCc3ccccc3)c2)CO1]

The title compound was obtained in analogy to example 3 starting from 3-benzyloxyphenol instead of 4-chlorophenol. White solid. MS (ISP): 313.2 ([M+H]$^+$)

EXAMPLE 35

(S)-4-[2-(3-Bromo-phenoxy)-ethyl]-4,5-dihydro-oxazol-2-ylamine

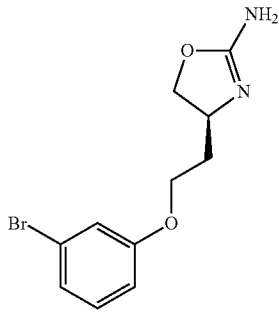 [SMILES: NC1=N[C@@H](CCOc2cccc(Br)c2)CO1]

The title compound was obtained in analogy to example 3 starting from 3-bromophenol instead of 4-chlorophenol. Colourless oil. MS (ISP): 284.9; 287.0 ([M+H]$^+$)

EXAMPLE 36

(S)-4-[2-(4-Phenoxy-phenoxy)-ethyl]-4,5-dihydro-oxazol-2-ylamine

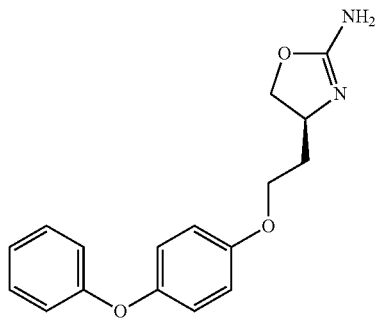 [SMILES: NC1=N[C@@H](CCOc2ccc(Oc3ccccc3)cc2)CO1]

The title compound was obtained in analogy to example 3 starting from 4-phenoxyphenol instead of 4-chlorophenol. White solid. MS (ISP): 299.2 ([M+H]$^+$)

EXAMPLE 37

(4S)-4-[2-(4-Chloro-phenoxy)-propyl]-4,5-dihydro-oxazol-2-ylamine

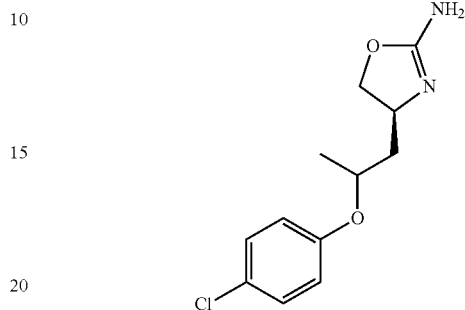

The title compound was obtained in analogy to example 12 starting from 2-(4-chlorophenoxy)-propan-1-ol (CAS 63650-24-8) instead of 4,4,4-trifluoro-3-phenyl-butan-1-ol. Colourless gum. MS (ISP): 257.3 ([{$^{37}$Cl}M+H]$^+$), 255.2 ([{$^{35}$Cl}M+H]$^+$).

EXAMPLE 38

(RS)-4-(2,2-Dimethyl-3-phenyl-propyl)-4,5-dihydro-oxazol-2-ylamine

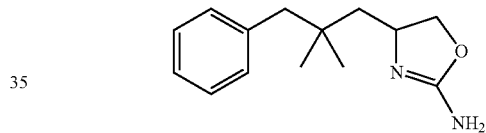

a) (RS)-5-(2,2-Dimethyl-3-phenyl-propyl)-imidazolidine-2,4-dione

To a stirred suspension of 3,3-dimethyl-4-phenyl-butyraldehyde (2.46 g; CAS 15674-36-9) at r.t. in ethanol (25 ml) under an argon atmosphere were added H$_2$O (25 ml), ammonium carbonate (6.71 g) and NaCN (0.82 g). The mixture was heated to 60° C. (internal temperature), and stirring was continued for 17 h. The mixture was cooled to 0° C. The reactor was equiped with a 4 N NaOH trap in order to trap the evolving HCN. 3 N HCl (25 ml) was added dropwise for 10 min (temperature of the reaction mixture not over 9° C. during the addition). When addition was complete, a stream of air was passed through the reaction mixture (still kept in an ice bath) for 30 min in order to ensure complete removal of HCN. The product was collected by filtration, washed with plenty of H$_2$O and cyclohexane and dried to give (RS)-5-(2,2-dimethyl-3-phenyl-propyl)-imidazolidine-2,4-dione (2.05 g) as off-white powder. MS (ISN): 245.2 ([M–H]$^-$))

b) (RS)-2-Amino-4,4-dimethyl-5-phenyl-pentanoic acid

A suspension of (RS)-5-(2,2-dimethyl-3-phenyl-propyl)-imidazolidine-2,4-dione (2.04 g) in 4 N NaOH was heated under an argon atmosphere to 120° C. (oil bath temperature). After 30 min strong foaming was observed. More 4 N NaOH (20 ml) was added. The suspension was heated to 120° C. for 2 days, turning into a clear solution. The mixture was cooled to r.t. and the insoluble material was filtered off The filtrate was cooled in an ice bath and concentrated HCl was carefully added until pH ~6 was reached. The solid that had precipitated out was collected by filtration, washed with plenty of H$_2$O and with Et$_2$O, and dried to give (RS)-2-amino-4,4-dimethyl-5-phenyl-pentanoic acid (5.39 g, product contains large amount of salt) as white solid which was used in the next step without further purification.

c) (RS)-2-Amino-4,4-dimethyl-5-phenyl-pentan-1-ol

A 2M solution of LiBH$_4$ at r.t. in THF (12.2 ml) was diluted under an argon atmosphere with THF (20 ml). To this was added rapidely trimethylsilyl chloride (4.11 ml). A white precipitate formed at the end of the addition. The mixture was then cooled in an ice bath and (RS)-2-amino-4,4-dimethyl-5-phenyl-pentanoic acid (salt-containing product from example 38.b) was added portionwise (bubbling!) over a period of 5 min. Stirring at 0° C. was continued for 1 h, then the ice bath was removed and the compact light yellow suspension was stirred at r.t. for 18 h. The mixture was cooled again to 0° C. and methanol (12 ml) was added dropwise leading to strong bubbling and gas evolution. The ice bath was removed and stirring at r.t. was continued for 30 min. The mixture was filtered and concentrated to leave an off-white paste. This was taken up in H$_2$O (30 ml) and acidified to pH ~1 by the addition of 3 N HCl with vigorous stirring. After stirring 30 min at r.t. the almost clear solution was washed with EtOAc.

The aqueous layer was brought to pH 12 by the addition of 4 N NaOH and the product was extracted with EtOAc. The combined organics were washed with brine, dried (MgSO$_4$), filtered and concentrated to give (RS)-2-amino-4,4-dimethyl-5-phenyl-pentan-1-ol (974 mg) as light yellow viscous oil which turned to an off-white solid after standing a few hours at r.t. The crude product was used in the next reaction step without further purification. MS (ISP): 208.3 ([M+H]$^+$))

d) (RS)-4-(2,2-Dimethyl-3-phenyl-propyl)-4,5-dihydro-oxazol-2-ylamine

To a stirred solution of (RS)-2-amino-4,4-dimethyl-5-phenyl-pentan-1-ol (0.97 g) at r.t. in THF (15 ml) under an argon atmosphere were added K$_2$CO$_3$ (0.78 g) and a solution of BrCN (0.59 g) in THF (10 ml). The mixture was stirred for 17 h. The suspension was diluted with EtOAc and washed with H$_2$O. The aqueous phase was back-extracted with EtOAc. The combined organics were washed with brine, dried (MgSO$_4$), filtered and concentrated. The crude product was purified by chromatography on Isolute® Flash-NH$_2$ silica gel from Separtis (gradient: cyclohexane ->CH$_2$Cl$_2$->CH$_2$Cl$_2$/MeOH 9:1) to give (RS)-4-(2,2-dimethyl-3-phenylpropyl)-4,5-dihydro-oxazol-2-ylamine (0.59 g) as an off-white sticky solid. MS (ISP): 233.2 ([M+H]$^+$))

EXAMPLE 39

(RS)-4-[2-(4-Fluoro-phenoxy)-ethyl]-4-methyl-4,5-dihydro-oxazol-2-ylamine

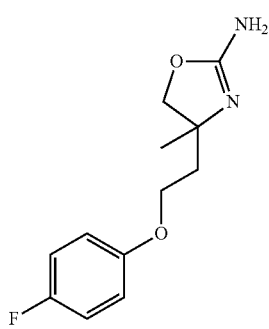 [SMILES: CC1(CCOc2ccc(F)cc2)COC(N)=N1]

The title compound was obtained in analogy to example 29 starting from 3-methyl-3-buten-1-ol and 4-fluoro-phenol. Light brown viscous oil. MS (ISP): 239.1 ([M+H]$^+$).

EXAMPLE 40

(RS)-4-[2-(3,4-Difluoro-phenoxy)-ethyl]-4-methyl-4,5-dihydro-oxazol-2-ylamine

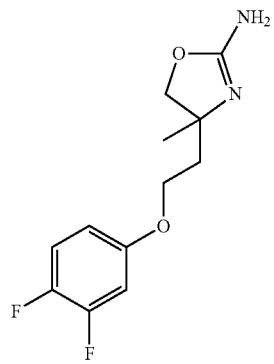 [SMILES: CC1(CCOc2ccc(F)c(F)c2)COC(N)=N1]

The title compound was obtained in analogy to example 29 starting from 3-methyl-3-buten-1-ol and 3,4-difluoro-phenol. Light brown viscous oil. MS (ISP): 257.1 ([M+H]$^+$).

EXAMPLE 41

(4S)-4-(2-m-Tolyloxy-propyl)-4,5-dihydro-oxazol-2-ylamine

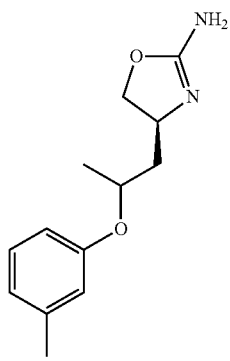 [SMILES: Cc1cccc(OC(C)C[C@H]2COC(N)=N2)c1]

The title compound was obtained in analogy to example 12 starting from 2-m-tolyloxypropan-1-ol (CAS 6773-95-1) instead of 4,4,4-trifluoro-3-phenyl-butan-1-ol. Colourless oil. MS (ISP): 235.2 ([M+H]$^+$).

EXAMPLE 42

(4S)-4-(3-m-Tolyl-pentyl)-4,5-dihydro-oxazol-2-ylamine

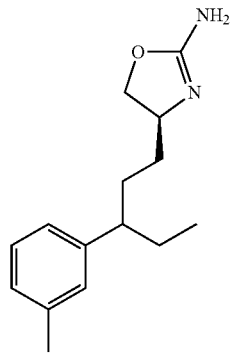 [SMILES: CCC(CC[C@H]1COC(N)=N1)c1cccc(C)c1]

The title compound was obtained in analogy to the sequence of example 28 starting from diethyl 3-(methyl)-benzylphosphonate and diethyl sulphate. Colourless oil. MS (ISP): 247.4 ([M+H]$^+$)

EXAMPLE 43

(S)-4-[2-(Dimethyl-phenyl-silanyl)-ethyl]-4,5-dihydro-oxazol-2-ylamine

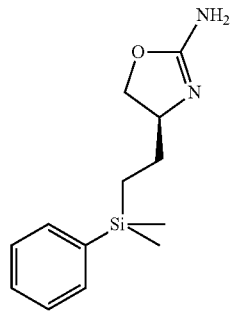 [SMILES: C[Si](C)(CC[C@H]1COC(N)=N1)c1ccccc1]

a) S-4-[2-Dimethyl-phenyl-silanyl)-ethyl]-2,2-dimethyl-oxazolidine-3-carboxylic acid tert-butyl ester (S)-2,2-Dimethyl-4-vinyl-oxazolidine-3-carboxylic acid tert-butyl ester (750 mg; CAS 133625-87-3) was dissolved in dimethylphenylsilane (25 ml), platinum(IV)-oxide (187 mg) was added and the mixture was stirred overnight at room temperature. The catalyst was filtered off and the filtrate was evaporated in vacuo. The crude product was purified by column chromatography (SiO$_2$; heptane/ethyl acetate=4:1) to give (S)-4-[2-(dimethyl-phenyl-silanyl)ethyl]-2,2-dimethyl-oxazolidine-3-carboxylic acid tert-butyl ester (1.14 g, 95%) as colourless oil, which was used directly for the next step.

b) (S)-2-Amino-4-(4-dimethyl-phenyl-silanyl)-butan-1-ol

To (S)-4-[2-(dimethyl-phenyl-silanyl)-ethyl]-2,2-dimethyl-oxazolidine-3-carboxylic acid tert-butyl ester (1.14 g) was added under an argon atmosphere 5.5 M HCl solution in ethanol (5 ml). The mixture was stirred for 2 h. Sodium bicarbonate (1 g) was added as powder. Water (5 ml) was added and the suspension was extracted with dichloromethane (3 times 20 ml). The combined organic layers were dried (MgSO4) and evaporated. The residue was purified by column chromatography (column: Isolute® Flash-NH$_2$ from Separtis; eluent: dichloromethane/methanol=95:5) to give (S)-2-amino-4-(4-dimethyl-phenyl-silanyl)-butan-1-ol (540 mg, 77%) as a colourless oil. MS (ISP): 224.2 ([M+H]$^+$)).

c) (S)-4-[2-Dimethyl-phenyl-silayl)-ethyl]-4,5-dihydro-oxazol-2-ylamine

In analogy to example 1d (S)-2-amino-4-(4-dimethyl-phenyl-silanyl)-butan-1-ol was reacted with cyanogen bromide to give (S)-4-[2-(dimethyl-phenyl-silanyl)-ethyl]-4,5-dihydro-oxazol-2-ylamine. Colourless oil. MS (ISP): 249.1 ([M+H]$^+$)).

EXAMPLE 44

(RS)-4-[2-(3-Chloro-4-fluoro-phenoxy)-ethyl]-4-methyl-4,5-dihydro-oxazol-2-ylamine

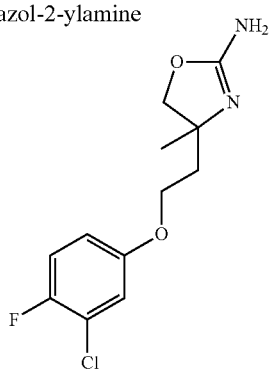

The title compound was obtained in analogy to example 29 starting from 3-methyl-3-buten-1-ol and 3-chloro-4-fluoro-phenol. Light brown viscous oil. MS (ISP): 275.2 ([{$^{37}$Cl}M+H]$^+$), 273.1 ([{$^{35}$Cl}M+H]$^+$).

EXAMPLE 45

(S)-4-[(S)-2-(4-Chloro-phenoxy)-propyl]-4,5-dihydro-oxazol-2-ylamine

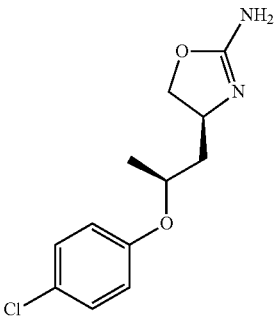 [SMILES: C[C@@H](C[C@H]1COC(N)=N1)Oc1ccc(Cl)cc1]

a) (S)-4-(R)-2-Hydroxy-propyl)-2,2-dimethyl-oxazolidine-3-carboxylic acid tert-butyl ester and (S)-4-((S)-2-Hydroxy-propyl)-2,2-dimethyl-oxazolidine-3-carboxylic acid tert-butyl ester

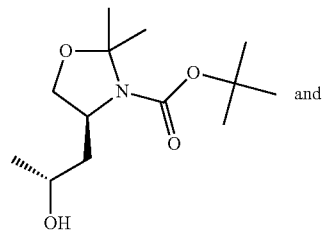

and

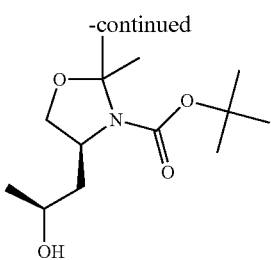

To a stirred solution of (S)-2,2-dimethyl-4-(2-oxo-ethyl)-oxazolidine-3-carboxylic acid tert-butyl ester (12.0 g; CAS 147959-19-1) in dry diethyl ether (200 ml) under an argon atmosphere at room temperature was added dropwise a solution of methylmagnesium bromide in diethyl ether (49.3 ml, 3 M solution) and stirring continued overnight. The reaction mixture was then quenched by careful addition of water and extracted twice with ethyl acetate. The combined organic phases were dried over sodium sulphate, filtered and concentrated in vacuo. The reside was purified by column chromatography (SiO$_2$; gradient: heptane/EtOAc 100:0→50:50) to give (S)-4-(R)-2-hydroxy-propyl)-2,2-dimethyl-oxazolidine-3-carboxylic acid tert-butyl ester (5.89 g) from fractions eluting first and (S)-4-(S)-2-hydroxy-propyl)-2,2-dimethyl-oxazolidine-3-carboxylic acid tert-butyl ester (4.07 g) from fractions eluting later, both compounds as light yellow oils. (S)-4-(R)-2-hydroxy-propyl)-2,2-dimethyl-oxazolidine-3-carboxylic acid tert-butyl ester: $^1$H NMR δ (CDCl$_3$, 300 MHz): 4.60 (1H, br. D, J=3.3 Hz), 4.23 (1H, m), 4.00 (1H, dd, J=8.7 & 5.4 Hz), 3.71 (1H, m), 3.65 (1H, d, J=8.7 Hz), 1.76 (1H, td, J=11.4 & 2.1 Hz), 1.61-1.46 (16H, m), 1.20 (3H, d, J=6.3 Hz). (S)-4-(S)-2-hydroxy-propyl)-2,2-dimethyl-oxazolidine-3-carboxylic acid tert-butyl ester: $^1$H NMR δ (CDCl$_3$, 300 MHz): 4.13 (1H, m), 3.98 (1H, m), 3.85-3.60 (2H, m), 2.50 (1H, br. s), 1.80 (1H, m), 1.60-1.49 (16H, m), 1.22 (3H, d, J=6.3 Hz).

b) (S)-4-[(S)-2-(4-Chloro-phenoxy)-propyl]-2,2-dimethyl-oxazolidine-3-carboxylic acid tert-butyl ester

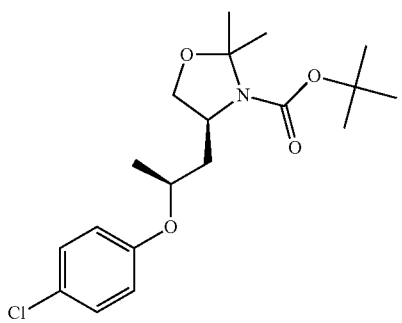 [SMILES: C[C@@H](C[C@H]1COC(C)(C)N1C(=O)OC(C)(C)C)Oc1ccc(Cl)cc1]

To a stirred solution of (S)-4-(R)-2-hydroxy-propyl)-2,2-dimethyl-oxazolidine-3-carboxylic acid tert-butyl ester (2.74 g) in THF (25 ml) were added 4-chlorophenol (1.65 g), triphenylphosphine (3.50 g) and di-tert-butyl azodicarboxylate (3.00 g). The resulting yellow solution was stirred at 70° C. overnight. The reaction mixture was cooled to room temperature and diluted with ethyl acetate, and then washed twice with 1 M aq. sodium hydroxide solution.

The organic layer was separated, dried over sodium sulphate and concentrated in vacuo. The crude product was purified by column chromatography (SiO$_2$; gradient: heptane/EtOAc 100:0→70:30) to give (S)-4-[(S)-2-(4-chlorophenoxy)-propyl]-2,2-dimethyl-oxazolidine-3-carboxylic acid tert-butyl ester (1.35 g, 34%) as a white solid. MS (ISP): 372.2 ([{$^{37}$Cl}M+H]$^+$), 370.2 ([{$^{35}$Cl}M+H]$^+$).

c) (2S,4S)-2-Amino-4-(4-chloro-phenoxy)-pentan-1-ol

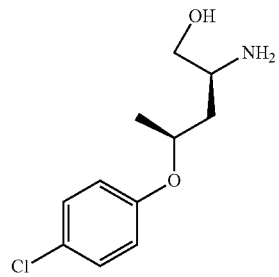

To a solution of trifluoroacetic acid (0.85 ml) in water (18 ml) was added dropwise a solution of (S)-4-[(S)-2-(4-chloro-phenoxy)-propyl]-2,2-dimethyl-oxazolidine-3-carboxylic acid tert-butyl ester (1.34 g) in acetonitrile (3 ml). The mixture was heated for 4 h at 80° C. with mechanical shaking The mixture was then cooled to room temperature and diluted with ethyl acetate. The mixture was washed with aq. sodium bicarbonate solution and then the organic phse was separated, dried over sodium sulphate and concentrated in vacuo to give (2S,4S)-2-amino-4-(4-chloro-phenoxy)-pentan-1-ol (0.76 g, 92%) as an off-white solid. MS (ISP): 232.1 ([{$^{37}$Cl}M+H]$^+$), 230.2 ([{$^{35}$Cl}M+H]$^+$).

d) (S)-4-[(S)-2-(4-Chloro-phenoxy)-propyl]-4,5-dihydro-oxazol-2-ylamine

In analogy to example 1d (2S,4S)-2-amino-4-(4-chloro-phenoxy)-pentan-1-ol was reacted with cyanogen bromide to give (S)-4-[(S)-2-(4-chloro-phenoxy)-propyl]-4,5-dihydro-oxazol-2-ylamine. Light yellow solid. MS (ISP): 257.2 ([{$^{37}$Cl}M+H]$^+$), 255.2 ([{$^{35}$Cl}M+H]$^+$).

EXAMPLE 46

(4S)-4-(3-Methoxy-3-phenyl-propyl)-4,5-dihydro-oxazol-2-ylamine

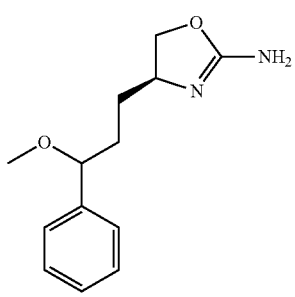 [SMILES: COC(CC[C@H]1COC(N)=N1)c1ccccc1]

The title compound was obtained in analogy to example 12 starting from 3-methoxy-3-phenyl-propan-1-ol instead of 4,4,4-trifluoro-3-phenyl-butan-1-ol. Off-white solid. MS (ISP): 235.2 ([M+H]$^+$).

EXAMPLE 47

(S)-4-[2-(4-Benzyl-phenoxy)-ethyl]-4,5-dihydro-oxazol-2-ylamine

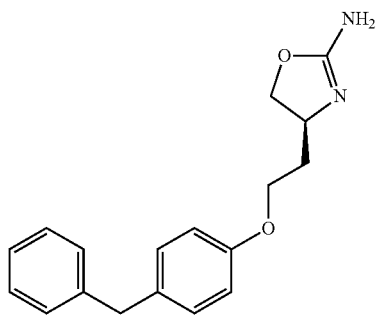 [SMILES: NC1=N[C@@H](CCOc2ccc(Cc3ccccc3)cc2)CO1]

The title compound was obtained in analogy to example 3 starting from 4-benzyl-phenol instead of 4-chlorophenol. White solid. MS (ISP): 297.2 ([M+H]$^+$).

EXAMPLE 48

(S)-4-[2-(4'-Fluoro-biphenyl-4-yloxy)-ethyl]-4,5-dihydro-oxazol-2-ylamine

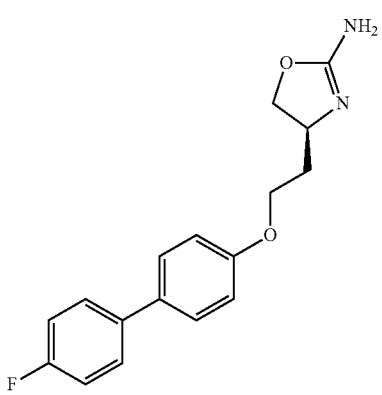 [SMILES: NC1=N[C@@H](CCOc2ccc(-c3ccc(F)cc3)cc2)CO1]

The title compound was obtained in analogy to example 3 starting from 4'-fluoro-biphenyl-4-ol instead of 4-chlorophenol. White solid. MS (ISP): 301.3 ([M+H]$^+$).

EXAMPLE 49

(RS)-4-Methyl-4-[2-(3-trifluoromethyl-phenoxy)-ethyl]-4,5-dihydro-oxazol-2-ylamine

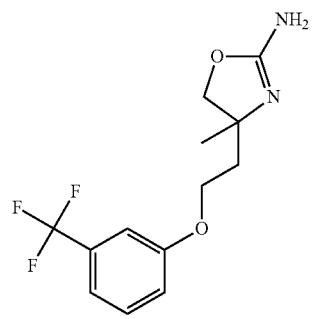 [SMILES: CC1(CCOc2cccc(C(F)(F)F)c2)COC(N)=N1]

The title compound was obtained in analogy to example 29 starting from 3-methyl-3-buten-1-ol and 3-trifluoromethyl-phenol. Light brown viscous oil. MS (ISP): 289.2 ([M+H]$^+$).

EXAMPLE 50

(RS)-4-Methyl-4-[2-(4-trifluoromethyl-phenoxy)-ethyl]-4,5-dihydro-oxazol-2-ylamine

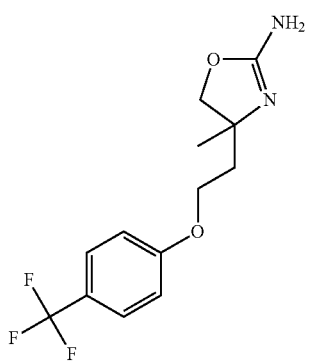 [SMILES: CC1(CCOc2ccc(C(F)(F)F)cc2)COC(N)=N1]

The title compound was obtained in analogy to example 29 starting from 3-methyl-3-buten-1-ol and 4-trifluoromethyl-phenol. Light brown viscous oil. MS (ISP): 289.1 ([M+H]$^+$).

EXAMPLE 51

4-[2-(2-Chloro-phenoxy)-ethyl]-4-methyl-4,5-dihydro-oxazol-2-ylamine

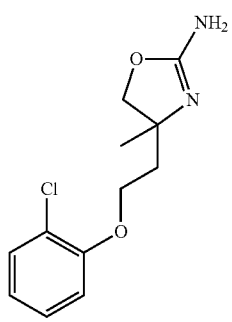

The title compound was obtained in analogy to example 29 starting from 3-methyl-3-buten-1-ol and 2-chloro-phenol. Light brown viscous oil. MS (ISP): 257.3 ([{$^{37}$Cl}M+H]$^+$), 255.2 ([{$^{35}$Cl}M+H]$^+$).

EXAMPLE 52

(RS)-4-Methyl-4-(2-m-tolyloxy-ethyl)-4,5-dihydro-oxazol-2-ylamine

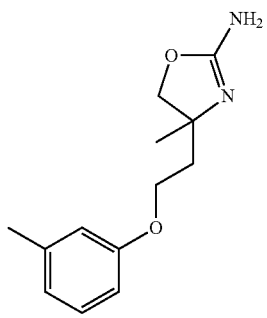 [SMILES: Cc1cccc(OCCC2(C)COC(N)=N2)c1]

The title compound was obtained in analogy to example 29 starting from 3-methyl-3-buten-1-ol and 3-methyl-phenol. Light brown viscous oil. MS (ISP): 235.3 ([M+H]+).

EXAMPLE 53

(S)-4-(2-Cyclohexyloxy-ethyl)-4,5-dihydro-oxazol-2-ylamine

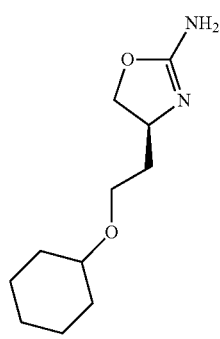 [SMILES: NC1=N[C@@H](CCOC2CCCCC2)CO1]

a) (S)-2,2-Dimethyl-4-(2-phenoxy-ethyl)-oxazolidine-3-carboxylic acid tert-butyl ester

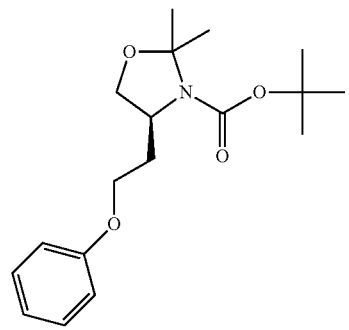 [SMILES: CC(C)(C)OC(=O)N1[C@@H](CCOc2ccccc2)COC1(C)C]

The title compound was obtained in analogy to example 3a starting from phenol instead of 4-chlorophenol. Colourless oil. MS (ISP): 322.3 ([M+H]+).

b) (S)-4-(2-Cyclohexyloxy-ethyl)-2,2-dimethyl-oxazolidine-3-carboxylic acid tert-butyl ester

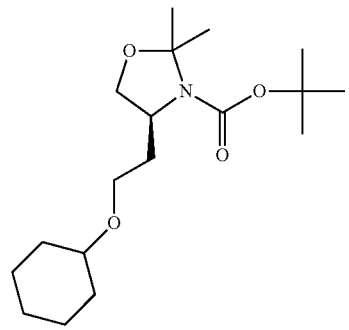 [SMILES: CC(C)(C)OC(=O)N1[C@@H](CCOC2CCCCC2)COC1(C)C]

To a solution of (S)-2,2-dimethyl-4-(2-phenoxy-ethyl)-oxazolidine-3-carboxylic acid tert-butyl ester (150 mg) in ethanol (3 ml) at room temperature was added rhodium on activated alumina (15 mg). The mixture was stirred under an atmosphere of hydrogen (1 atm) at room temperature for 16 h. The catalyst was removed by filtration and the filtrate was concentrated in vacuo to yield (S)-4-(2-cyclohexyloxy-ethyl)-2,2-dimethyl-oxazolidine-3-carboxylic acid tert-butyl ester as a black oil (145 mg, 95%); MS (ISP): 328.4 ([M+H]+).

c) (S)-4-(2-Cyclohexyloxy-ethyl)-4,5-dihydro-oxazol-2-ylamine

The title compound was obtained in analogy to example 3b-c starting from (S)-4-(2-cyclohexyloxy-ethyl)-2,2-dimethyl-oxazolidine-3-carboxylic acid tert-butyl ester. Colourless oil. MS (ISP): 213.3 ([M+H]+).

EXAMPLE 54

(S)-4-[2-(4-Chloro-3-fluoro-phenoxy)-ethyl]-4,5-dihydro-oxazol-2-ylamine

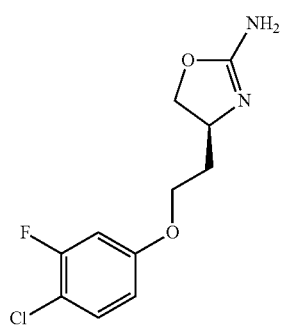 [SMILES: NC1=N[C@@H](CCOc2ccc(Cl)c(F)c2)CO1]

The title compound was obtained in analogy to example 3 starting from 4-chloro-3-fluoro-phenol instead of 4-chlorophenol. White crystalline solid. MS (ISP): 261.1 ([{37Cl}M+H]+), 259.2 ([{35Cl}M+H]+).

EXAMPLE 55

(S)-4-[2-(4-Bromo-phenoxy)-ethyl]-4,5-dihydro-oxazol-2-ylamine

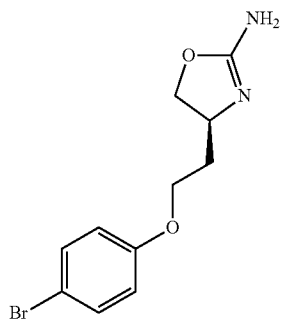

The title compound was obtained in analogy to example 3 starting from 4-chloro-3-fluoro-phenol instead of 4-chlorophenol. White crystalline solid. MS (ISP): 287.0 ([{81Br}M+H]+), 285.1 ([{79Br}M+H]+).

EXAMPLE 56

4-[2-((S)-2-Amino-4,5-dihydro-oxazol-4-yl)-ethoxy]-benzonitrile

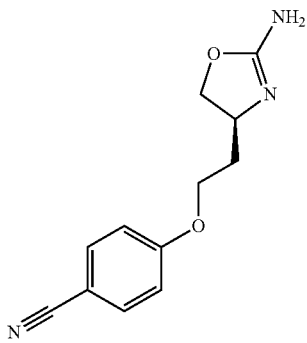 [SMILES: N#Cc1ccc(OCC[C@H]2COC(N)=N2)cc1]

The title compound was obtained in analogy to example 3 starting from 4-cyano-phenol instead of 4-chlorophenol. White crystalline solid. MS (ISP): 232.3 ([M+H]$^+$).

EXAMPLE 57

(S)-4-[2-(3,4-Dichloro-phenoxy)-ethyl]-4,5-dihydro-oxazol-2-ylamine

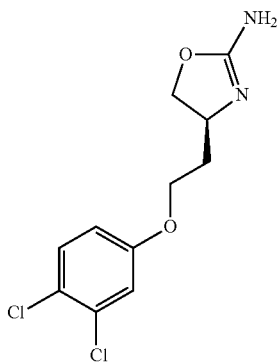 [SMILES: NC1=N[C@@H](CCOc2ccc(Cl)c(Cl)c2)CO1]

The title compound was obtained in analogy to example 3 starting from 3,4-dichlorophenol instead of 4-chlorophenol. White crystalline solid. MS (ISP): 279.0 ([{$^{37}$Cl}M+H]$^+$), 277.1 ([{$^{37}$Cl$^{35}$Cl}M+H]$^+$), 275.2 ([{$^{35}$Cl}M+H]$^+$).

EXAMPLE 58

(S)-4-[2-(4-Chloro-2-fluoro-phenoxy)-ethyl]-4,5-dihydro-oxazol-2-ylamine

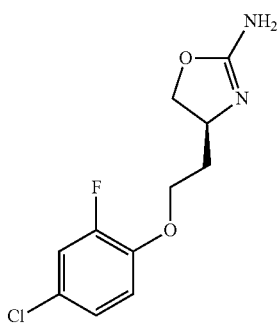 [SMILES: NC1=N[C@@H](CCOc2ccc(Cl)cc2F)CO1]

The title compound was obtained in analogy to example 3 starting from 4-chloro-2-fluoro-phenol instead of 4-chlorophenol. White crystalline solid. MS (ISP): 261.2 ([{$^{37}$Cl}M+H]$^+$), 259.2 ([{$^{35}$Cl}M+H]$^+$).

EXAMPLE 59

(S)-4-[2-(4-Methoxy-phenoxy)-ethyl]-4,5-dihydro-oxazol-2-ylamine

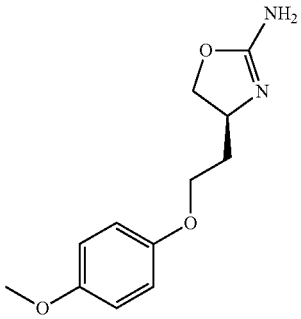 [SMILES: COc1ccc(OCC[C@H]2COC(N)=N2)cc1]

The title compound was obtained in analogy to example 3 starting from 4-methoxyphenol instead of 4-chlorophenol. Light yellow viscous oil. MS (ISP): 237.3 ([M+H]$^+$).

EXAMPLE 60

(S)-4-{2-[1-(4-Fluoro-phenyl)-cyclopropyl]-ethyl}-4,5-dihydro-oxazol-2-ylamine

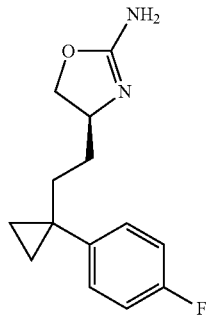

The title compound was obtained in analogy to example 30 starting from 1-(4-fluorophenyl)-cyclopropanecarbaldehyde instead of 1-(4-chloro-phenyl)-cyclopropanecarbaldehyde. White solid. MS (ISP): 249.1 ([M+H]$^+$).

EXAMPLE 61

(S)-4-{2-[(3-Chloro-phenyl)-dimethyl-silanyl]-ethyl}-4,5-dihydro-oxazol-2-ylamine

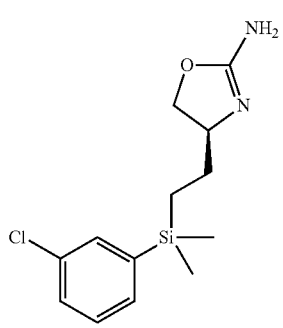 [SMILES: C[Si](C)(CC[C@H]1COC(N)=N1)c1cccc(Cl)c1]

The title compound was obtained in analogy to example 43 starting from (3-chlorophenyl)-dimethyl-silane instead of dimethylphenylsilane. Colourless oil. MS (ISP): 283.1 ([M+H]+).

EXAMPLE 62

(RS)-4-[2-(2-Fluoro-phenoxy)-ethyl]-4-methyl-4,5-dihydro-oxazol-2-ylamine

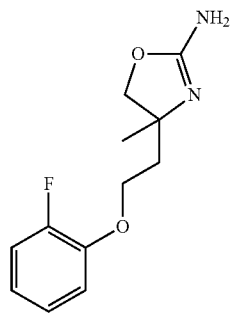 [SMILES: CC1(CCOc2ccccc2F)COC(N)=N1]

The title compound was obtained in analogy to example 29 starting from 3-methyl-3-buten-1-ol and 2-fluoro-phenol. Yellow viscous oil. MS (ISP): 239.1 ([M+H]+).

EXAMPLE 63

3-[2-((S)-2-Amino-4,5-dihydro-oxazol-4-yl)-ethoxy]-benzonitrile

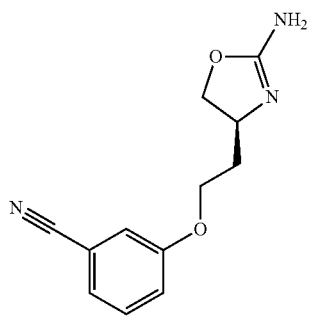 [SMILES: N#Cc1cccc(OCC[C@H]2COC(N)=N2)c1]

The title compound was obtained in analog to example 3 starting from 3-cyano-phenol instead of 4-chlorophenol. Colourless viscous oil. MS (ISP): 232.3 ([M+H]+).

EXAMPLE 64

((S)-4-[(S)-2-(4-Fluoro-phenoxy)-propyl]-4,5-dihydro-oxazol-2-ylamine

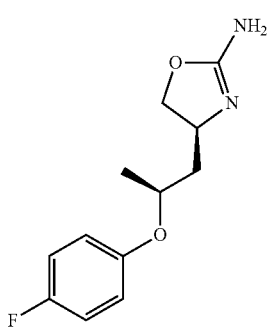 [SMILES: C[C@@H](C[C@H]1COC(N)=N1)Oc1ccc(F)cc1]

The title compound was obtained in analogy to example 45 starting from (S)-4-(R)-2-hydroxy-propyl)-2,2-dimethyl-oxazolidine-3-carboxylic acid tert-butyl ester and 4-fluoro-phenol. Light yellow solid. MS (ISP): 239.1 ([M+H]+).

EXAMPLE 65

4-[2-(4-Chloro-phenoxy)-2-methyl-propyl]-4,5-dihydro-oxazol-2-ylamine

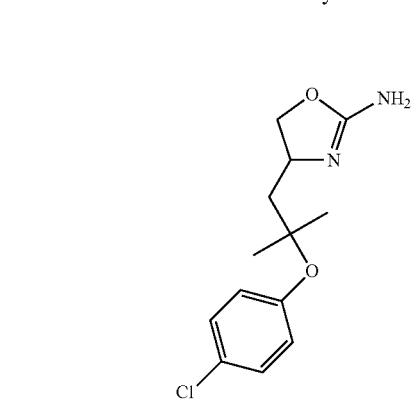

a) (2-Methyl-pent-4-en-2-oxy)diphenylphosphine

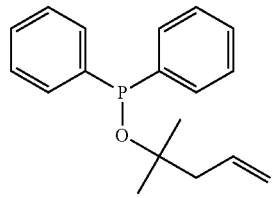 [SMILES: C=CCC(C)(C)OP(c1ccccc1)c1ccccc1]

To a stirred solution of 2-methyl-pent-4-en-2-ol (5.0 g; CAS 624-97-5) in THF (50 ml) were added sequentially 4-dimethylaminopyridine (1.22 g), triethylamine (8.32 ml) and chlorodiphenylphosphine (10.2 ml). The resulting mixture was stirred at room temperature overnight. The reaction mixture was evaporated and purified by column chromatography (basic alumina; gradient: heptane/EtOAc) to give (2-methyl-pent-4-en-2-oxy)diphenylphosphine (8.0 g, 56%) as a colourless oil which was used immediately in the next step.

b) 1-Chloro-4-(1,1-dimethyl-but-3-enyloxy)-benzene

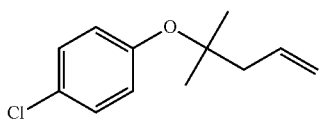

To a cooled (0° C.), stirred mixture of 4-chloro-phenol (4.34 g) and 2,6-dimethylbenzoquinone (4.60 g) was added dropwise a solution of (2-methyl-pent-4-en-2-oxy)diphenylphosphine (8.0 g) in dichloroethane (20 ml). The mixture was then heated at 95° C. for 24 h. The reaction mixture was cooled to room temperature and concentrated in vacuo and the residue was purified by column chromatography (SiO2; gradient: heptane/EtOAc) to give 1-chloro-4-(1,1-dimethyl-but-3-enyloxy)-benzene (0.14 g, 2%) as a colourless oil. MS (EI): 171.1 ([{$^{37}$Cl}M-C$_3$H$_5$]+), 1691 ([{$^{35}$Cl}M-C$_3$H$_5$]+).

c) 4-[2-(4-Chloro-phenoxy)-2-methyl-propyl]-4,5-dihydro-oxazol-2-ylamine

The title compound was obtained in analogy to example 29b starting from 1-chloro-4-(1,1-dimethyl-but-3-enyloxy)-benzene instead of (3-methyl-but-3-enyloxy)-benzene. White solid. MS (ISP): 271.3 ([$\{^{37}Cl\}$M+H]$^+$), 269.2 ([$\{^{35}Cl\}$M+H]$^+$).

EXAMPLE 66

(S)-4-{2-[(4-Fluoro-phenyl)-dimethyl-silanyl]-ethyl}-4,5-dihydro-oxazol-2-ylamine

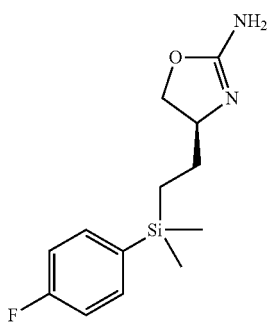 [SMILES: C[Si](C)(CC[C@H]1COC(N)=N1)c1ccc(F)cc1]

The title compound was obtained in analogy to example 43 starting from (4-fluorophenyl)-dimethyl-silane instead of dimethylphenylsilane. Colourless oil. MS (ISP): 267.3 ([M+H]$^+$).

EXAMPLE 67

(S)-4-{2-[(4-Chloro-phenyl)-dimethyl-silanyl]-ethyl}-4,5-dihydro-oxazol-2-ylamine

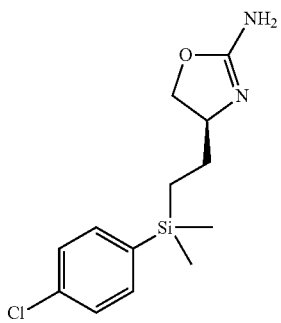 [SMILES: C[Si](C)(CC[C@H]1COC(N)=N1)c1ccc(Cl)cc1]

The title compound was obtained in analogy to example 43 starting from (4-chlorophenyl)-dimethyl-silane instead of dimethylphenylsilane. Colourless oil. MS (ISP): 283.1 ([M+H]$^+$).

EXAMPLE 68

(S)-4-[(S)-2-(3-Chloro-phenoxy)-propyl]-4,5-dihydro-oxazol-2-ylamine

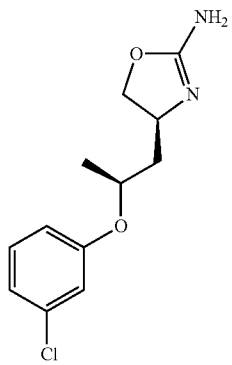 [SMILES: C[C@@H](C[C@H]1COC(N)=N1)Oc1cccc(Cl)c1]

The title compound was obtained in analogy to example 45 starting from (S)-4-(R)-2-hydroxy-propyl)-2,2-dimethyl-oxazolidine-3-carboxylic acid tert-butyl ester and 3-chloro-phenol. Colourless viscous oil. MS (ISP): 257.1 ([$\{^{37}Cl\}$M+H]$^+$), 255.1 ([$\{^{35}Cl\}$M+H]$^+$).

EXAMPLE 69

(S)-4-[(S)-2-(3,4-Difluoro-phenoxy)-propyl]-4,5-dihydro-oxazol-2-ylamine

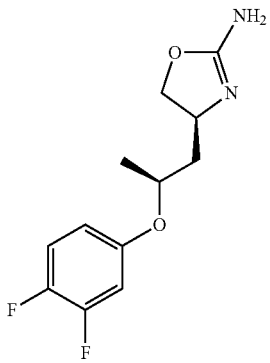 [SMILES: C[C@@H](C[C@H]1COC(N)=N1)Oc1ccc(F)c(F)c1]

The title compound was obtained in analogy to example 45 starting from (S)-4-(R)-2-hydroxy-propyl)-2,2-dimethyl-oxazolidine-3-carboxylic acid tert-butyl ester and 3,4-difluoro-phenol. Colourless viscous oil. MS (ISP): 257.1 ([M+H]$^+$).

EXAMPLE 70

(S)-4-[(S)-2-(4-Chloro-3-fluoro-phenoxy)-propyl]-4,5-dihydro-oxazol-2-ylamine

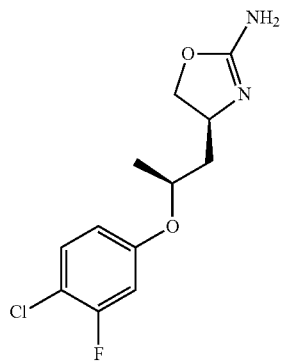 [SMILES: C[C@@H](C[C@H]1COC(N)=N1)Oc1ccc(Cl)c(F)c1]

The title compound was obtained in analogy to example 45 starting from (S)-4-(R)-2-hydroxy-propyl)-2,2-dimethyl-oxazolidine-3-carboxylic acid tert-butyl ester and 4-chloro-3-fluoro-phenol. Light yellow viscous oil. MS (ISP): 275.1 ([{$^{37}$Cl}M+H]$^+$), 273.1 ([{$^{35}$Cl}M+H]$^+$).

EXAMPLE 71

(S)-4-[(S)-2-(4-Bromo-phenoxy)-propyl]-4,5-dihydro-oxazol-2-ylamine

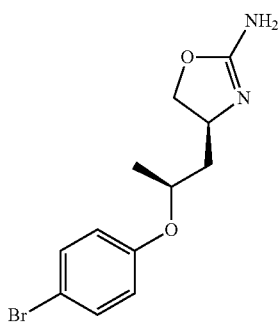

The title compound was obtained in analogy to example 45 starting from (S)-4-(R)-2-hydroxy-propyl)-2,2-dimethyl-oxazolidine-3-carboxylic acid tert-butyl ester and 4-bromo-phenol. White solid. MS (ISP): 301.0 ([{$^{81}$Br}M+H]$^+$), 299.1 ([{$^{79}$Br}M+H]$^+$).

EXAMPLE 72

(S)-4-[(S)-2-(3-Chloro-4-fluoro-phenoxy)-propyl]-4,5-dihydro-oxazol-2-ylamine

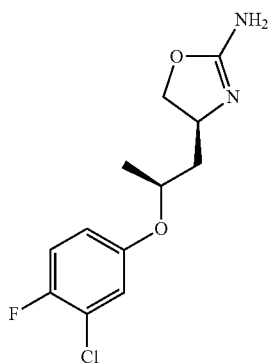 [SMILES: C[C@@H](C[C@H]1COC(N)=N1)Oc1ccc(F)c(Cl)c1]

The title compound was obtained in analogy to example 45 starting from (S)-4-(R)-2-hydroxy-propyl)-2,2-dimethyl-oxazolidine-3-carboxylic acid tert-butyl ester and 3-chloro-4-fluoro-phenol. Light yellow viscous oil. MS (ISP): 275.1 ([{$^{37}$Cl}M+H]$^+$), 273.1 ([{$^{35}$Cl}M+H]$^+$).

EXAMPLE 73

(S)-4-[(S)-2-(4-Chloro-2-fluoro-phenoxy)-propyl]-4,5-dihydro-oxazol-2-ylamine

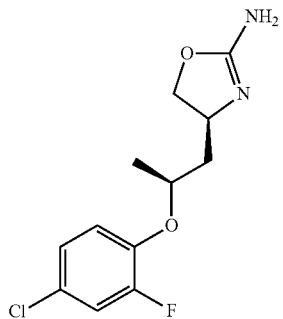 [SMILES: C[C@@H](C[C@H]1COC(N)=N1)Oc1ccc(Cl)cc1F]

The title compound was obtained in analogy to example 45 starting from (S)-4-(R)-2-hydroxy-propyl)-2,2-dimethyl-oxazolidine-3-carboxylic acid tert-butyl ester and 4-chloro-2-fluoro-phenol. White solid. MS (ISP): 275.1 ([{$^{37}$Cl}M+H]$^+$), 273.1 ([{$^{35}$Cl}M+H]$^+$).

EXAMPLE 74

(S)-4-[(S)-2-(2,4-Difluoro-phenoxy)-propyl]-4,5-dihydro-oxazol-2-ylamine

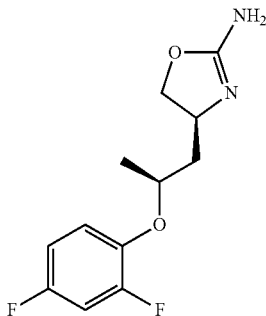 [SMILES: C[C@@H](C[C@H]1COC(N)=N1)Oc1ccc(F)cc1F]

The title compound was obtained in analogy to example 45 starting from (S)-4-((R)-2-hydroxy-propyl)-2,2-dimethyl-oxazolidine-3-carboxylic acid tert-butyl ester and 2,4-difluoro-phenol. Light yellow viscous oil. MS (ISP): 257.1 ([M+H]$^+$).

EXAMPLE 75

(S)-4-[(S)-2-(3,4-Dichloro-phenoxy)-propyl]-4,5-dihydro-oxazol-2-ylamine

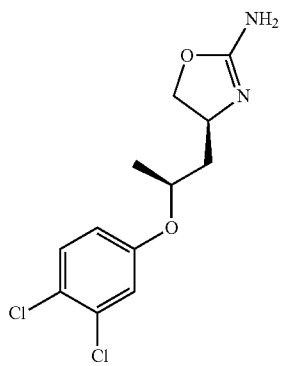 [SMILES: C[C@@H](C[C@H]1COC(N)=N1)Oc1ccc(Cl)c(Cl)c1]

The title compound was obtained in analogy to example 45 starting from (S)-4-(R)-2-hydroxy-propyl)-2,2-dimethyl-oxazolidine-3-carboxylic acid tert-butyl ester and 3,4-dichlorophenol. Colourless viscous oil. MS (ISP): 292.9 ([{$^{37}$Cl}M+H]$^+$), 290.9 ([{$^{37}$Cl$^{35}$Cl}M+H]$^+$), 289.0 ([{35Cl}M+H]$^+$).

EXAMPLE 76

4-[(S)-2-((S)-2-Amino-4,5-dihydro-oxazol-4-yl)-1-methyl-ethoxy]-benzonitrile

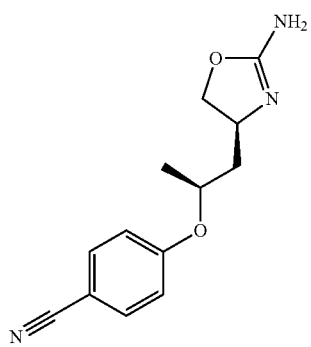 [SMILES: C[C@@H](C[C@H]1COC(N)=N1)Oc1ccc(C#N)cc1]

The title compound was obtained in analogy to example 45 starting from (S)-4-((R)-2-hydroxy-propyl)-2,2-dimethyl-oxazolidine-3-carboxylic acid tert-butyl ester and 4-cyanophenol. White solid. MS (ISP): 246.2 ([M+H]$^+$).

EXAMPLE 77

4-[(S)-2-((S)-2-Amino-4,5-dihydro-oxazol-4-yl)-1-methyl-ethoxy]-benzonitrile

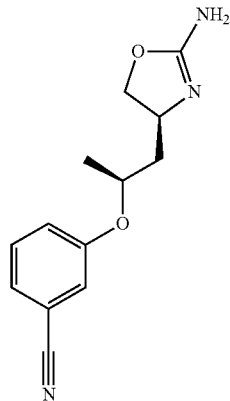 [SMILES: C[C@@H](C[C@H]1COC(N)=N1)Oc1cccc(C#N)c1]

The title compound was obtained in analogy to example 45 starting from (S)-4-((R)-2-hydroxy-propyl)-2,2-dimethyl-oxazolidine-3-carboxylic acid tert-butyl ester and 3-cyanophenol. White solid. MS (ISP): 246.2 ([M+H]$^+$).

EXAMPLE 78

(S)-4-[(S)-2-(4-Trifluoromethyl-phenoxy)-propyl]-4,5-dihydro-oxazol-2-ylamine

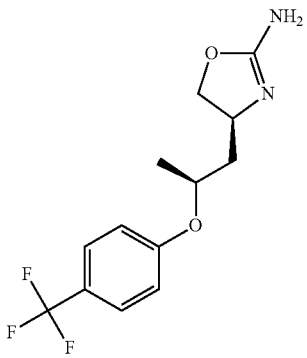 [SMILES: C[C@@H](C[C@H]1COC(N)=N1)Oc1ccc(C(F)(F)F)cc1]

The title compound was obtained in analogy to example 45 starting from (S)-4-(R)-2-hydroxy-propyl)-2,2-dimethyl-oxazolidine-3-carboxylic acid tert-butyl ester and 4-trifluoromethyl-phenol. White solid. MS (ISP): 289.1 ([M+H]$^+$).

EXAMPLE 79

(S)-4-[(S)-2-(4-Phenoxy-phenoxy)-propyl]-4,5-dihydro-oxazol-2-ylamine

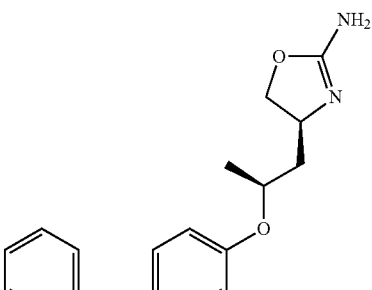

The title compound was obtained in analogy to example 45 starting from (S)-4-(R)-2-hydroxy-propyl)-2,2-dimethyl-oxazolidine-3-carboxylic acid tert-butyl ester and 4-phenoxyphenol. Light yellow viscous oil. MS (ISP): 313.1 ([M+H]$^+$).

EXAMPLE 80

(S)-4-[2-(Pyridin-2-yloxy)-ethyl]-4,5-dihydro-oxazol-2-ylamine

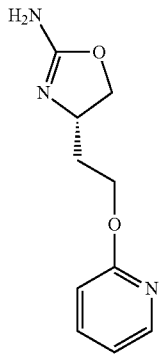 [SMILES: NC1=N[C@@H](CCOc2ccccn2)CO1]

The title compound was obtained in analogy to example 3 starting from 2-hydroxypyridine instead of 4-chlorophenol. Light yellow oil. MS (ISP): 299.2 ([M+H]$^+$)

EXAMPLE 81

(S)-4-[(S)-2-(4-Phenoxy-phenoxy)-propyl]-4,5-dihydro-oxazol-2-ylamine

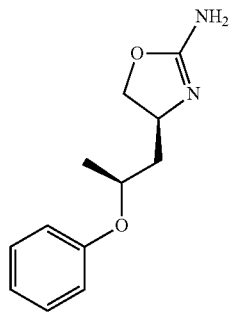 [SMILES: C[C@@H](C[C@H]1COC(N)=N1)Oc1ccccc1]

The title compound was obtained in analoy to example 45 starting from (S)-4-(R)-2-hydroxy-propyl)-2,2-dimethyl-oxazolidine-3-carboxylic acid tert-butyl ester and phenol. White solid. MS (ISP): 221.2 ([M+H]$^+$).

EXAMPLE 82

(S)-4-[(R)-2-(4-Fluoro-phenoxy)-propyl]-4,5-dihydro-oxazol-2-ylamine

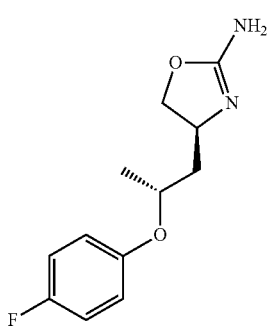 [SMILES: C[C@H](C[C@H]1COC(N)=N1)Oc1ccc(F)cc1]

The title compound was obtained in analogy to example 45 starting from (S)-4-(S)-2-hydroxy-propyl)-2,2-dimethyl-oxazolidine-3-carboxylic acid tert-butyl ester and 4-fluoro-phenol. Colourless viscous oil. MS (ISP): 239.1 ([M+H]$^+$).

EXAMPLE 83

(S)-4-[(R)-2-(3,4-Difluoro-phenoxy)-propyl]-4,5-dihydro-oxazol-2-ylamine

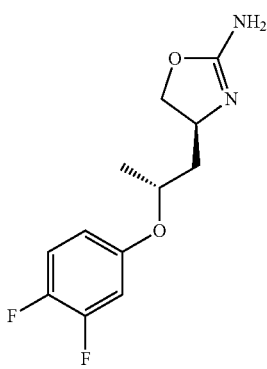 [SMILES: C[C@H](C[C@H]1COC(N)=N1)Oc1ccc(F)c(F)c1]

The title compound was obtained in analogy to example 45 starting from (S)-4-(S)-2-hydroxy-propyl)-2,2-dimethyl-oxazolidine-3-carboxylic acid tert-butyl ester and 3,4-difluoro-phenol. Colourless viscous oil. MS (ISP): 257.1 ([M+H]$^+$).

EXAMPLE 84

(S)-4-[(R)-2-(3-Chloro-phenoxy)-propyl]-4,5-dihydro-oxazol-2-ylamine

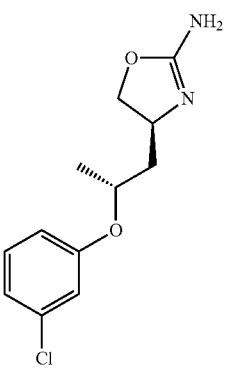 [SMILES: C[C@H](C[C@H]1COC(N)=N1)Oc1cccc(Cl)c1]

The title compound was obtained in analogy to example 45 starting from (S)-4-(S)-2-hydroxy-propyl)-2,2-dimethyl-oxazolidine-3-carboxylic acid tert-butyl ester and 3-chloro-phenol. Colourless viscous oil. MS (ISP): 257.2 ([{$^{37}$Cl}M+H]$^+$), 255.2 ([{$^{35}$Cl}M+H]$^+$).

EXAMPLE 85

(S)-4-[(R)-2-(3-Chloro-4-fluoro-phenoxy)-propyl]-4,5-dihydro-oxazol-2-ylamine

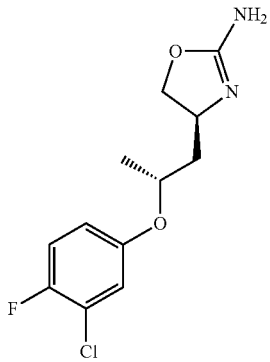 [SMILES: C[C@H](C[C@H]1COC(N)=N1)Oc1ccc(F)c(Cl)c1]

The title compound was obtained in analogy to example 45 starting from (S)-4-((S)-2-hydroxy-propyl)-2,2-dimethyl-oxazolidine-3-carboxylic acid tert-butyl ester and 3-chloro-4-fluoro-phenol. Colourless viscous oil. MS (ISP): 275.1 ([{$^{37}$Cl}M+H]$^+$), 273.2 ([{$^{35}$Cl}M+H]$^+$).

EXAMPLE 86

(S)-4-[(R)-2-(4-Bromo-phenoxy)-propyl]-4,5-dihydro-oxazol-2-ylamine

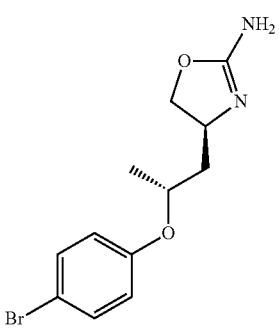

The title compound was obtained in analogy to example 45 starting from (S)-4-(S)-2-hydroxy-propyl)-2,2-dimethyl-oxazolidine-3-carboxylic acid tert-butyl ester and 4-bromo-phenol. Colourless viscous oil. MS (ISP): 301.0 ([{$^{81}$Br}M+H]$^+$), 299.1 ([{$^{79}$Br}M+H]$^+$).

EXAMPLE 87

(S)-4-[(R)-2-(4-Chloro-3-fluoro-phenoxy)-propyl]-4,5-dihydro-oxazol-2-ylamine

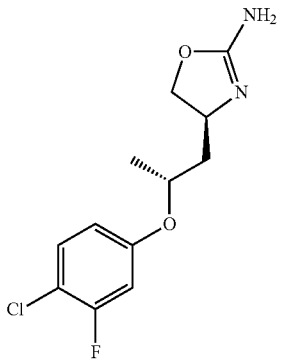 [SMILES: C[C@H](C[C@H]1COC(N)=N1)Oc1ccc(Cl)c(F)c1]

The title compound was obtained in analogy to example 45 starting from (S)-4-(S)-2-hydroxy-propyl)-2,2-dimethyl-oxazolidine-3-carboxylic acid tert-butyl ester and 4-chloro-3-fluoro-phenol. Colourless viscous oil. MS (ISP): 275.0 ([{$^{37}$Cl}M+H]$^+$), 273.1 ([{$^{35}$Cl}M+H]$^+$).

EXAMPLE 88

(S)-4-[2-(4-Trifluoromethyl-phenoxy)-ethyl]-4,5-dihydro-oxazol-2-ylamine

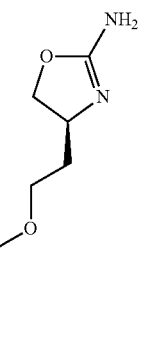

The title compound was obtained in analogy to example 3 starting from 4-trifluoromethyl-phenol instead of 4-chlorophenol. White crystalline solid. MS (ISP): 275.1 ([M+H]$^+$).

EXAMPLE 89

(S)-4-{2-[1-(2,4-Difluoro-phenyl)-cyclopropyl]-ethyl}-4,5-dihydro-oxazol-2-ylamine

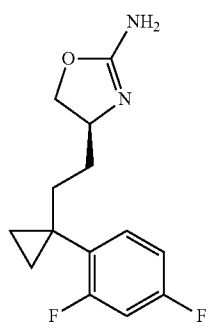 [SMILES: NC1=N[C@@H](CCC2(c3ccc(F)cc3F)CC2)CO1]

The title compound was obtained in analogy to example 30 starting from 1-(2,4-difluorophenyl)-cyclopropanecarbaldehyde instead of 1-(4-chloro-phenyl)-cyclopropanecarbaldehyde. Colourless oil. MS (ISP): 267.2 ([M+H]⁺).

EXAMPLE 90

(4S)-4-(1-Methyl-3-phenyl-propyl)-4,5-dihydro-oxazol-2-ylamine

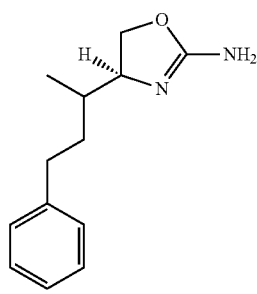 [SMILES: CC(CCc1ccccc1)[C@H]1COC(N)=N1]

The title compound was obtained in analogy to example 12 starting from 4-phenyl-butan-2-ol instead of 4,4,4-trifluoro-3-phenyl-butan-1-ol. White solid. MS (ISP): 219.3 ([M+H]⁺).

EXAMPLE 91

(S)-4-{2-[1-(3-Chloro-4-fluoro-phenyl)-cyclopropyl]-ethyl}-4,5-dihydro-oxazol-2-ylamine

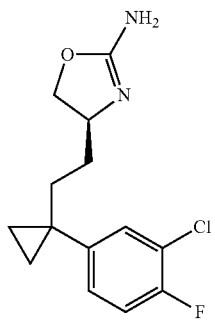 [SMILES: NC1=N[C@@H](CCC2(c3ccc(F)c(Cl)c3)CC2)CO1]

a) 1-(3-Chloro-4-fluoro-phenyl)-cyclopropanecarboitrile

To a mixture of 3-chloro-4-fluoro-phenylacetonitrile (8.48 g), 1,2-dibromoethane (13 ml) and benzyltriethylammonium chloride (0.46 g) was added sodium hydroxide solution (50% in water, 20 ml) at room temperature. The mixture was vigorously stirred overnight. Water was added and the aqueous phase was extracted twice with diethyl ether. The combined organic layers were washed with water and brine, dried over MgSO₄ and concentrated. The residue was purified by column chromatography (SiO₂; heptane/EtOAc) to give 1-(3-chloro-4-fluorophenyl)-cyclopropanecarbonitrile as light yellow liquid (3.91 g). ¹H-NMR (300 MHz, CDCl₃, δ): 1.35-1.40 (m, 2H), 1.72-1.76 (m, 2H), 7.10-7.21 (m, 2H), 7.26-7.34 (m, 1H).

b) 1-(3-Chloro-4-fluoro-phenyl)-cyclopropanecarbaldehyde

To a stirred, cooled (−78° C.) solution of 1-(3-chloro-4-fluoro-phenyl)cyclopropanecarbaldehyde (3.91 g) in toluene (140 ml) under an argon atmosphere was added slowly a solution of diisobutylaluminium hydride in toluene (20 ml; 1.2M in toluene). The mixture was stirred for 1 h, then the cooling bath was removed and the reaction mixture was quenched by adding an aqueous solution of Seignette salt. After stirring for 10 min ethyl acetate was added. The organic layer was separated, washed with brine, dried over MgSO₄ and concentrated. The residue was distilled in vacuo (Kugelrohr 160° C., 1 mbar) to give 1-(3-chloro-4-fluoro-phenyl)-cyclopropanecarbaldehyde as light brown liquid (1.28 g). ¹H-NMR (300 MHz, CDCl₃, δ): 1.36-1.40 (m, 2H), 1.57-1.63 (m, 2H), 6.81-6.89 (m, 2H), 7.15-7.26 (m, 1H), 9.03 (s, 1H).

c) (S)-4-{2-[1-(3-Chloro-4-fluoro-phenyl)-cyclopropyl]-ethyl}-4,5-dihydro-oxazol-2-ylamine The title compound was obtained in analogy to example 30 starting from 1-(3-chloro-4-fluoro-phenyl)-cyclopropanecarbaldehyde instead of 1-(4-chloro-phenyl)cyclopropanecarbaldehyde. White solid. MS (ISP): 283.1 ([M+H]⁺).

EXAMPLE 92

(S)-4-[3-(4-Chloro-phenyl)-3-methoxy-propyl]-4,5-dihydro-oxazol-2-ylamine

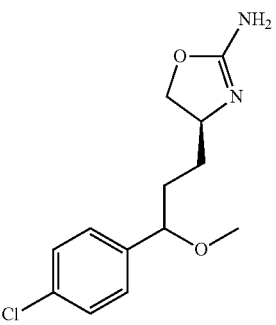 [SMILES: COC(CC[C@H]1COC(N)=N1)c1ccc(Cl)cc1]

a) (S)-4-[3-(4-Chloro-phenyl)-3-hydroxy-prop-1-ynyl]-2,2-dimethyl-oxazolidine-3-carboxylic acid tert-butyl ester

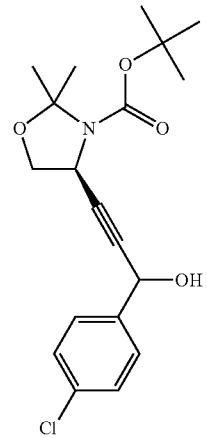 [SMILES: CC(C)(C)OC(=O)N1[C@@H](C#CC(O)c2ccc(Cl)cc2)COC1(C)C]

To a stirred solution of (S)-4-ethynyl-2,2-dimethyl-oxazolidine-3-carboxylic acid tert-butyl ester (3.16 g; CAS 173065-16-2) in dry THF (20 ml) under an argon atmosphere at −78° C. was added dropwise a solution of n-butyllithium in hexane (10.5 ml, 1.6 M solution) and stirring continued for 30 min. A solution of 4-chlorobenzaldehyde (2.17 g) in THF (10 ml) was added dropwise and the mixture was stirred for a further 2 h at −78° C. The reaction mixture was then quenched by careful addition of water (12 ml) and allowed to warm to room temperature. The mixture was diluted with ethyl acetate and washed with saturated brine. The combined organic phase was dried over sodium sulphate, filtered and concentrated in vacuo. The reside was purified by column chromatography (SiO$_2$; gradient: heptane/EtOAc) to give (S)-4-[3-(4-chloro-phenyl)-3-hydroxy-prop-1-ynyl]-2,2-dimethyl-oxazolidine-3-carboxylic acid tert-butyl ester (mixture of epimers) as a yellow oil. MS (ISP): 426.1 ([{$^{37}$Cl}M+OAc]$^-$), 424.1 ([{$^{35}$Cl}M+OAc]$^-$).

b) (S)-4-[3-(4-Chloro-phenyl)-3-methoxy-prop-1-vnyl]-2,2-dimethyl-oxazolidine-3-carboxylic acid tert-butyl ester

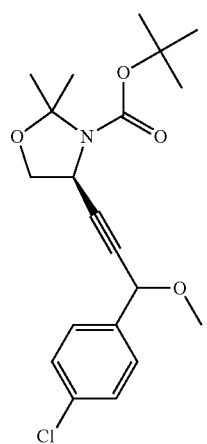 [SMILES: COC(C#C[C@H]1COC(C)(C)N1C(=O)OC(C)(C)C)c1ccc(Cl)cc1]

To (S)-4-[3-(4-chloro-phenyl)-3-hydroxy-prop-1-ynyl]-2,2-dimethyl-oxazolidine-3-carboxylic acid tert-butyl ester (3.10 g) was added dropwise iodomethane (5.27 ml). To the resulting yellow solution was added silver oxide (5.89 g) and the mixture was heated at 70° C. for 2 h. The reaction mixture was then cooled to room temperature and concentrated in vacuo. The residue was purified by column chromatography (SiO$_2$; gradient: heptane/EtOAc) to give (S)-4-[3-(4-chloro-phenyl)-3-methoxy-prop-1-ynyl]-2,2-dimethyl-oxazolidine-3-carboxylic acid tert-butyl ester (2.44 g, 76%) as a colourless oil. MS (ISP): 399.2 ([{$^{37}$Cl}M+NH$_4$]$^+$), 397.2 ([{$^{35}$Cl}M+NH$_4$]$^+$).

c) (S)-4-[3-(4-Chloro-phenyl)-3-methoxy-propyl]-2,2-dimethyl-oxazolidine-3-carboxylic acid tert-butyl ester

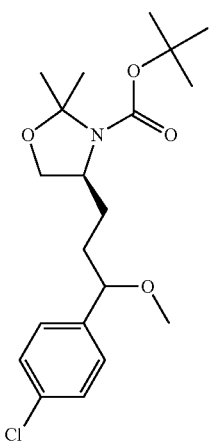 [SMILES: COC(CC[C@H]1COC(C)(C)N1C(=O)OC(C)(C)C)c1ccc(Cl)cc1]

To a solution of (S)-4-[3-(4-chloro-phenyl)-3-methoxy-prop-1-ynyl]-2,2-dimethyl-oxazolidine-3-carboxylic acid tert-butyl ester (2.50 g) in ethyl acetate (100 ml) at room temperature was added platinum(IV) oxide monohydrate (484 mg). The mixture was stirred under an atmosphere of hydrogen (1 atm) at room temperature for 1 h. The catalyst was removed by filtration and the filtrate was concentrated in vacuo to yield (S)-4-[3-(4-chloro-phenyl)-3-methoxy-propyl]-2,2-dimethyl-oxazolidine-3-carboxylic acid tert-butyl ester as a light yellow oil (1.57 g, 62%); MS (ISP): 386.2 ([{$^{37}$Cl}M+H]$^+$), 384.2 ([{$^{35}$Cl}M+H]$^+$).

d) (S)-2-Amino-5-(4-chloro-phenyl)-5-methoxy-pentan-1-ol

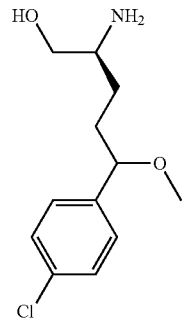 [SMILES: COC(CC[C@H](N)CO)c1ccc(Cl)cc1]

In analogy to example 45c (S)-4-[3-(4-chloro-phenyl)-3-methoxy-propyl]-2,2-dimethyl-oxazolidine-3-carboxylic acid tert-butyl ester was reacted with trifluoroacetic acid to give (S)-2-amino-5-(4-chloro-phenyl)-5-methoxy-pentan-1-ol. Yellow oil. MS (ISP): 246.1 ([{$^{37}$Cl}M+H]$^+$), 244.1 ([{$^{35}$Cl}M+H]$^+$).

e) (S)-4-[3-(4-Chloro-phenyl)-3-methoxy-propyl]-4,5-dihydro-oxazol-2-ylamine

In analogy to example 1d (S)-2-amino-5-(4-chloro-phenyl)-5-methoxy-pentan-1-ol was reacted with cyanogen bromide to give (S)-4-[3-(4-chloro-phenyl)-3-methoxy-propyl]-4,5-dihydro-oxazol-2-ylamine (mixture of epimers). White solid. MS (ISP): 271.2 ([{$^{37}$Cl}M+H]$^+$), 269.2 ([{$^{35}$Cl}M+H]$^+$).

EXAMPLE 93

(S)-4-[(R)-2-(2,4-Difluoro-phenoxy)-propyl]-4,5-dihydro-oxazol-2-ylamine

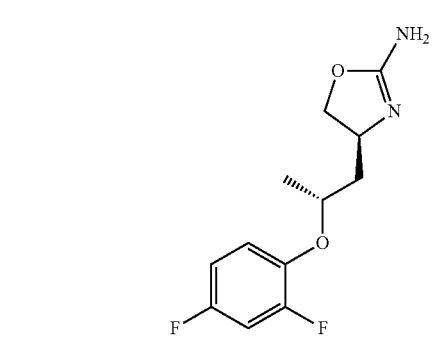 [SMILES: C[C@H](C[C@H]1COC(N)=N1)Oc1ccc(F)cc1F]

The title compound was obtained in analogy to example 45 starting from (S)-4-(S)-2-hydroxy-propyl)-2,2-dimethyl-oxazolidine-3-carboxylic acid tert-butyl ester and 2,4-difluoro-phenol. Colourless viscous oil. MS (ISP): 257.1 ([M+H]+).

EXAMPLE 94

(S)-4-[(R)-2-(4-Chloro-phenoxy)-butyl]-4,5-dihydro-oxazol-2-ylamine

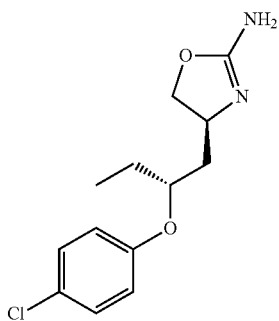 [SMILES: CC[C@H](C[C@H]1COC(N)=N1)Oc1ccc(Cl)cc1]

a) (S)-4-(R)-2-Hydroxy-butyl)-2,2-dimethyl-oxazolidine-3-carboxylic acid tert-butyl ester and (S)-4-((S)-2-Hydroxy-butyl)-2,2-dimethyl-oxazolidine-3-carboxylic acid tert-butyl ester

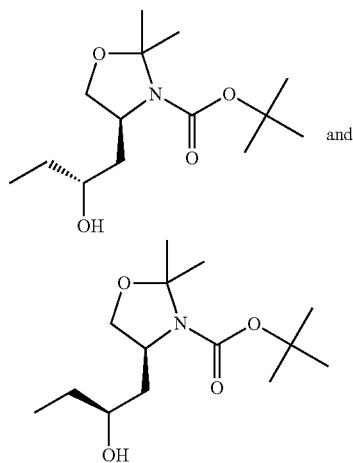

To a stirred solution of (S)-2,2-dimethyl-4-(2-oxo-ethyl)-oxazolidine-3-carboxylic acid tert-butyl ester (15.5 g; CAS 147959-19-1) in dry diethyl ether (100 ml) under an argon atmosphere at room temperature was added dropwise a solution of ethylmagnesium bromide in diethyl ether (42.6 ml, 3 M solution) and stirring continued for 1 hour. The reaction mixture was then quenched by careful addition of water (10 ml) and the mixture was then filtered through decalite. The filtrate was washed sequentially with water and with saturated brine and then the organic phase was separated, dried over sodium sulphate, filtered and concentrated in vacuo. The reside was purified by column chromatography (SiO$_2$; gradient: heptane/EtOAc 100:0→50:50) to give (S)-4-(R)-2-hydroxy-butyl)-2,2-dimethyl-oxazolidine-3-carboxylic acid tert-butyl ester (7.30 g) from fractions eluting first and (S)-4-(S)-2-hydroxy-butyl)-2,2-dimethyl-oxazolidine-3-carboxylic acid tert-butyl ester (6.44 g) from fractions eluting later, both compounds as colourless oils. (S)-4-(R)-2-Hydroxy-butyl)-2,2-dimethyl-oxazolidine-3-carboxylic acid tert-butyl ester: $^1$H NMR δ (CDCl$_3$, 300 MHz): 4.52 (1H, br. D, J=3.3 Hz), 4.23 (1H, m), 4.00 (1H, dd, J=8.7 & 5.4 Hz), 3.66 (1H, d, J=8.7 Hz), 3.40 (1H, m), 1.79 (1H, td, J=11.4 & 2.1 Hz), 1.60-1.44 (16H, m), 0.95 (3H, t, J=7.5 Hz). (S)-4-(S)-2-Hydroxy-butyl)-2,2-dimethyl-oxazolidine-3-carboxylic acid tert-butyl ester: $^1$H NMR δ (CDCl$_3$, 300 MHz): 4.12 (1H, m), 3.98 (1H, dd, J=9.0 & 5.7 Hz), 3.82 (1H, m), 3.55 (1H, m), 2.88 (1H, br. s), 1.79 (1H, m), 1.70-1.40 (16H, m), 0.95 (3H, t, J=7.5 Hz).

b) (S)-4-[(R)-2-(4-Chloro-phenoxy)-butyl]-4,5-dihydro-oxazol-2-ylamine

In analogy to example 45b-d (S)-4-((S)-2-hydroxy-butyl)-2,2-dimethyl-oxazolidine-3-carboxylic acid tert-butyl ester was reacted sequentially with 4-chlorophenyl, triphenylphosphine and di-tert-butyl azodicarboxylate, then with trifluoroacetic acid, and finally with cyanogen bromide to give (S)-4-[(R)-2-(4-chloro-phenoxy)-butyl]-4,5-dihydro-oxazol-2-ylamine.

Colourless gum. MS (ISP): 271.2 ([{$^{37}$Cl}M+H]+), 269.3 ([{$^{35}$Cl}M+H]+).

EXAMPLE 95

(S)-4-[(R)-2-(3-Chloro-phenoxy)-butyl]-4,5-dihydro-oxazol-2-ylamine

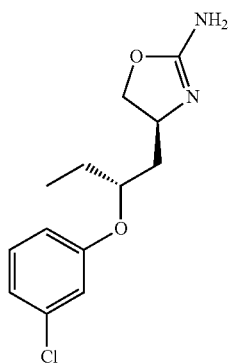 [SMILES: CC[C@H](C[C@H]1COC(N)=N1)Oc1cccc(Cl)c1]

The title compound was obtained in analogy to example 94 starting from (S)-4-(S)-2-hydroxy-butyl)-2,2-dimethyl-oxazolidine-3-carboxylic acid tert-butyl ester and 3-chloro-phenol. Colourless gum. MS (ISP): 271.3 ([{$^{37}$Cl}M+H]+), 269.2 ([{$^{35}$Cl}M+H]+).

EXAMPLE 96

(S)-4-[(R)-2-(3,4-Dichloro-phenoxy)-propyl]-4,5-dihydro-oxazol-2-ylamine

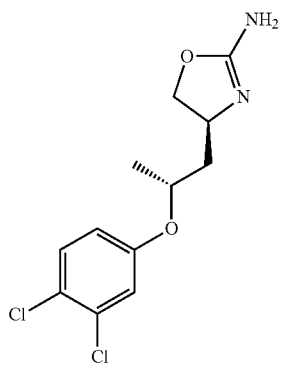

The title compound was obtained in analogy to example 45 starting from (S)-4-(S)-2-hydroxy-propyl)-2,2-dimethyl-oxazolidine-3-carboxylic acid tert-butyl ester and 3,4-dichlorophenol. Colourless viscous oil. MS (ISP): 293.0 ([{$^{37}$Cl}M+H]$^+$), 291.0 ([{$^{37}$Cl$^{35}$Cl}M+H]$^+$), 289.0 ([{$^{35}$Cl}M+H]$^+$).

EXAMPLE 97

(S)-4-((R)-2-Phenoxy-propyl)-4,5-dihydro-oxazol-2-ylamine

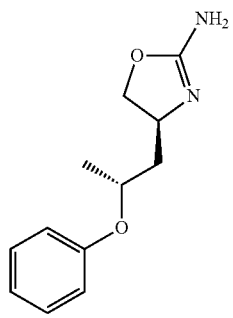 [SMILES: C[C@H](C[C@H]1COC(N)=N1)Oc1ccccc1]

The title compound was obtained in analogy to example 45 starting from (S)-4-((S)-2-hydroxy-propyl)-2,2-dimethyl-oxazolidine-3-carboxylic acid tert-butyl ester and phenol. Colourless gum. MS (ISP): 221.2 ([M+H]$^+$).

EXAMPLE 98

(S)-4-[3-(4-Chloro-phenyl)-3-ethoxy-propyl]-4,5-dihydro-oxazol-2-ylamine

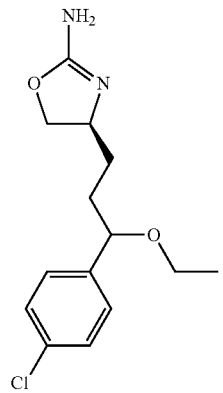 [SMILES: CCOC(CC[C@H]1COC(N)=N1)c1ccc(Cl)cc1]

The title compound was obtained as an epimeric mixture in analogy to example 92 by using (S)-4-ethynyl-2,2-dimethyl-oxazolidine-3-carboxylic acid tert-butyl ester, 4-chlorobenzaldehyde and iodoethane. Colourless oil. MS (ISP): 285.0 ([{$^{37}$Cl}M+H]$^+$), 283.1 ([{$^{35}$Cl}M+H]$^+$).

EXAMPLE 99

(S)-4-(3-Ethoxy-3-phenyl-propyl)-4,5-dihydro-oxazol-2-ylamine

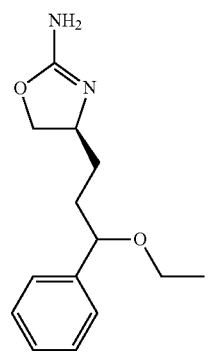 [SMILES: CCOC(CC[C@H]1COC(N)=N1)c1ccccc1]

The title compound was obtained as an epimeric mixture in analogy to example 92 by using (S)-4-ethynyl-2,2-dimethyl-oxazolidine-3-carboxylic acid tert-butyl ester, benzaldehyde and iodoethane. Colourless oil. MS (ISP): 249.1 ([M+H]$^+$).

EXAMPLES 100 & 101

(S)-4-[(S)-3-(4-Chloro-phenyl)-3-methoxy-propyl]-4,5-dihydro-oxazol-2-ylamine & (S)-4-[(R)-3-(4-Chloro-phenyl)-3-methoxy-propyl]-4,5-dihydro-oxazol-2-ylamine

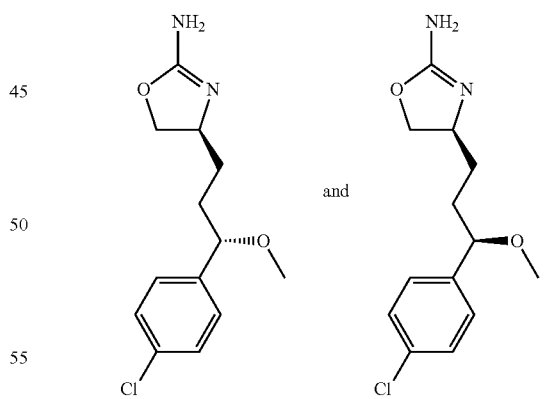

(S)-4-[3-(4-Chloro-phenyl)-3-methoxy-propyl]-4,5-dihydro-oxazol-2-ylamine (mixture of epimers, example 92) was separated using chiral HPLC (column: chiralpak AD, eluant: 7% ethanol (containing 0.01 M ammonium chloride) in heptane, flow-rate: 35 ml/min) to afford stereochemically pure samples of (S)-4-[(S)-3-(4-Chloro-phenyl)-3-methoxy-propyl]-4,5-dihydro-oxazol-2-ylamine & (S)-4-[(R)-3-(4-Chloro-phenyl)-3-methoxy-propyl]-4,5-dihydro-oxazol-2-ylamine. Retention times: (−)-enantiomer 112 min (example 100) and (+)-enantiomer 122 min (example 101). Both white crystalline solids. MS (ISP): 271.1 ([{$^{37}$Cl}M+H]$^+$), 269.1 ([{$^{35}$Cl}M+H]$^+$).

EXAMPLES 102 & 103

(S)-4-[(S)-3-(Phenyl)-3-methoxy-propyl]-4,5-dihydro-oxazol-2-ylamine & (S)-4-[(R)-3-(Phenyl)-3-methoxy-propyl]-4,5-dihydro-oxazol-2-ylamine

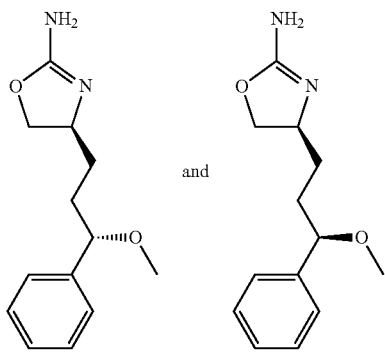 [SMILES: CO[C@@H](CC[C@H]1COC(N)=N1)c1ccccc1 ; CO[C@H](CC[C@H]1COC(N)=N1)c1ccccc1]

The title compounds were obtained in analogy to example 141 starting from (S)-4-[(S)-3-(4-chloro-phenyl)-3-methoxy-propyl]-4,5-dihydro-oxazol-2-ylamine & (S)-4-[(R)-3-(4-chlorophenyl)-3-methoxy-propyl]-4,5-dihydro-oxazol-2-ylamine in place of (S)-4-[(R)-2-(3-benzyloxy-phenoxy)-butyl]-4,5-dihydro-oxazol-2-ylamine. Both white crystalline solids. MS (ISP): 235.1 ([M+H]$^+$).

EXAMPLE 104

4-[(R)-2-(4-Fluoro-phenoxy)-1-methyl-ethyl]-4,5-dihydro-oxazol-2-ylamine

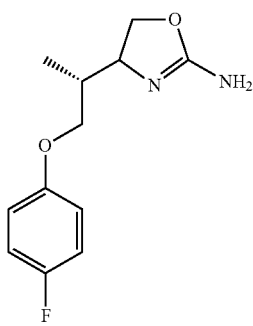 [SMILES: C[C@@H](COc1ccc(F)cc1)C1COC(N)=N1]

The title compound was obtained in analogy to example 12 starting from (S)-1-(4-fluorophenoxy-propan-2-ol instead of 4,4,4-trifluoro-3-phenyl-butan-1-ol. White solid. MS (ISP): 239.1 ([M+H]$^+$).

EXAMPLE 105

4-[(S)-2-(4-Fluoro-phenoxy)-1-methyl-ethyl]-4,5-dihydro-oxazol-2-ylamine

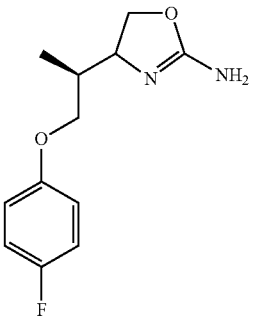 [SMILES: C[C@H](COc1ccc(F)cc1)C1COC(N)=N1]

The title compound was obtained in analogy to example 12 starting from (R)-1-(4-fluorophenoxy-propan-2-ol instead of 4,4,4-trifluoro-3-phenyl-butan-1-ol. Off-white solid. MS (ISP): 239.1 ([M+H]$^+$).

EXAMPLE 106

(S)-4-[(R)-2-(4-Chloro-2-fluoro-phenoxy)-propyl]-4,5-dihydro-oxazol-2-ylamine

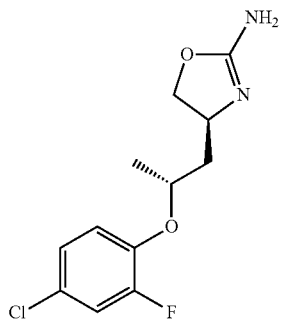 [SMILES: C[C@H](C[C@H]1COC(N)=N1)Oc1ccc(Cl)cc1F]

The title compound was obtained in analogy to example 45 starting from (S)-4-(S)-2-hydroxy-propyl)-2,2-dimethyl-oxazolidine-3-carboxylic acid tert-butyl ester and 4-chloro-2-fluoro-phenol. Colourless gum. MS (ISP): 275.0 ([{$^{37}$Cl}M+H]$^+$), 273.1 ([{$^{35}$Cl}M+H]$^+$).

EXAMPLE 107

(S)-4-[(S)-2-(4-Chloro-phenoxy)-butyl]-4,5-dihydro-oxazol-2-ylamine

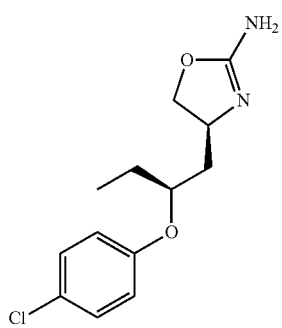 [SMILES: CC[C@@H](C[C@H]1COC(N)=N1)Oc1ccc(Cl)cc1]

The title compound was obtained in analogy to example 94 starting from (S)-4-(R)-2-hydroxy-butyl)-2,2-dimethyl-oxazolidine-3-carboxylic acid tert-butyl ester and 4-chloro-phenol. Colourless viscous oil. MS (ISP): 271.3 ([{$^{37}$Cl}M+H]$^+$), 269.2 ([{$^{35}$Cl}M+H]$^+$).

EXAMPLE 108

(S)-4-{2-[1-(3,4-Difluoro-phenyl)-cyclopropyl]-ethyl}-4,5-dihydro-oxazol-2-ylamine

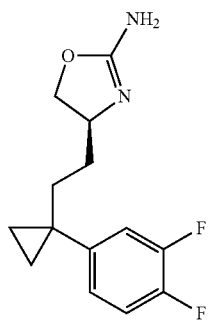 [SMILES: NC1=N[C@@H](CCC2(c3ccc(F)c(F)c3)CC2)CO1]

The title compound was obtained in analogy to example 91 starting from 3,4-difluorophenylacetonitrile instead of 3-chloro-4-fluoro-phenylacetonitrile. White solid. MS (ISP): 267.2 ([M+H]$^+$).

EXAMPLE 109

(S)-4-((S)-2-Phenoxy-butyl)-4,5-dihydro-oxazol-2-ylamine

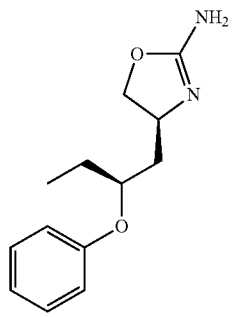 [SMILES: CC[C@@H](C[C@H]1COC(N)=N1)Oc1ccccc1]

The title compound was obtained in analogy to example 94 starting from (S)-4-(R)-2-hydroxy-butyl)-2,2-dimethyl-oxazolidine-3-carboxylic acid tert-butyl ester and phenol. Colourless viscous oil. MS (ISP): 235.2 ([M+H]$^+$).

EXAMPLE 110

(S)-4-{2-[1-(4-Chloro-phenyl)-cyclobutyl]-ethyl}-4,5-dihydro-oxazol-2-ylamine

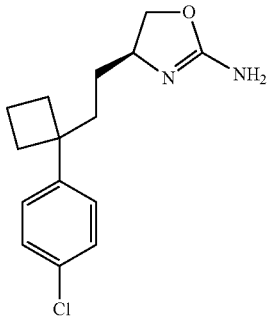 [SMILES: NC1=N[C@@H](CCC2(c3ccc(Cl)cc3)CCC2)CO1]

The title compound was obtained in analogy to example 30 starting from 1-(4-chlorophenyl)-cyclobutanecarbaldehyde instead of 1-(4-chloro-phenyl)-cyclopropanecarbaldehyde. Light yellow solid. MS (ISP): 279.1 ([M+H]$^+$).

EXAMPLE 111

(S)-4-[(S)-2-(4-Bromo-phenoxy)-butyl]-4,5-dihydro-oxazol-2-ylamine

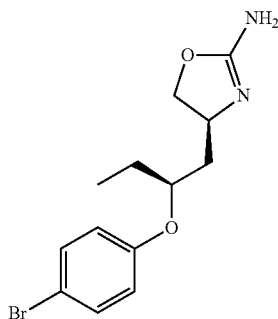

The title compound was obtained in analogy to example 94 starting from (S)-4-((R)-2-hydroxy-butyl)-2,2-dimethyl-oxazolidine-3-carboxylic acid tert-butyl ester and 4-bromo-phenol. Colourless viscous oil. MS (ISP): 314.9 ([{$^{81}$Br}M+H]$^+$), 313.0 ([{$^{79}$Br}M+H]$^+$).

EXAMPLE 112

((S)-4-[(S)-2-(3-Chloro-phenoxy)-butyl]-4,5-dihydro-oxazol-2-ylamine

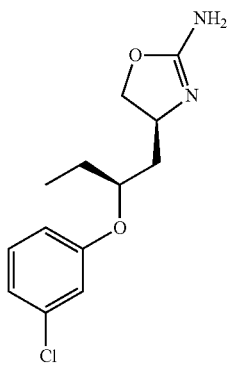 [SMILES: CC[C@@H](C[C@H]1COC(N)=N1)Oc1cccc(Cl)c1]

The title compound was obtained in analogy to example 94 starting from (S)-4-(R)-2-hydroxy-butyl)-2,2-dimethyl-oxazolidine-3-carboxylic acid tert-butyl ester and 3-chloro-phenol. Colourless viscous oil. MS (ISP): 271.3 ([{$^{37}$Cl}M+H]$^+$), 269.2 ([{$^{35}$Cl}M+H]$^+$).

EXAMPLE 113

(S)-4-[(S)-2-(4-Chloro-3-fluoro-phenoxy)-butyl]-4,5-dihydro-oxazol-2-ylamine

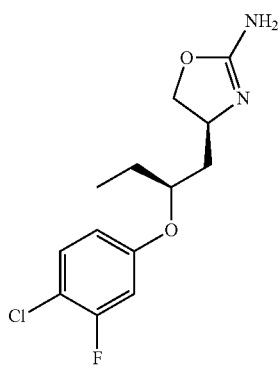 [SMILES: CC[C@@H](C[C@H]1COC(N)=N1)Oc1ccc(Cl)c(F)c1]

The title compound was obtained in analogy to example 94 starting from (S)-4-(R)-2-hydroxy-butyl)-2,2-dimethyl-oxazolidine-3-carboxylic acid tert-butyl ester and 4-chloro-3-fluoro-phenol. Colourless viscous oil. MS (ISP): 288.9 ([{$^{37}$Cl}M+H]$^+$), 287.0 ([{$^{35}$Cl}M+H]$^+$).

EXAMPLE 114

(S)-4-[(S)-2-(2,4-Difluoro-phenoxy)-butyl]-4,5-dihydro-oxazol-2-ylamine

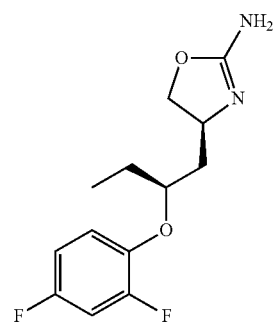 [SMILES: CC[C@@H](C[C@H]1COC(N)=N1)Oc1ccc(F)cc1F]

The title compound was obtained in analogy to example 94 starting from (S)-4-(R)-2-hydroxy-butyl)-2,2-dimethyl-oxazolidine-3-carboxylic acid tert-butyl ester and 2,4-difluoro-phenol. Colourless viscous oil. MS (ISP): 271.2 ([M+H]$^+$).

EXAMPLE 115

(S)-4-[(S)-3-(4-Fluoro-phenyl)-butyl]-4,5-dihydro-oxazol-2-ylamine

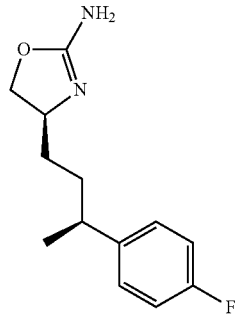 [SMILES: C[C@@H](CC[C@H]1COC(N)=N1)c1ccc(F)cc1]

The title compound was obtained in analogy to example 12 starting from (S)-3-(4-fluorophenyl)-butan-1-ol (synthesized according to a procedure described in J. Org. Chem. 2005, 70, 4133) instead of 4,4,4-trifluoro-3-phenyl-butan-1-ol. Colourless oil. MS (ISP): 237.1 ([M+H]$^+$).

EXAMPLE 116

(S)-4-[(R)-3-(4-Fluoro-phenyl)-butyl]-4,5-dihydro-oxazol-2-ylamine

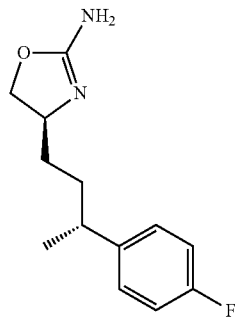 [SMILES: C[C@H](CC[C@H]1COC(N)=N1)c1ccc(F)cc1]

The title compound was obtained in analogy to example 12 starting from (R)-3-(4-fluorophenyl)-butan-1-ol (synthesized according to a procedure described in J. Org. Chem. 2005, 70, 4133) instead of 4,4,4-trifluoro-3-phenyl-butan-1-ol. Colourless oil. MS (ISP): 237.1 ([M+H]$^+$).

EXAMPLE 117

(S)-4-[(S)-2-(4-Fluoro-phenoxy)-butyl]-4,5-dihydro-oxazol-2-ylamine

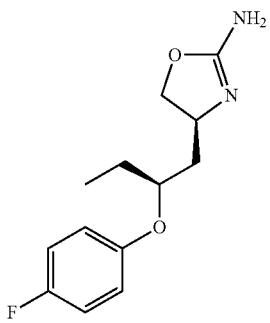 [SMILES: CC[C@@H](C[C@H]1COC(N)=N1)Oc1ccc(F)cc1]

113

The title compound was obtained in analogy to example 94 starting from (S)-4-(R)-2-hydroxy-butyl)-2,2-dimethyl-oxazolidine-3-carboxylic acid tert-butyl ester and 4-fluoro-phenol. Colourless viscous oil. MS (ISP): 253.1 ([M+H]$^+$).

EXAMPLE 118

(4S)-4-(2-Benzyl-butyl)-4,5-dihydro-oxazol-2-ylamine

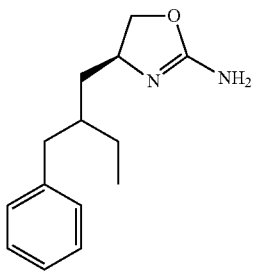 [SMILES: CCC(Cc1ccccc1)C[C@H]1COC(N)=N1]

The title compound was obtained in analogy to example 12 starting from 2-benzyl-butan-1-ol instead of 4,4,4-trifluoro-3-phenyl-butan-1-ol. Colourless oil. MS (ISP): 233.1 ([M+H]$^+$).

EXAMPLE 119

(S)-4-[(S)-2-(3,4-Difluoro-phenoxy)-butyl]-4,5-dihydro-oxazol-2-ylamine

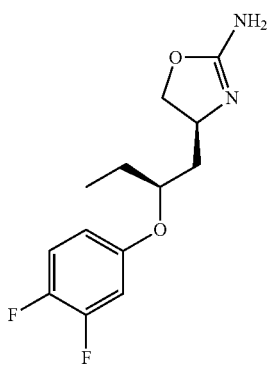 [SMILES: CC[C@@H](C[C@H]1COC(N)=N1)Oc1ccc(F)c(F)c1]

The title compound was obtained in analogy to example 94 starting from (S)-4-(R)-2-hydroxy-butyl)-2,2-dimethyl-oxazolidine-3-carboxylic acid tert-butyl ester and 3,4-difluorophenol. Colourless viscous oil. MS (ISP): 271.2 ([M+H]$^+$).

114

EXAMPLE 120

(S)-4-[(S)-2-(3-Chloro-4-fluoro-phenoxy)-butyl]-4,5-dihydro-oxazol-2-ylamine

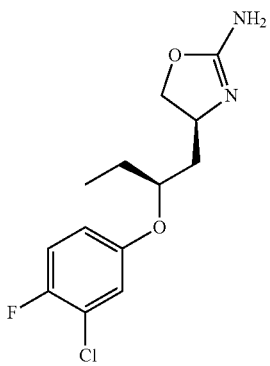 [SMILES: CC[C@@H](C[C@H]1COC(N)=N1)Oc1ccc(F)c(Cl)c1]

The title compound was obtained in analogy to example 94 starting from (S)-4-(R)-2-hydroxy-butyl)-2,2-dimethyl-oxazolidine-3-carboxylic acid tert-butyl ester and 3-chloro-4-fluoro-phenol. Colourless viscous oil. MS (ISP): 288.9 ([{$^{37}$Cl}M+H]$^+$), 287.0 ([{$^{35}$Cl}M+H]$^+$).

EXAMPLE 121

(S)-4-[(S)-2-(4-Trifluoromethyl-phenoxy)-butyl]-4,5-dihydro-oxazol-2-ylamine

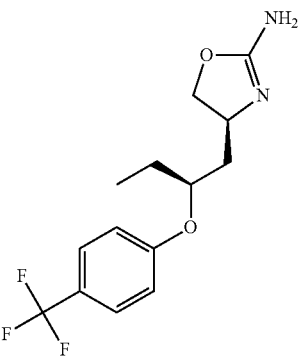 [SMILES: CC[C@@H](C[C@H]1COC(N)=N1)Oc1ccc(C(F)(F)F)cc1]

The title compound was obtained in analogy to example 94 starting from (S)-4-(R)-2-hydroxy-butyl)-2,2-dimethyl-oxazolidine-3-carboxylic acid tert-butyl ester and 4-trifluoromethyl-phenol. Colourless viscous oil. MS (ISP): 303.1 ([M+H]$^+$).

EXAMPLE 122

(S)-4-[(S)-2-(3,4-Dichloro-phenoxy)-butyl]-4,5-dihydro-oxazol-2-ylamine

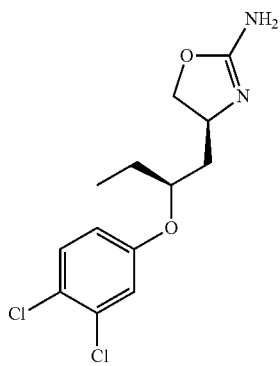 [SMILES: CC[C@@H](C[C@H]1COC(N)=N1)Oc1ccc(Cl)c(Cl)c1]

The title compound was obtained in analogy to example 94 starting from (S)-4-(R)-2-hydroxy-butyl)-2,2-dimethyl-oxazolidine-3-carboxylic acid tert-butyl ester and 3,4-dichlorophenol. Colourless viscous oil. MS (ISP): 307.1 ([{$^{37}$Cl}M+H]$^+$), 305.0 ([{$^{37}$Cl$^{35}$Cl}M+H]$^+$), 303.0 ([{$^{35}$Cl}M+H]$^+$).

EXAMPLE 123

(S)-4-[(S)-2-(4-Chloro-2-fluoro-phenoxy)-butyl]-4,5-dihydro-oxazol-2-ylamine

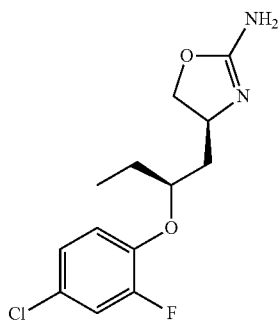 [SMILES: CC[C@@H](C[C@H]1COC(N)=N1)Oc1ccc(Cl)cc1F]

The title compound was obtained in analogy to example 94 starting from (S)-4-(R)-2-hydroxy-butyl)-2,2-dimethyl-oxazolidine-3-carboxylic acid tert-butyl ester and 4-chloro-2-fluoro-phenol. Colourless gum. MS (ISP): 288.9 ([{$^{37}$Cl}M+H]$^+$), 287.0 ([{35Cl}M+H]$^+$).

EXAMPLE 124

(4S)-4-[3-(3,5-Difluoro-phenyl)-pentyl]-4,5-dihydro-oxazol-2-ylamine

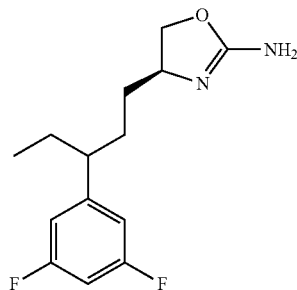 [SMILES: CCC(CC[C@H]1COC(N)=N1)c1cc(F)cc(F)c1]

a) (S)-4-{(Z)-2-[1-(3,5-Difluoro-phenyl)-cyclopropyl]-vinyl}-2,2-dimethyl-oxazolidine-3-carboxylic acid tert-butyl ester was obtained in analogy to example 30c starting from 143,5-difluoro-phenyl)-cyclopropanecarbaldehyde (obtained as described in example 91b, see also example 142) instead of 1-(4-chloro-phenyl)-cyclopropanecarbaldehyde. Light yellow oil. MS (ISP): 380.3 ([M+H]$^+$).

b) (S)-4-[3-(3,5-Difluoro-phenyl)-pentyl]-2,2-dimethyl-oxazolidine-3-carboxylic acid tert-butyl ester To a stirred solution of (S)-4-{(Z)-2-[1-(3,5-difluoro-phenyl)-cyclopropyl]-vinyl}-2,2-dimethyl-oxazolidine-3-carboxylic acid tert-butyl ester (0.5 g) at room temperature in methanol (10 ml) under an argon atmosphere were added palladium on charcoal (10%, 30 mg) and ammonium formate (1.33 g). The mixture was stirred at room temperature overnight. The catalyst was filtered off, the filtrate was concentrated, ethyl acetate was added and the mixture was washed with water. The organic layer was separated, dried over magnesium sulphate and concentrated to give (S)-4-[3-(3,5-difluoro-phenyl)-pentyl]-2,2-dimethyl-oxazolidine-3-carboxylic acid tert-butyl ester (0.5 g) as a light yellow liquid. MS (ISP): 384.3 ([M+H]$^+$).

c) (S)-2-Amino-5-(3,5-difluoro-phenyl)-heptan-1-ol

To (S)-4-[3-(3,5-difluoro-phenyl)-pentyl]-2,2-dimethyl-oxazolidine-3-carboxylic acid tert-butyl ester (0.5 g) was added under an argon atmosphere 5.5 M HCl solution in ethanol (2 ml). The mixture was stirred for 16 h. The mixture was concentrated. The residue was dissolved in dichloromethane and an excess of ammonia in methanol and some silica gel was added. The solvents were evaporated and the crude product was purified by column chromatography (column: Isolute® Flash-NH$_2$ from Separtis; eluent: dichloromethane/methanol=90:10) to give (S)-2-amino-5-(3,5-difluoro-phenyl)-heptan-1-ol (0.27 g) as a colourless liquid. MS (ISP): 244.3 ([M+H]$^+$).

d) (4S)-4-[3-(3,5-Difluoro-phenyl)-p entyl]-4,5-dihydro-oxazol-2-ylamine

In analogy to example 1d (S)-2-amino-5-(3,5-difluoro-phenyl)-heptan-1-ol was reacted with cyanogen bromide to give (4S)-4-[3-(3,5-difluoro-phenyl)-pentyl]-4,5-dihydro-oxazol-2-ylamine. Light yellow liquid. MS (ISP): 269.3 ([M+H]+).

EXAMPLE 125

(S)-4-[(R)-2-(4-Trifluoromethyl-phenoxy)-propyl]-4,5-dihydro-oxazol-2-ylamine

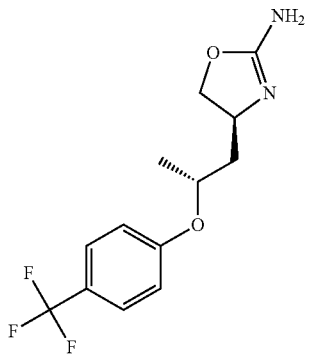 [SMILES: C[C@H](C[C@H]1COC(N)=N1)Oc1ccc(C(F)(F)F)cc1]

The title compound was obtained in analogy to example 45 starting from (S)-4-(S)-2-hydroxy-propyl)-2,2-dimethyl-oxazolidine-3-carboxylic acid tert-butyl ester and 4-trifluoromethyl-phenol. Light yellow viscous oil. MS (ISP): 289.1 ([M+H]+).

EXAMPLE 126

3-[2-((S)-2-Amino-4,5-dihydro-oxazol-4-yl)-ethoxy]-phenol

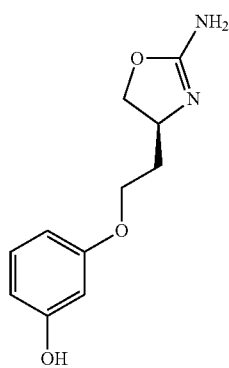 [SMILES: NC1=N[C@@H](CCOc2cccc(O)c2)CO1]

To a stirred solution of (S)-4-[2-(3-benzyloxy-phenoxy)-ethyl]-4,5-dihydro-oxazol-2-ylamine (0.04 g) at room temperature in methanol (2 ml) under an argon atmosphere was added palladium on charcoal (10%, 15 mg). The mixture was stirred at room temperature under a hydrogen atmosphere for 1 hour. The catalyst was filtered off, the filtrate was concentrated and purified by column chromatography to give 3424 (S)-[2-amino-4,5-dihydro-oxazol-4-yl)-ethoxy]-phenol (0.018 g) as a light yellow oil. MS (ISP): 223.3 ([M+H]+).

EXAMPLE 127

3-[2-((S)-2-Amino-4,5-dihydro-oxazol-4-yl)-ethoxy]-benzoic acid methyl ester

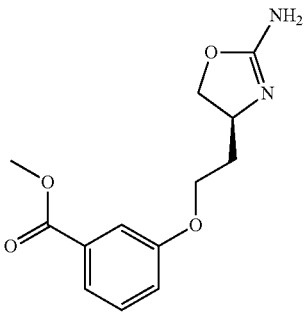 [SMILES: COC(=O)c1cccc(OCC[C@H]2COC(N)=N2)c1]

The title compound was obtained in analogy to example 3 starting from methyl 3-hydroxybenzoate instead of 4-chlorophenol. Orange viscous oil. MS (ISP): 265.1 ([M+H]+).

EXAMPLE 128

(S)-4-[2-(3-Tetrazol-1-yl-phenoxy)-ethyl]-4,5-dihydro-oxazol-2-ylamine

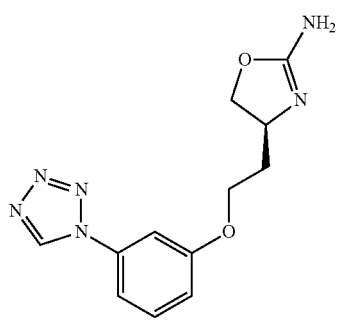 [SMILES: NC1=N[C@@H](CCOc2cccc(-n3cnnn3)c2)CO1]

The title compound was obtained in analogy to example 3 starting from 3-tetrazol-1-ylphenol instead of 4-chlorophenol. Colourless gum. MS (ISP): 275.1 ([M+H]+).

EXAMPLE 129

(S)-4-[2-(3-Methanesulfonyl-phenoxy)-ethyl]-4,5-dihydro-oxazol-2-ylamine

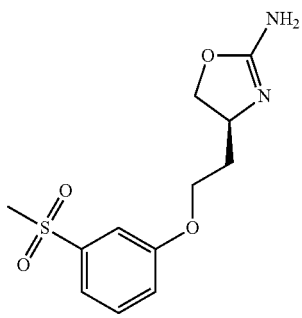 [SMILES: CS(=O)(=O)c1cccc(OCC[C@H]2COC(N)=N2)c1]

The title compound was obtained in analogy to example 3 starting from 3-methanesulfonyl-phenol instead of 4-chlorophenol. White solid. MS (ISP): 285.1 ([M+H]+).

EXAMPLE 130

(S)-4-[2-(3,5-Difluoro-phenoxy)-ethyl]-4,5-dihydro-oxazol-2-ylamine

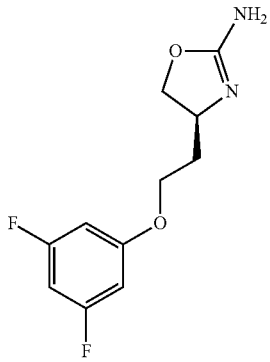 [SMILES: NC1=N[C@@H](CCOc2cc(F)cc(F)c2)CO1]

The title compound was obtained in analogy to example 3 starting from 3,5-difluorophenol instead of 4-chlorophenol. White solid. MS (ISP): 243.3 ([M+H]+).

EXAMPLE 131

(S)-4-[2-(5-Trifluoromethyl-pyridin-2-yloxy)-ethyl]-4,5-dihydro-oxazol-2-ylamine

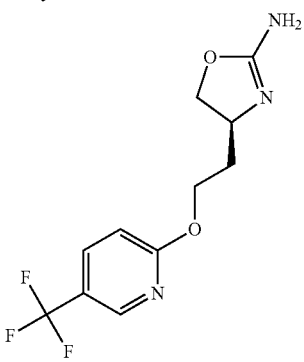

a) (S)-2,2-Dimethyl-[2-(5-trifluoromethyl-pyridin-2-yloxy)-ethyl]-oxazolidine-3-carboxylic acid tert-butyl ester

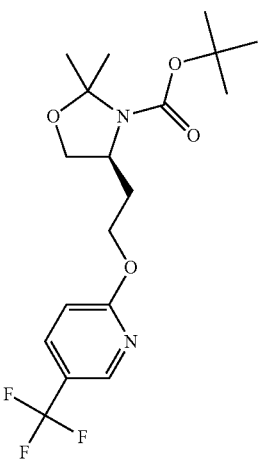 [SMILES: CC(C)(C)OC(=O)N1[C@@H](CCOc2ccc(C(F)(F)F)cn2)COC1(C)C]

To a stirred solution of tert-butyl (S)-4-(2-hydroxyethyl)-2,2-dimethyl-oxazolidine-3-carboxylate (300 mg; CAS 147959-18-0) in THF (4 ml) under an argon atmosphere was added sodium hydride (59 mg, 60% dispersion in oil). The resulting suspension was heated at 50° C. for 20 min and then cooled to 0° C. A solution of 2-chloro-5-trifluoromethyl-pyridine (222 mg) in THF (2 ml) was then added dropwise and the resulting mixture was heated at 70° C. for 3 h. The reaction mixture was cooled to room temperature and diluted with ethyl acetate. The mixture was washed with saturated brine, the phases were separated and the organic phase was dried over sodium sulphate and concentrated in vacuo. The residue was purified by column chromatography (SiO$_2$; gradient: heptane/EtOAc) to give (S)-2,2-dimethyl-4-[2-(5-trifluoromethyl-pyridin-2-yloxy)-ethyl]-oxazolidine-3-carboxylic acid tert-butyl ester (393 mg, 82%) as a colourless oil. MS (ISP): 391.3 ([M+H]+).

b) (S)-2-Amino-4-(5-trifluoromethyl-pyridin-2-yloxy)-butan-1-ol

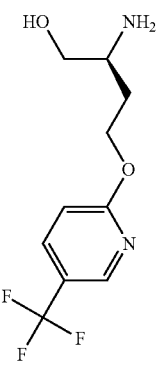 [SMILES: N[C@H](CO)CCOc1ccc(C(F)(F)F)cn1]

To a solution of trifluoroacetic acid (0.23 ml) in water (9 ml) was added dropwise a solution of (S)-2,2-dimethyl-4-[2-(5-trifluoromethyl-pyridin-2-yloxy)-ethyl]-oxazolidine-3-carboxylic acid tert-butyl ester (390 mg) in acetonitrile (1.5 ml). The mixture was heated for 90 min at 80° C. with stirring. The mixture was then cooled to room temperature and made basic by addition of 2 M aq. sodium hydroxide solution, then diluted with ethyl acetate and washed sequentially with water and with saturated brine. The organic phase was separated, dried over sodium sulphate and concentrated in vacuo to give (S)-2-amino-4-(5-trifluoromethyl-pyridin-2-yloxy)-butan-1-ol (284 mg, quant.) as a yellow oil. MS (ISP): 251.2 ([M+H]+).

c) (S)-4-[2-(5-Trifluoromethyl-pyridin-2-yloxy)-ethyl]-4,5-dihydro-oxazol-2-ylamine In analogy to example 1d (S)-2-amino-4-(5-trifluoromethyl-pyridin-2-yloxy)-butan-1-ol was reacted with cyanogen bromide to give (S)-4-[2-(5-trifluoromethyl-pyridin-2-yloxy)-ethyl]-4,5-dihydro-oxazol-2-ylamine. White solid. MS (ISP): 276.2 ([M+H]+).

EXAMPLE 132

(S)-4-[(S)-2-(5-Trifluoromethyl-pyridin-2-yloxy)-propyl]-4,5-dihydro-oxazol-2-ylamine

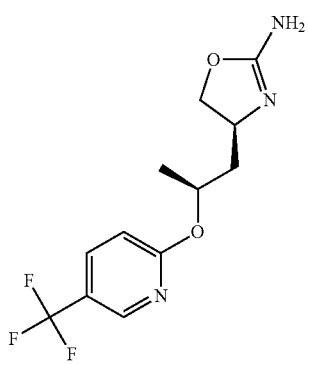

The title compound was obtained in analogy to example 131 starting from (S)-4-(S)-2-hydroxy-propyl)-2,2-dimethyl-oxazolidine-3-carboxylic acid tert-butyl ester and 2-chloro-5-trifluoromethyl-pyridine. White solid. MS (ISP): 290.1 ([M+H]$^+$).

EXAMPLE 133

(S)-4-[(R)-2-(5-Trifluoromethyl-pyridin-2-yloxy)-butyl]-4,5-dihydro-oxazol-2-ylamine

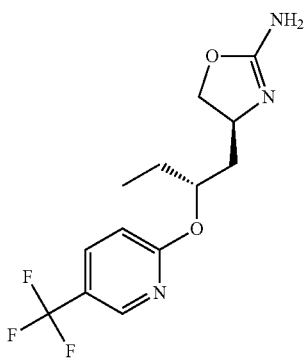 [SMILES: CC[C@H](C[C@H]1COC(N)=N1)Oc1ccc(C(F)(F)F)cn1]

The title compound was obtained in analogy to example 131 starting from (S)-4-(R)-2-hydroxy-butyl)-2,2-dimethyl-oxazolidine-3-carboxylic acid tert-butyl ester and 2-chloro-5-trifluoromethyl-pyridine. Colourless oil. MS (ISP): 304.1 ([M+H]$^+$).

EXAMPLE 134

(S)-4-[(S)-2-(5-Trifluoromethyl-pyridin-2-yloxy)-butyl]-4,5-dihydro-oxazol-2-ylamine

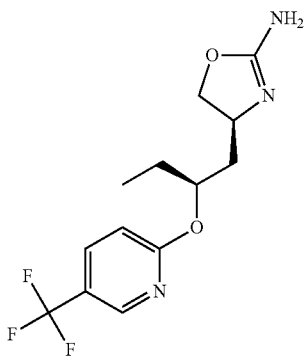

The title compound was obtained in analogy to example 131 starting from (S)-4-((S)-2-hydroxy-butyl)-2,2-dimethyl-oxazolidine-3-carboxylic acid tert-butyl ester and 2-chloro-5-trifluoromethyl-pyridine. Colourless oil. MS (ISP): 304.1 ([M+H]$^+$).

EXAMPLE 135

(S)-4-[2-(6-Trifluoromethyl-pyridin-3-yloxy)-ethyl]-4,5-dihydro-oxazol-2-ylamine

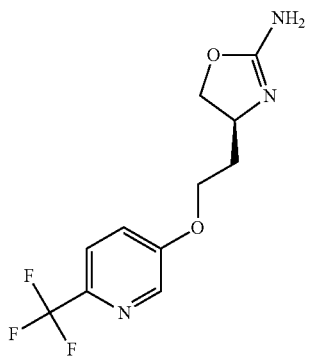 [SMILES: NC1=N[C@@H](CCOc2ccc(C(F)(F)F)nc2)CO1]

The title compound was obtained in analogy to example 3 starting from 3-hydroxy-6-trifluoromethyl-pyridine instead of 4-chlorophenol. White solid. MS (ISP): 276.2 ([M+H]$^+$).

EXAMPLE 136

3-[2-((S)-2-Amino-4,5-dihydro-oxazol-4-yl)-ethoxy]-benzoic acid benzyl ester

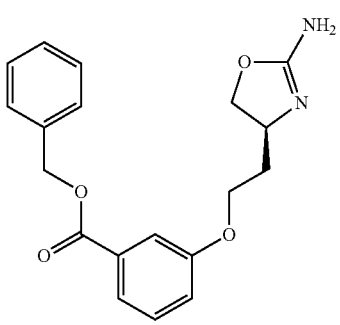 [SMILES: NC1=N[C@@H](CCOc2cccc(C(=O)OCc3ccccc3)c2)CO1]

The title compound was obtained in analogy to example 3 starting from benzyl 3-hydroxybenzoate instead of 4-chlorophenol. Colourless viscous oil. MS (ISP): 341.1 ([M+H]$^+$).

EXAMPLE 137

(S)-4-[2-(5-Fluoro-pyrimidin-2-yloxy)-ethyl]-4,5-dihydro-oxazol-2-ylamine

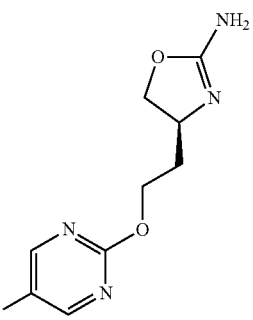

The title compound was obtained in analogy to example 131 starting from tert-butyl (S)-4-(2-hydroxyethyl)-2,2-dimethyl-oxazolidine-3-carboxylate and 2-chloro-5-fluoro-pyrimidine. White solid. MS (ISP): 227.2 ([M+H]⁺).

EXAMPLE 138

(S)-4-[2-(4-Methyl-pyrimidin-2-yloxy)-ethyl]-4,5-dihydro-oxazol-2-ylamine

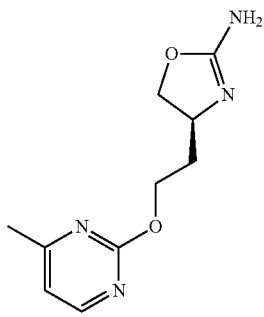 [SMILES: Cc1ccnc(OCC[C@H]2COC(N)=N2)n1]

The title compound was obtained in analogy to example 131 starting from tert-butyl (S)-4-(2-hydroxyethyl)-2,2-dimethyl-oxazolidine-3-carboxylate and 2-chloro-4-methyl-pyrimidine. Colourless oil. MS (ISP): 223.2 ([M+H]⁺).

EXAMPLE 139

(S)-4-[2-(4-Trifluoromethyl-pyrimidin-2-yloxy)-ethyl]-4,5-dihydro-oxazol-2-ylamine

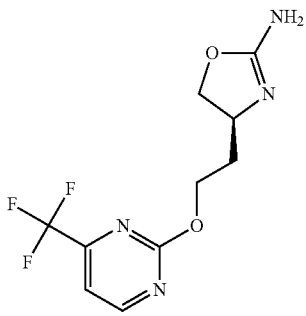 [SMILES: NC1=N[C@@H](CCOc2nccc(C(F)(F)F)n2)CO1]

The title compound was obtained in analogy to example 131 starting from tert-butyl (S)-4-(2-hydroxyethyl)-2,2-dimethyl-oxazolidine-3-carboxylate and 2-chloro-4-trifluoromethylpyrimidine. Colourless oil. MS (ISP): 277.1 ([M+H]⁺).

EXAMPLE 140

(S)-4-[(S)-2-(3-Benzyloxy-phenoxy)-butyl]-4,5-dihydro-oxazol-2-ylamine

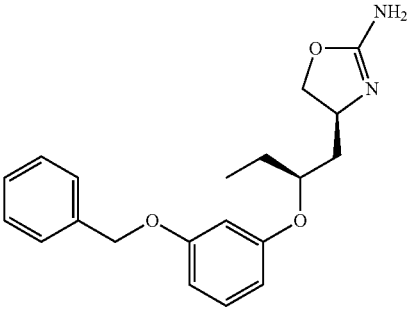 [SMILES: CC[C@@H](C[C@H]1COC(N)=N1)Oc1cccc(OCc2ccccc2)c1]

The title compound was obtained in analogy to example 94 starting from (S)-4-(R)-2-hydroxy-butyl)-2,2-dimethyl-oxazolidine-3-carboxylic acid tert-butyl ester and 3-benzyloxyphenol. Light yellow gum. MS (ISP): 341.1 ([M+H]⁺).

EXAMPLE 141

3-[(S)-1-((8)-2-Amino-4,5-dihydro-oxazol-4-ylmethyl)-propoxy]-phenol

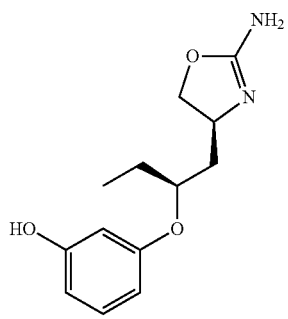 [SMILES: CC[C@@H](C[C@H]1COC(N)=N1)Oc1cccc(O)c1]

To a solution of (S)-4-[(S)-2-(3-benzyloxy-phenoxy)-butyl]-4,5-dihydro-oxazol-2-ylamine (60 mg) in methanol (3 ml) at room temperature was added 10% palladium on charcoal (19 mg). The mixture was stirred under an atmosphere of hydrogen (1 atm) at room temperature for 1 h. The catalyst was removed by filtration through decalite, washing with methanol and with dichloromethane, and the filtrate was concentrated in vacuo to yield 3-[(S)-1-(S)-2-amino-4,5-dihydro-oxazol-4-ylmethyl)-propoxy]-phenol as a white solid (44 mg, quant.); MS (ISP): 251.2 ([M+H]⁺).

EXAMPLE 142

(S)-4-{2-[1-(3,5-Difluoro-phenyl)-cyclopropyl]-ethyl}-4,5-dihydro-oxazol-2-ylamine

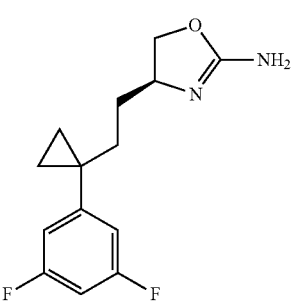 [SMILES: NC1=N[C@@H](CCC2(c3cc(F)cc(F)c3)CC2)CO1]

a) 1-(3,5-Difluoro-phenyl)-cyclopropanecarbonitrile

To a mixture of 3,5-difluoro-phenylacetonitrile (11.48 g), 1,2-dibromoethane (42.2 ml) and benzyltriethylammonium chloride (0.68 g) was added sodium hydroxide solution (50% in water, 30 ml) at room temperature. The mixture was vigorously stirred overnight. Water was added and the aqueous phase was extracted twice with diethyl ether. The combined organic layers were washed with water and brine, dried over MgSO$_4$ and concentrated. The residue was purified by column chromatography (SiO$_2$; heptane/EtOAc) to give 1-(3,5-difluoro-phenyl)cyclopropanecarbonitrile as a light pink solid (8.23 g). $^1$H-NMR (300 MHz, CDCl$_3$, δ): 1.40-1.44, (m, 2H), 1.78-1.82 (m, 2H), 6.70-6.85 (m, 3H).

b) 1-(3,5-Difluoro-phenyl)-cyclopropanecarbaldehyde

To a stirred, cooled (−78° C.) solution of 1-(3,5-difluoro-phenyl)cyclopropanecarbaldehyde (8.0 g) in toluene (300 ml) under an argon atmosphere was added slowly a solution of diisobutylaluminium hydride in toluene (44.6 ml; 1.2M in toluene). The mixture was stirred for 1 h, then the cooling bath was removed and the reaction mixture was quenched by adding an aqueous solution of Seignette salt. After stirring for 10 min ethyl acetate was added. The organic layer was separated, washed with brine, dried over MgSO$_4$ and concentrated. The residue was distilled in vacuo (Kugelrohr 160° C., 1.2 mbar) to give 143,5-difluoro-phenyl)-cyclopropanecarbaldehyde as light brown liquid (7.0 g). $^1$H-NMR (300 MHz, CDCl$_3$, δ): 1.40-1.44 (m, 2H), 1.56-1.62 (m, 2H), 6.72-6.85 (m, 3H), 9.14 (s, 1H).

c) [1-(3,5-Difluoro-phenyl)-cyclopropyl]-acetaldehyde

To a stirred, cooled (0° C.) solution of (methoxymethyl)triphenylphosphonium chloride (24.9 g) in tetrahydrofuran (190 ml) under an argon atmosphere was added slowly a solution of potassium tert.butoxide in tetrahydrofuran (30 ml) followed (after 30 min stirring) by a solution of 1-(3,5-difluoro-phenyl)-cyclopropanecarbaldehyde (6.3 g) in tetrahydrofuran (40 ml). Stirring was continued overnight, then the reaction mixture was quenched by adding an aqueous sodium chloride solution. The mixture was extracted with ethyl acetate twice and the combined organic layers were dried over MgSO$_4$ and concentrated. The crude enol ether was dissolved in acetone (20 ml) and stirred with 6 M aqueous hydrochloric acid (40 ml) for 6 hours at room temperature. Ethyl acetate was added, the organic layer was separated, washed with brine, dried over MgSO$_4$ and concentrated. The residue was purified by column chromatography (SiO$_2$; heptane/EtOAc=4:1) to give [1-(3,5-difluoro-phenyl)-cyclopropyl]-acetaldehyde as yellow liquid (2.55 g). $^1$H-NMR (300 MHz, CDCl$_3$, δ): 0.92-0.98 (m, 2H), 1.00-1.06 (m, 2H), 2.65 (d, J=2 Hz, 2H), 6.60-6.67 (m, 1H), 6.75-6.81 (m, 2H), 9.74 (t, J=2 Hz, 1H).

d) 2-[1-(3,5-difluoro-phenyl)-cyclopropyl]-ethanol

To a stirred, cooled (0° C.) solution of sodiumborohydride (1.0 g) in methanol (20 ml) under an argon atmosphere was added slowly a solution of [1-(3,5-difluoro-phenyl)cyclopropyl]-acetaldehyde in methanol (10 ml). Stirring was continued at room temperature overnight, then the reaction mixture was quenched by slow addition of water. Methanol was evaporated and the aqueous phase was extracted with ethyl acetate twice. The combined organic layers were dried over MgSO$_4$ and concentrated to give 2-[1-(3,5-difluoro-phenyl)-cyclopropyl]-ethanol as yellow liquid (2.37 g). $^1$H-NMR (300 MHz, CDCl$_3$, δ): 0.76-0.86 (m, 4H), 1.85 (t, J=7 Hz, 2H), 3.61-3.62 (m, 2H), 6.60-6.67 (m, 1H), 6.78-6.85 (m, 2H).

e) (S)-4-{2-[143,5-Difluoro-phenyl)-cyclopropyl]-ethyl}-4,5-dihydro-oxazol-2-ylamine The title compound was obtained in analogy to example 12 starting from 2-[1-(3,5-difluoro-phenyl)-cyclopropyl]-ethanol instead of 4,4,4-trifluoro-3-phenyl-butan-1-ol. White solid. MS (ISP): 267.2 ([M+H]$^+$).

EXAMPLE 143

(S)-4-{2-[1-(3-Chloro-5-fluoro-phenyl)-cyclopropyl]-ethyl}-4,5-dihydro-oxazol-2-ylamine

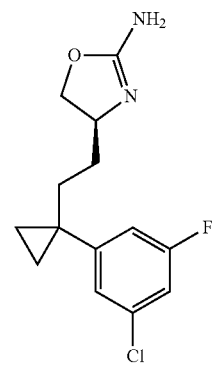 [SMILES: NC1=N[C@@H](CCC2(c3cc(F)cc(Cl)c3)CC2)CO1]

The title compound was obtained in analogy to example 91 starting from 3-chloro-5-fluoro-phenylacetonitrile instead of 3-chloro-4-fluoro-phenylacetonitrile. Colourless oil. MS (ISP): 283.1 ([M+H]$^+$).

EXAMPLE 144

(S)-4-{2-[1-(4-Bromo-phenyl)-cyclopropyl]-ethyl}-4,5-dihydro-oxazol-2-ylamine

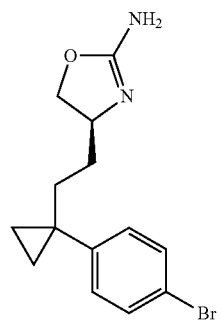 [SMILES: NC1=N[C@@H](CCC2(c3ccc(Br)cc3)CC2)CO1]

The title compound was obtained in analogy to example 91 starting from 4-bromophenylacetonitrile instead of 3-chloro-4-fluoro-phenylacetonitrile. White solid. MS (ISP): 309.1, 311.0 ([M+H]$^+$).

EXAMPLE 145

(S)-4-[2-(6-Chloro-pyridin-3-yloxy)-ethyl]-4,5-dihydro-oxazol-2-ylamine

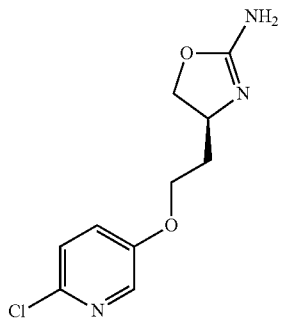 [SMILES: NC1=N[C@@H](CCOc2ccc(Cl)nc2)CO1]

The title compound was obtained in analogy to example 3 starting from 3-hydroxy-6-chloro-pyridine instead of 4-chlorophenol. White solid. MS (ISP): 244.2 ([{$^{37}$Cl}M+H]$^+$), 242.2 ([{$^{35}$Cl}M+H]$^+$).

EXAMPLE 146

(S)-4-[2-(6-Bromo-pyridin-3-yloxy)-ethyl]-4,5-dihydro-oxazol-2-ylamine

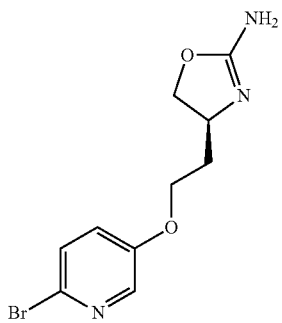

The title compound was obtained in analogy to example 3 starting from 3-hydroxy-6-bromo-pyridine instead of 4-chlorophenol. White solid. MS (ISP): 288.0 ([{$^{81}$Br}M+H]$^+$), 286.0 ([{$^{79}$Br}M+H]$^+$).

EXAMPLE 147

(S)-4-[2-(5-Bromo-pyridin-2-yloxy)-ethyl]-4,5-dihydro-oxazol-2-ylamine

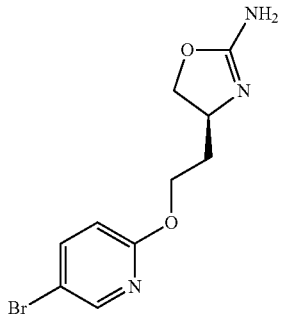

The title compound was obtained in analogy to example 131 starting from tert-butyl (S)-4-(2-hydroxyethyl)-2,2-dimethyl-oxazolidine-3-carboxylate and 5-bromo-2-fluoro-pyridine. White solid. MS (ISP): 287.9 ([{$^{81}$Br}M+H]$^+$), 286.0 ([{$^{79}$Br}M+H]$^+$).

EXAMPLE 148

(S)-4-[2-(1-Pyridin-3-yl-cyclopropyl)-ethyl]-4,5-dihydro-oxazol-2-ylamine

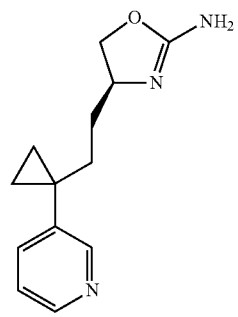 [SMILES: NC1=N[C@@H](CCC2(c3cccnc3)CC2)CO1]

The title compound was obtained in analogy to example 30 starting from 1-(6-chloropyrid-3-yl)-cyclopropanecarbaldehyde instead of 1-(4-chloro-phenyl)-cyclopropanecarbaldehyde (complete hydrogenolytic dechlorination occurred in step d). Light yellow oil. MS (ISP): 232.1 ([M+H]$^+$).

EXAMPLE 149

(S)-4-[2-(5-Chloro-pyridin-2-yloxy)-ethyl]-4,5-dihydro-oxazol-2-ylamine

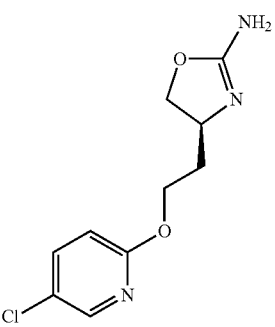 [SMILES: NC1=N[C@@H](CCOc2ccc(Cl)cn2)CO1]

The title compound was obtained in analogy to example 131 starting from tert-butyl (S)-4-(2-hydroxyethyl)-2,2-dimethyl-oxazolidine-3-carboxylate and 5-chloro-2-fluoro-pyridine. White solid. MS (ISP): 244.3 ([{$^{37}$Cl}M+H]$^+$), 242.2 ([{$^{35}$Cl}M+H]$^+$).

EXAMPLE 150

(S)-4-[2-(4-Fluoro-phenylsulfanyl)-ethyl]-4,5-dihydro-oxazol-2-ylamine

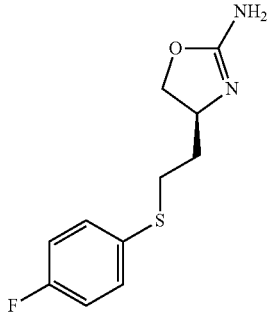 [SMILES: NC1=N[C@@H](CCSc2ccc(F)cc2)CO1]

a) (S)-4-[2-(4-Fluoro-phenylsulfanyl)-ethyl]-2,2-dimethyl-oxazolidine-3-carboxylic acid tert-butyl ester To a stirred solution of tert-butyl (S)-4-(2-hydroxyethyl)-2,2-dimethyl-oxazolidine-3-carboxylate (1.0 g) at 0° C. (ice cooling) in dichloromethane (25 ml) under an argon atmosphere were added N-ethyldiisopropylamine (3.5 ml) and methanesulfonyl chloride (0.56 g). The mixture was stirred at 0° C. for 2.5 hours Water was added and the mixture was extracted 3 times with dichloromethane. The combined organic layers were dried (MgSO4) and evaporated to yield crude (S)-4-(2-methanesulfonyloxy-ethyl)-2,2-dimethyl-oxazolidine-3-carboxylic acid tert-butyl ester. To a stirred solution of this compound (1.4 g) at room temperature in tetrahydrofuran (15 ml) under an argon atmosphere were added 4-fluorothiophenol (1.11 g) and triethylamine (0.88 g). The mixture was stirred at room temperature overnight. The solvent was evaporated and the residue was purified by column chromatography (SiO$_2$; heptane/EtOAc=4:1) to give (S)-4-[2-(4-fluoro-phenylsulfanyl)-ethyl]-2,2-dimethyl-oxazolidine-3-carboxylic acid tert-butyl ester (1.0 g) as a colourless oil which was used for the next step.

b) (S)-2-Amino-4-(4-fluoro-phenylsulfanyl)-butan-1-ol

To (S)-4-[2-(4-fluoro-phenylsulfanyl)-ethyl]-2,2-dimethyl-oxazolidine-3-carboxylic acid tert-butyl ester (0.5 g) was added under an argon atmosphere 5.5 M HCl solution in ethanol (2 ml). The mixture was stirred for 16 h. The mixture was concentrated. The residue was dissolved in dichloromethane and an excess of ammonia in methanol and some silica gel was added. The solvents were evaporated and the crude product was purified by column chromatography (column: Isolute® Flash-NH$_2$ from Separtis; eluent: dichloromethane/methanol=90:10) to give (S)-2-amino-4-(4-fluoro-phenylsulfanyl)-butan-1-ol (0.25 g) as a colourless liquid. MS (ISP): 216.3 ([M+H]$^+$).

c) (S)-4-[2-(4-Fluoro-phenylsulfanyl)-ethyl]-4,5-dihydro-oxazol-2-ylamine

In analogy to example 1d (S)-2-amino-4-(4-fluoro-phenylsulfanyl)-butan-1-ol was reacted with cyanogen bromide to give (S)-4-[2-(4-fluoro-phenylsulfanyl)-ethyl]-4,5-dihydro-oxazol-2-ylamine. Colourless oil. MS (ISP): 241.2 ([M+H]$^+$).

EXAMPLE 151

(S)-4-[2-(4-Fluoro-benzenesulfonyl)-ethyl]-4,5-dihydro-oxazol-2-ylamine

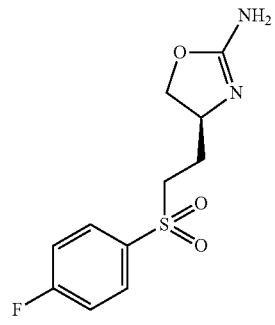 [SMILES: NC1=N[C@@H](CCS(=O)(=O)c2ccc(F)cc2)CO1]

a) (S)-4-[2-(4-Fluoro-benzenesulfonyl)-ethyl]-2,2-dimethyl-oxazolidine-3-carboxylic acid tert-butyl ester To a stirred solution of (S)-4-[2-(4-fluoro-phenylsulfanyl)-ethyl]-2,2-dimethyl-oxazolidine-3-carboxylic acid tert-butyl ester (0.25 g) at 0° C. in ethyl acetate (2 ml) was added a solution of m-chloroperbenzoic acid (0.24 g) in ethyl acetate (2.5 ml). The mixture was stirred at room temperature overnight. Then saturated sodium sulfite solution and saturated sodium bicarbonate solution were added and the mixture was stirred for 30 min. The mixture was extracted three times with ethyl acetate, the combined organic layers were dried with magnesium sulphate, filtered and evaporated. The residue was purified by column chromatography (SiO$_2$; heptane/EtOAc=4:1) to give (S)-4-[2-(4-fluoro-benzenesulfonyl)-ethyl]-2,2-dimethyl-oxazolidine-3-carboxylic acid tert-butyl ester (0.21 g) as a colorless oil which was used for the next step.

b) (S)-2-Amino-4-(4-fluoro-benzenesulfonyl)-butan-1-ol

To (S)-4-[2-(4-fluoro-phenylsulfonyl)-ethyl]-2,2-dimethyl-oxazolidine-3-carboxylic acid tert-butyl ester (0.21 g) was added under an argon atmosphere 5.5 M HCl solution in ethanol (2 ml). The mixture was stirred for 4 h. The mixture was concentrated. The residue was dissolved in dichloromethane and an excess of ammonia in methanol and some silica gel was added. The solvents were evaporated and the crude product was purified by column chromatography (column: Isolute® Flash-NH$_2$ from Separtis; eluent: dichloromethane/methanol=90:10) to give (S)-2-amino-4-(4-fluoro-phenylsulfonyl)-butan-1-ol (0.10 g) as a colourless oil. MS (ISP): 248.1 ([M+H]$^+$).

c) S-4-[2-4-Fluoro-phenylsulfonyl)-ethyl]-4,5-dihydro-oxazol-2-ylamine

In analogy to example 1d (S)-2-amino-4-(4-fluoro-phenylsulfonyl)-butan-1-ol was reacted with cyanogen bromide to give (S)-4-[2-(4-fluoro-phenylsulfonyl)-ethyl]-4,5-dihydro-oxazol-2-ylamine. Colourless oil. MS (ISP): 273.1 ([M+H]$^+$).

EXAMPLE 152

(S)-4-[(S)-2-(2,4,5-Trifluoro-phenoxy)-butyl]-4,5-dihydro-oxazol-2-ylamine

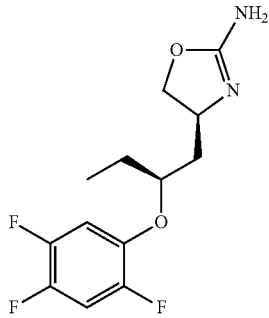 [SMILES: CC[C@@H](C[C@H]1COC(N)=N1)Oc1cc(F)c(F)cc1F]

The title compound was obtained in analogy to example 94 starting from (S)-4-(R)-2-hydroxy-butyl)-2,2-dimethyl-oxazolidine-3-carboxylic acid tert-butyl ester and 2,4,5-trifluorophenol. Colourless gum. MS (ISP): 289.3 ([M+H]$^+$).

EXAMPLE 153

(S)-4-[(S)-2-(Naphthalen-2-yloxy)-butyl]-4,5-dihydro-oxazol-2-ylamine

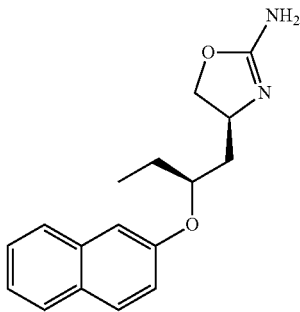 [SMILES: CC[C@@H](C[C@H]1COC(N)=N1)Oc1ccc2ccccc2c1]

The title compound was obtained in analogy to example 94 starting from (S)-4-(R)-2-hydroxy-butyl)-2,2-dimethyl-oxazolidine-3-carboxylic acid tert-butyl ester and 2-naphthol. White solid. MS (ISP): 285.4 ([M+H]$^+$).

EXAMPLE 154

(S)-4-[1-(4-Fluoro-phenyl)-1-methyl-ethoxymethyl]-4,5-dihydro-oxazol-2-ylamine

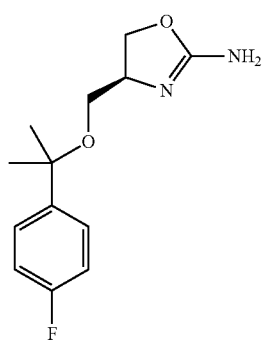 [SMILES: CC(C)(OC[C@H]1COC(N)=N1)c1ccc(F)cc1]

a) (1-(1-Allyloxy-1-methyl-ethyl)-4-fluoro-benzene

To a stirred solution of sodium hydride (1.47 g) in dry tetrahydrofuran (60 ml) was added dropwise under an argon atmosphere a solution of 2-(4-fluorophenyl)-2-propanol (4.35 g) in dry tetrahydrofuran (10 ml). The resulting yellow suspension was stirred at room temperature for 10 min. A solution of allyl bromide (3.1 ml) diluted in dry tetrahydrofuran (10 ml) was added slowly. The reaction mixture was stirred for 30 min and quenched by addition of water. The solution was extracted with ethyl acetate twice. The combined organic layers were dried (MgSO$_4$) and evaporated. The crude product was purified by column chromatography (SiO$_2$; gradient: heptane/EtOAc 100:0->90:10) to give 1-(1-allyloxy-1-methyl-ethyl)-4-fluoro-benzene (3.30 g, 60%) as a light yellow liquid. MS (EI): 179.0 ([M-CH$_3$]).

b) (S)-3-[1-(4-Fluoro-phenyl)-1-methyl-ethoxy]-propane-1,2-diol

AD-MIX-beta (3.25 g) was stirred in t-BuOH/H2O 1:1 (24 ml) for 15 min an cooled to 0° C. To this solution was added 1-(1-allyloxy-1-methyl-ethyl)-4-fluoro-benzene (0.50 g). The mixture was stirred for 16 h at 0° C. The reaction mixture was treated with sodium sulfite and stirred for 30 min. The solution was extracted with ethylacetate twice. The combined organic layers were dried (MgSO$_4$) and evaporated. The product was purified by column chromatography (SiO$_2$; heptane/EtOAc 2:1) to give (S)-3-[1-(4-fluoro-phenyl)-1-methyl-ethoxy]-propane-1,2-diol (0.47 g, 80%) as a light yellow liquid. MS (EI): 213.0 ([M-CH$_3$]), 137.0 (F—C$_6$H$_4$—C(CH$_3$)$_2^+$)

c) (R)-1-(tert-Butyl-dimethyl-silanyloxy)-3-[1-(4-fluoro-phenyl)-1-methyl-ethoxy]-propan-2-ol To a solution of (S)-3-[1-(4-fluoro-phenyl)-1-methyl-ethoxy]-propane-1,2-diol (0.46 g) in tetrahydrofuran (6 ml) were added imidazole (0.32 g) and 4-dimethylaminopyridine (catalytic amount). The mixture was cooled to 0° C. and a solution of tert-butyl(chloro)dimethylsilane (0.32 g) in tetrahydrofuran (2 ml) was added dropwise. After 2 hours at 0° C., the reaction mixture was allowed to stir at room temperature for 16 hours. Water was added and the mixture was extracted twice with diethylether. The combined organic layers were dried (MgSO$_4$) and evaporated. The crude product was purified by column chromatography (SiO$_2$; gradient: heptane/EtOAc 90:10->75:25) to give (R)-1-(tert-butyl-dimethyl-silanyloxy)-3-[1-(4-fluorophenyl)-1-methyl-ethoxy]-propan-2-ol (0.57 g, 83%) as a colorless liquid. $^1$H NMR (300 MHz, CDCl$_3$, δ): 0.00 (s, 6H), 0.82 (s, 9H), 1.48 (s, 6H), 2.49 (bs, 1H), 3.15 (d, J=4 Hz, 2H), 3.56 (t, J=4 Hz, 2H), 3.68 (m, 1H)

d) {(S)-2-Azido-3-[1-4-fluoro-phenyl)-1-methyl-ethoxy]-propoxy}-tert-butyl-dimethyl-silane To a stirred mixture of (R)-1-(tert-butyl-dimethyl-silanyloxy)-3-[1-(4-fluoro-phenyl)-1-methyl-ethoxy]-propan-2-ol (560 mg) and triethylamine (0.3 ml) in dichloromethane (5 ml) at 0° C. was added methane sulfonyl chloride (225 mg). The mixture was stirred for 30 min at 0° C. and 2 h at room temperature, then saturated ammoniumchloride solution and dichloromethane were added. The aqueous phase was extracted a second time with dichloromethane, and the combined organic layers were washed with brine and dried over MgSO$_4$. The solvent was evaporated and the product was dried under high vacuum. The mesylate (324 mg) was dissolved in 1 ml of DMF and sodium azide (100 mg) was added. The reaction mixture was stirred at 100° C. for 16 hours. The reaction was quenched with water and extracted twice with ethyl acetate. The combined organic layers were dried over MgSO$_4$ and evaporated. The crude product was purified by column chromatography (SiO$_2$; gradient: heptane/EtOAc 100:0->90:10) to give {(S)-2-azido-3-[1-(4-fluoro-phenyl)-1-methyl-ethoxy]-propoxy}-tert-butyldimethyl-silane (140 mg) as a light yellow liquid. $^1$H NMR (300 MHz, CDCl$_3$, δ):1.56 (s, 6H), 1.97 (bs, 1H), 3.33 (d, J=4.8 Hz, 2H), 3.59-3.66 (m, 2H), 3.72-3.74 (m, 1H), 7.03 (t, J=7.5 Hz), 7.36-7.41 (dd, J=7.5 Hz, J=4.2 Hz).

e) (R)-2-Amino-3-[1-(4-fluoro-phenyl)-1-methyl-ethoxy]-propan-1-ol

To a stirred solution of lithiumaluminiumhydride (41 mg) in dry tetrahydrofuran (2 ml) was added dropwise under an argon atmosphere a solution of {(S)-2-azido-3-[1-(4-fluorophenyl)-1-methyl-ethoxy]-propoxy}-tert-butyl-dimethyl-silane (200 mg) in dry tetrahydrofuran (0.5 ml). The reaction mixture was stirred at room temperature for 48 hours and quenched by addition of water (0.04 ml), NaOH 4 N (0.04 ml) and H$_2$O (0.12 ml). The suspension was stirred for 30 min and was filtered through Celite and MgSO$_4$. The filtrate was evaporated to give crude (R)-2-amino-3-[1-(4-fluoro-phenyl)-1-methyl-ethoxy]-propan-1-ol (128 mg) as a light yellow liquid. MS (ISP): 228.3 ([M+H]$^+$)

f) (S)-4-[1-(4-Fluoro-phenyl)-1-methyl-ethoxymethyl]-4,5-dihydro-oxazol-2-ylamine In analogy to example 1d, (R)-2-amino-3-[1-(4-fluorophenyl)-1-methyl-ethoxy]-propan-1-ol was reacted with cyanogen bromide to give (S)-4-[1-(4-fluoro-phenyl)-1-methylethoxymethyl]-4,5-dihydro-oxazol-2-ylamine. Colourless oil. MS (ISP): 253.3 ([M+H]$^+$).

EXAMPLE 155

(S)-4-[(S)-1-(4-Fluoro-phenyl)-ethoxymethyl]-4,5-dihydro-oxazol-2-ylamine

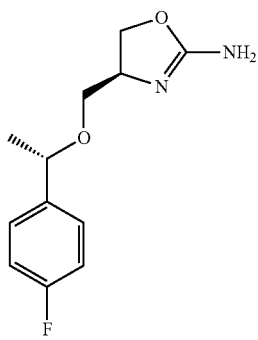 [SMILES: C[C@H](OC[C@H]1COC(N)=N1)c1ccc(F)cc1]

The title compound was obtained in analogy to example 154 starting from (S)-1-(4-fluorophenyl)-ethanol instead of 2-(4-fluorophenyl)-2-propanol. Light yellow liquid. MS (ISP): 239.0 ([M+H]$^+$).

EXAMPLE 156

(S)-4-((S)-1-Phenyl-propoxymethyl)-4,5-dihydro-oxazol-2-ylamine

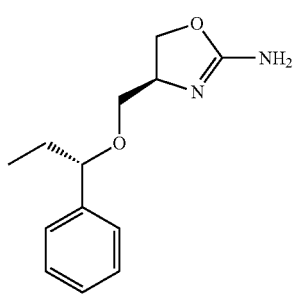 [SMILES: CC[C@H](OC[C@H]1COC(N)=N1)c1ccccc1]

The title compound was obtained in analogy to example 154 starting from (S)-1-phenyl-propan-1-ol instead of 2-(4-fluorophenyl)-2-propanol. Light yellow liquid. MS (ISP): 235.2 ([M+H]$^+$).

EXAMPLE 157

(S)-4-[(S)-2-(Quinolin-7-yloxy)-butyl]-4,5-dihydro-oxazol-2-ylamine

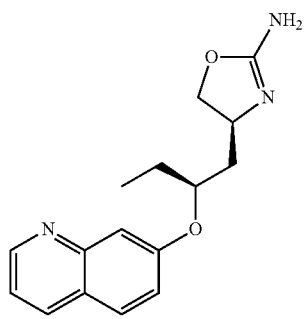 [SMILES: CC[C@@H](C[C@H]1COC(N)=N1)Oc1ccc2cccnc2c1]

The title compound was obtained in analogy to example 94 starting from (S)-4-((R)-2-hydroxy-butyl)-2,2-dimethyl-oxazolidine-3-carboxylic acid tert-butyl ester and 7-hydroxyquinoline. Colourless gum. MS (ISP): 286.3 ([M+H]$^+$).

EXAMPLE 158

(S)-4-[(S)-2-(2,4-Dichloro-phenoxy)-butyl]-4,5-dihydro-oxazol-2-ylamine

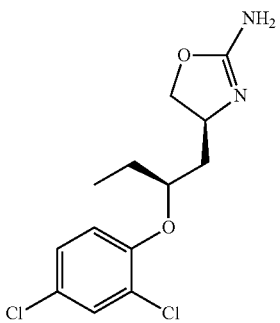 [SMILES: CC[C@@H](C[C@H]1COC(N)=N1)Oc1ccc(Cl)cc1Cl]

The title compound was obtained in analogy to example 94 starting from (S)-4-((R)-2-hydroxy-butyl)-2,2-dimethyl-oxazolidine-3-carboxylic acid tert-butyl ester and 2,4-dichloropyridine. Colourless gum. MS (ISP): 307.3 ([{$^{37}$Cl}M+H]$^+$), 305.2 ([{$^{37}$Cl$^{35}$Cl}M+H]$^+$), 303.3 ([{$^{35}$Cl}M+H]$^+$).

EXAMPLE 159

(S)-4-[(S)-2-(Quinolin-6-yloxy)-butyl]-4,5-dihydro-oxazol-2-ylamine

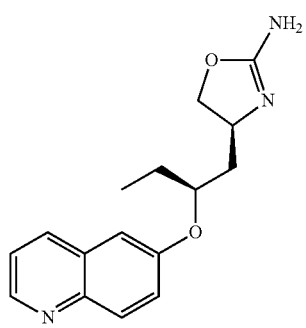 [SMILES: CC[C@@H](C[C@H]1COC(N)=N1)Oc1ccc2ncccc2c1]

The title compound was obtained in analogy to example 94 starting from (S)-4-((R)-2-hydroxy-butyl)-2,2-dimethyl-oxazolidine-3-carboxylic acid tert-butyl ester and 6-hydroxyquinoline. Colourless gum. MS (ISP): 286.3 ([M+H]+).

EXAMPLE 160

(S)-4-[(S)-2-(3,5-Bis-benzyloxy-phenoxy)-butyl]-4,5-dihydro-oxazol-2-ylamine

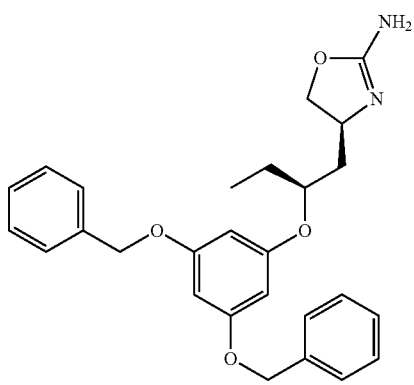 [SMILES: CC[C@@H](C[C@H]1COC(N)=N1)Oc1cc(OCc2ccccc2)cc(OCc2ccccc2)c1]

The title compound was obtained in analogy to example 94 starting from (S)-4-(R)-2-hydroxy-butyl)-2,2-dimethyl-oxazolidine-3-carboxylic acid tert-butyl ester and 3,5-bis-benzyloxy-phenol. Orange gum. MS (ISP): 447.3 ([M+H]+).

EXAMPLE 161

5-[(S)-1-(S)-2-Amino-4,5-dihydro-oxazol-4-ylmethyl)-propoxy]-benzene-1,3-diol

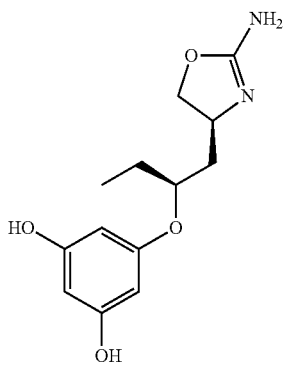 [SMILES: CC[C@@H](C[C@H]1COC(N)=N1)Oc1cc(O)cc(O)c1]

The title compound was obtained in analogy to example 141 starting from (S)-4-[(S)-2-(3,5-bis-benzyloxy-phenoxy)-butyl]-4,5-dihydro-oxazol-2-ylamine in place of (S)-4-[(S)-2-(3-benzyloxy-phenoxy)-butyl]-4,5-dihydro-oxazol-2-ylamine. Light brown solid. MS (ISP): 267.3 ([M+H]+).

EXAMPLE 162

(S)-4-[3,3-Difluoro-3-(4-fluoro-phenyl)-propyl]-4,5-dihydro-oxazol-2-ylamine

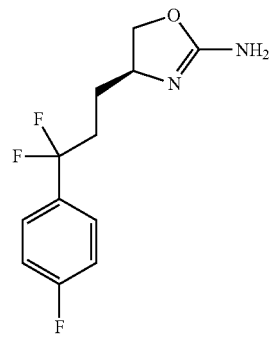 [SMILES: NC1=N[C@@H](CCC(F)(F)c2ccc(F)cc2)CO1]

a) 1-(4-Fluoro-phenyl)-pent-4-en-1-ol

Magnesium turnings (1.28 g) were placed in a 4-necked flask under an argon atmosphere. Iodine crystals were added and the mixture was heated until the iodine was consumed. The magnesium was covered with tetrahydrofuran (20 ml) and 4-bromo-1-butene (6.75 g) dissolved in dry tetrahydrofuran (20 ml) was added dropwise to the reaction mixture. The boiling solution was then heated for 1 hour at 70° C. then the temperature was reduced to 50° C. and 4-fluorobenzaldehyde (6.21 g) dissolved dry tetrahydrofuran (90 ml) was added dropwise to the reaction mixture. After stirring for 1 hour, the reaction mixture was cooled and was quenched with ammoniumchloride solution. The solution was extracted twice with diethylether and the combined organic layers were dried over MgSO4. The solvent was evaporated and the crude product was purified by column chromatography (SiO2; heptane/EtOAc 4:1->75:25) to give 1-(4-fluoro-phenyl)-pent-4-en-1-ol (4.94 g, 55%) as a light yellow liquid. MS (EI): 180.0 ([M+H]+)), 125.0 (F—C6H4CH+OH)

b) 1-(4-Fluoro-phenyl)-pent-4-en-1-one

To a stirred solution of 1-(4-fluoro-phenyl)-pent-4-en-1-ol (4.9 g) in dichloromethane (5 ml) was added pyridimium chlorochromate (7.033 g). The reaction mixture was stirred for 16 hours at room temperature. Silica gel was added and the solvent was evaporated. Column chromatography (SiO2; heptane/EtOAc 4:1) gave 1-(4-fluoro-phenyl)-pent-4-en-1-one (4.67 g, 96%) as a light yellow liquid.MS (EI): 178.0 ([M+H]+)), 123.0 (F—C6H4CO+)

c) 1-(1,1-Difluoro-pent-4-enyl)-4-fluoro-benzene

To a stirred solution of 1-(4-fluoro-phenyl)-pent-4-en-1-one (3.0 g) in toluene (3 ml) was added bis(2-methoxyethyl)aminosulphur trifluoride (4.90 ml) and the solution was heated at 70° C. for 16 hours. More bis(2-methoxyethyl)aminosulphur trifluoride (3.2 ml) was added and stirring was continued at 70° C. for 48 hours. The reaction mixture was cooled, diluted with dichloromethane and neutralized with 1 M sodium bicarbonate solution. The organic layer was dried over MgSO4 and evaporated and the crude product was purified by column chromatography (SiO2; heptane) to givel-(1,1-difluoro-pent-4-enyl)-4-fluoro-benzene (1.77 g, 53%) as a light yellow liquid. MS (EI): 200 ([M+H]+)), 145.0 (F—C6H4F2+)

d) (S)-4-[3,3-Difluoro-3-(4-fluoro-phenyl)-propyl]-4,5-dihydro-oxazol-2-ylamine

The title compound was obtained in analogy to the sequence of example 154 starting from of 1-(1,1-difluoro-pent-4-enyl)-4-fluoro-benzene instead of (1-(1-allyloxy-1-methyl-ethyl)-4-fluoro-benzene in step b). Solid white. MS (ISP): 259.1 ([M+H]$^+$).

EXAMPLE 163

(S)-4-[2-(5-Fluoro-pyridin-2-yloxy)-ethyl]-4,5-dihydro-oxazol-2-ylamine

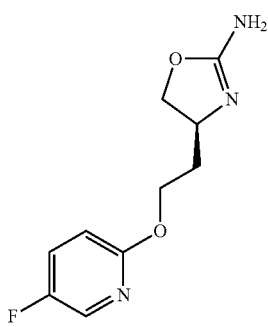 [SMILES: NC1=N[C@@H](CCOc2ccc(F)cn2)CO1]

The title compound was obtained in analogy to example 131 starting from tert-butyl (S)-4-(2-hydroxyethyl)-2,2-dimethyl-oxazolidine-3-carboxylate and 2,5-difluoro-pyridine. White solid. MS (ISP): 226.2 ([M+H]$^+$).

EXAMPLE 164

(S)-4-[(S)-3-(4-Fluoro-phenyl)-pentyl]-4,5-dihydro-oxazol-2-ylamine

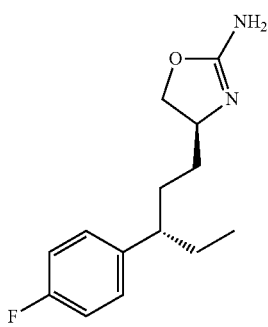 [SMILES: CC[C@@H](CC[C@H]1COC(N)=N1)c1ccc(F)cc1]

The title compound was obtained in analogy to example 12 starting from (S)-3-(4-fluorophenyl)-pentan-1-ol instead of 4,4,4-trifluoro-3-phenyl-butan-1-ol. Light yellow oil. MS (ISP): 251.4 ([M+H]$^+$).

EXAMPLE 165

(S)-4-[(R)-3-(4-Fluoro-phenyl)-pentyl]-4,5-dihydro-oxazol-2-ylamine

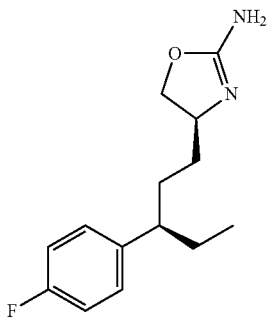 [SMILES: CC[C@H](CC[C@H]1COC(N)=N1)c1ccc(F)cc1]

The title compound was obtained in analogy to example 12 starting from (R)-3-(4-fluorophenyl)-pentan-1-ol instead of 4,4,4-trifluoro-3-phenyl-butan-1-ol. Light yellow oil. MS (ISP): 251.4 ([M+H]$^+$).

EXAMPLE 166

(S)-4-[(S)-2-(5-Fluoro-pyridin-2-yloxy)-butyl]-4,5-dihydro-oxazol-2-ylamine

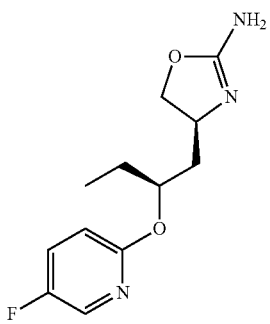 [SMILES: CC[C@@H](C[C@H]1COC(N)=N1)Oc1ccc(F)cn1]

The title compound was obtained in analogy to example 131 starting from (S)-4-(S)-2-hydroxy-butyl)-2,2-dimethyl-oxazolidine-3-carboxylic acid tert-butyl ester and 2,5-difluoro-pyridine. Colourless viscous oil. MS (ISP): 254.2 ([M+H]$^+$).

EXAMPLE 167

(S)-4-[(S)-2-(5-Chloro-pyridin-2-yloxy)-butyl]-4,5-dihydro-oxazol-2-ylamine

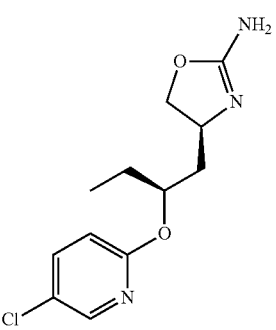 [SMILES: CC[C@@H](C[C@H]1COC(N)=N1)Oc1ccc(Cl)cn1]

The title compound was obtained in analogy to example 131 starting from (S)-4-(S)-2-hydroxy-butyl)-2,2-dimethyl-oxazolidine-3-carboxylic acid tert-butyl ester and 5-chloro-2-fluoro-pyridine. Light yellow viscous oil. MS (ISP): 272.1 ([{<sup>37</sup>Cl}M+H]<sup>+</sup>), 270.2 ([{<sup>35</sup>Cl}M+H]<sup>+</sup>).

EXAMPLE 168

(S)-4-[(R)-1-(4-Fluoro-phenyl)-ethoxymethyl]-4,5-dihydro-oxazol-2-ylamine

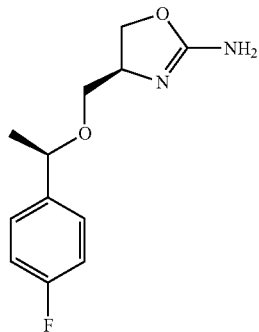 [SMILES: C[C@@H](OC[C@H]1COC(N)=N1)c1ccc(F)cc1]

The title compound was obtained in analogy to example 154 starting from (R)-1-(4-fluorophenyl)-ethanol instead of 2-(4-fluorophenyl)-2-propanol. Colourless oil. MS (ISP): 239.1 ([M+H]$^+$).

EXAMPLE 169

(S)-4-((R)-1-Phenyl-propoxymethyl)-4,5-dihydro-oxazol-2-ylamine

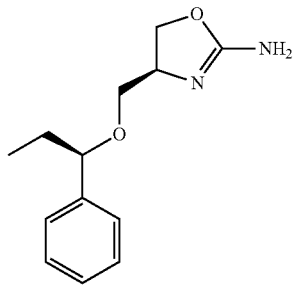 [SMILES: CC[C@@H](OC[C@H]1COC(N)=N1)c1ccccc1]

The title compound was obtained in analogy to example 154 starting from (R)-1-phenyl-propan-1-ol instead of 2-(4-fluorophenyl)-2-propanol. Colourless oil. MS (ISP): 235.2 ([M+H]$^+$).

EXAMPLE 170

(S)-4-[(S)-1-(3-Chloro-5-fluoro-phenyl)-ethoxymethyl]-4,5-dihydro-oxazol-2-ylamine

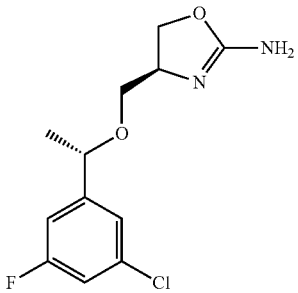 [SMILES: C[C@H](OC[C@H]1COC(N)=N1)c1cc(F)cc(Cl)c1]

a) (S)-1-(3-Chloro-5-fluoro-phenol)-ethanol

To a stirred solution of (R)-MeCBS oxazaborolidine (2.9 ml, 1M solution in toluene) in dry tetrahydrofuran (5 ml) was added dropwise borane-THF complex (17.4 ml, 1M solution in tetrahydrofuran) under an argon atmosphere. The solution was cooled to 0° C. and 3'-chloro-5'-fluoroacetophenone (5.0 g) dissolved in dry tetrahydrofuran (5 ml) was added dropwise to the reaction mixture in 40 min. The reaction mixture was stirred for 1 h at 0° C. and was slowly quenched with methanol (5 ml) followed by addition of HCl 4M in ethanol (1 ml). After stirring the mixture for 5 min at 0° C., the cooling bath was removed and the white suspension was stirred at room temperature for 30 min. The suspension was filtered over celite and the filtrate was evaporated over silica gel for purification. Column chromatography (SiO$_2$; heptane/EtOAc) afforded (S)-1-(3-chloro-5-fluoro-phenyl)-ethanol (4.50 g, 89%) as a colourless liquid. $^1$H NMR (300 MHz, CDCl$_3$, δ): 1.48 (d, J=6.3 Hz, 3H), 1.92 (bs, 1H), 4.87 (q, J=6.6 Hz), 6.98 (m, 2H), 7.16 (s, 1H).

b) (S)-4-[(S)-1-(3-Chloro-5-fluoro-phenyl)-ethoxymethyl]-4,5-dihydro-oxazol-2-ylamine The title compound was obtained in analogy to the sequence of example 154 starting from of l(S)-1-(3-chloro-5-fluoro-phenyl)-ethanol instead of 2-(4-fluorophenyl)-2-propanol. Solid white. MS (ISP): 273.2 ([M+H]$^+$).

EXAMPLE 171

(S)-4-(2-Benzyloxy-ethyl)-4,5-dihydro-oxazol-2-ylamine

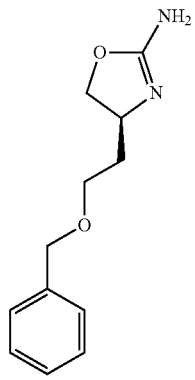 [SMILES: NC1=N[C@@H](CCOCc2ccccc2)CO1]

a) (S)-4-(2-Benzyloxy-ethyl)-2,2-dimethyl-oxazolidine-3-carboxylic acid tert-butyl ester

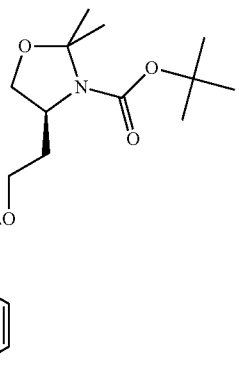

To a solution of (S)-4-(2-hydroxy-ethyl)-2,2-dimethyl-oxazolidine-3-carboxylic acid tert-butyl ester (200 mg) in THF (5 ml) at room temperature were added sequentially tetrabutylammonium iodide (15 mg) and sodium hydride (35 mg, 60% dispersion in mineral oil). After stirring the mixture for 5 min at room temperature, benzyl bromide (0.10 ml) was added dropwise and stirring was continued for a further 16 h. The mixture was quenched by addition of saturated aq. ammonium chloride solution (3 ml), diluted with water, and extracted twice with diethyl ether. The combined organic phases were dried over sodium sulphate, filtered, and the filtrate was concentrated in vacuo. The residue was purified by column chromatography (SiO$_2$; heptane/EtOAc) to yield (S)-4-(2-benzyloxy-ethyl)-2,2-dimethyl-oxazolidine-3-carboxylic acid tert-butyl ester as a colourless oil (199 mg, 73%); MS (ISP): 336.3 ([M+H]$^+$).

b) (S)-4-(2-Benzyloxy-ethyl)-4,5-dihydro-oxazol-2-ylamine

The title compound was obtained in analogy to example 3b-c starting from (S)-4-(2-benzyloxy-ethyl)-2,2-dimethyl-oxazolidine-3-carboxylic acid tert-butyl ester. Colourless viscous oil. MS (ISP): 221.3 ([M+H]$^+$).

EXAMPLE 172

(S)-4-(4-Phenyl-butyl)-4,5-dihydro-oxazol-2-ylamine

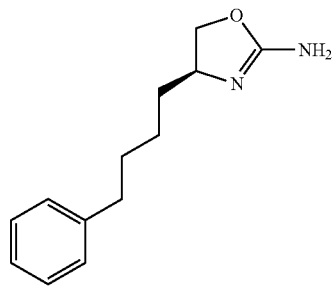 [SMILES: NC1=N[C@@H](CCCCc2ccccc2)CO1]

The title compound was obtained in analogy to example 12 starting from 4-phenyl-butan-1-ol instead of 4,4,4-trifluoro-3-phenyl-butan-1-ol. Colourless oil. MS (ISP): 219.3 ([M+H]$^+$).

EXAMPLE 173

(S)-4-[(S)-3-(4-Chloro-phenyl)-butyl]-4,5-dihydro-oxazol-2-ylamine

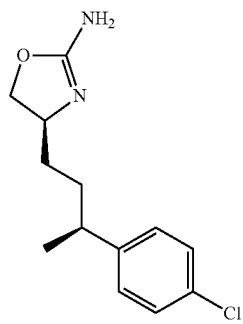 [SMILES: C[C@@H](CC[C@H]1COC(N)=N1)c1ccc(Cl)cc1]

The title compound was obtained in analogy to example 12 starting from (R)-3-(4-chlorophenyl)-butan-1-ol (synthesized according to a procedure described in J. Org. Chem. 2005, 70, 4133) instead of 4,4,4-trifluoro-3-phenyl-butan-1-ol. Light yellow oil. MS (ISP): 253.2 ([M+H]$^+$).

EXAMPLE 174

(S)-4-[(R)-2-(4-Chloro-phenoxy)-propyl]-4,5-dihydro-oxazol-2-ylamine

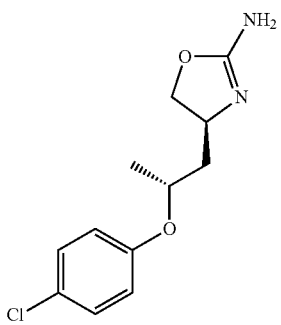

The title compound was obtained in analogy to example 45 starting from (S)-4-(S)-2-hydroxy-propyl)-2,2-dimethyl-oxazolidine-3-carboxylic acid tert-butyl ester and 4-chloro-phenol. Colourless viscous oil. MS (ISP): 257.2 ([{$^{37}$Cl}M+H]$^+$), 255.2 ([{$^{35}$Cl}M+H]$^+$).

EXAMPLE 175

(S)-4-[(S)-2-(4-Nitro-phenoxy)-butyl]-4,5-dihydro-oxazol-2-ylamine

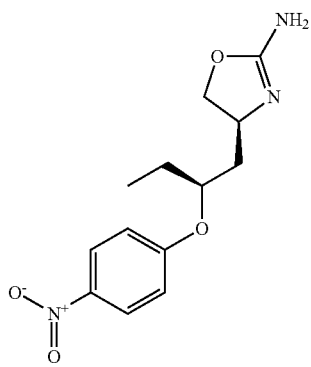 [SMILES: CC[C@@H](C[C@H]1COC(N)=N1)Oc1ccc([N+](=O)[O-])cc1]

The title compound was obtained in analogy to example 94 starting from (S)-4-(R)-2-hydroxy-butyl)-2,2-dimethyl-oxazolidine-3-carboxylic acid tert-butyl ester and 4-nitro-phenol. Light yellow oil which crystallised on standing overnight in dichloromethane/heptane (1:1). MS (ISP): 280.3 ([M+H]$^+$).

EXAMPLE 176

(S)-4-[(S)-2-(4-Methanesulfonyl-phenoxy)-butyl]-4,5-dihydro-oxazol-2-ylamine

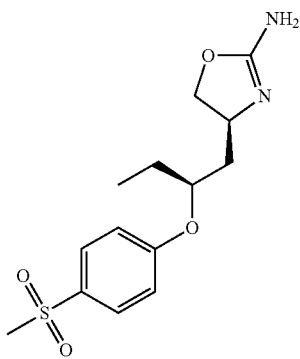 [SMILES: CC[C@@H](C[C@H]1COC(N)=N1)Oc1ccc(S(C)(=O)=O)cc1]

The title compound was obtained in analogy to example 94 starting from (S)-4-(R)-2-hydroxy-butyl)-2,2-dimethyl-oxazolidine-3-carboxylic acid tert-butyl ester and 4-methanesulfonyl-phenol. Colourless gum. MS (ISP): 313.1 ([M+H]$^+$).

The invention claimed is:
1. A compound selected from the group consisting of
(S)-4-[2-(4-benzyl-phenoxy)-ethyl]-4,5-dihydro-oxazol-2-ylamine;
(S)-4-[2-(4'-fluoro-biphenyl-4-yloxy)-ethyl]-4,5-dihydro-oxazol-2-ylamine;
(S)-4-[2-(4-chloro-3-fluoro-phenoxy)-ethyl]-4,5-dihydro-oxazol-2-ylamine;
(S)-4-[2-(4-bromo-phenoxy)-ethyl]-4,5-dihydro-oxazol-2-ylamine;
(S)-4-[2-(3,4-dichloro-phenoxy)-ethyl]-4,5-dihydro-oxazol-2-ylamine;
(S)-4-[2-(4-chloro-2-fluoro-phenoxy)-ethyl]-4,5-dihydro-oxazol-2-ylamine;
(S)-4-[2-(4-methoxy-phenoxy)-ethyl]-4,5-dihydro-oxazol-2-ylamine;
(S)-4-[2-(4-trifluoromethyl-phenoxy)-ethyl]-4,5-dihydro-oxazol-2-ylamine;
3-[2-((S)-2-amino-4,5-dihydro-oxazol-4-yl)-ethoxy]-benzonitrile;
3-[4-(S)-2-amino-4,5-dihydro-oxazol-4-yl)-ethoxy]-benzoic acid methyl ester;
(S)-4-[2-(3,5-difluoro-phenoxy)-ethyl]-4,5-dihydro-oxazol-2-ylamine;
3-[2-((S)-2-amino-4,5-dihydro-oxazol-4-yl)-ethoxy]-benzoic acid benzyl ester;
(S)-4-[(S)-2-(4-chloro-phenoxy)-propyl]-4,5-dihydro-oxazol-2-ylamine;
(S)-4-[(S)-2-(4-fluoro-phenoxy)-propyl]-4,5-dihydro-oxazol-2-ylamine;
(S)-4-[(S)-2-(3-chloro-phenoxy)-propyl]-4,5-dihydro-oxazol-2-ylamine;
(S)-4-[(S)-2-(3,4-difluoro-phenoxy)-propyl]-4,5-dihydro-oxazol-2-ylamine;
(S)-4-[(S)-2-(4-chloro-3-fluoro-phenoxy)-propyl]-4,5-dihydro-oxazol-2-ylamine;
(S)-4-[(S)-2-(4-bromo-phenoxy)-propyl]-4,5-dihydro-oxazol-2-ylamine;
(S)-4-[(S)-2-(3-chloro-4-fluoro-phenoxy)-propyl]-4,5-dihydro-oxazol-2-ylamine;
(S)-4-[(S)-2-(4-chloro-2-fluoro-phenoxy)-propyl]-4,5-dihydro-oxazol-2-ylamine;
(S)-4-[(S)-2-(2,4-difluoro-phenoxy)-propyl]-4,5-dihydro-oxazol-2-ylamine;
(S)-4-[(S)-2-(3,4-dichloro-phenoxy)-propyl]-4,5-dihydro-oxazol-2-ylamine;
3-[(S)-2-(S)-2-amino-4,5-dihydro-oxazol-4-yl)-1-methyl-ethoxy]-benzonitrile;
(S)-4-[(S)-2-(4-phenoxy-phenoxy)-propyl]-4,5-dihydro-oxazol-2-ylamine;
(S)-4-(S)-2-phenoxy-propyl)-4,5-dihydro-oxazol-2-ylamine;
(S)-4-[(R)-2-(3-chloro-phenoxy)-propyl]-4,5-dihydro-oxazol-2-ylamine;
(S)-4-[(R)-2-(3-chloro-4-fluoro-phenoxy)-propyl]-4,5-dihydro-oxazol-2-ylamine;
(S)-4-[(R)-2-(3,4-dichloro-phenoxy)-propyl]-4,5-dihydro-oxazol-2-ylamine;
(S)-4-[(S)-2-(4-chloro-phenoxy)-butyl]-4,5-dihydro-oxazol-2-ylamine;
(S)-4-(S)-2-phenoxy-butyl)-4,5-dihydro-oxazol-2-ylamine;
(S)-4-[(S)-2-(4-bromo-phenoxy)-butyl]-4,5-dihydro-oxazol-2-ylamine;
(S)-4-[(S)-2-(3-chloro-phenoxy)-butyl]-4,5-dihydro-oxazol-2-ylamine;
(S)-4-[(S)-2-(4-chloro-3-fluoro-phenoxy)-butyl]-4,5-dihydro-oxazol-2-ylamine;
(S)-4-[(S)-2-(2,4-difluoro-phenoxy)-butyl]-4,5-dihydro-oxazol-2-ylamine;
(S)-4-[(S)-2-(4-fluoro-phenoxy)-butyl]-4,5-dihydro-oxazol-2-ylamine;
(S)-4-[(S)-2-(3,4-difluoro-phenoxy)-butyl]-4,5-dihydro-oxazol-2-ylamine;
(S)-4-[(S)-2-(3-chloro-4-fluoro-phenoxy)-butyl]-4,5-dihydro-oxazol-2-ylamine;
(S)-4-[(S)-2-(4-trifluoromethyl-phenoxy)-butyl]-4,5-dihydro-oxazol-2-ylamine;
(S)-4-[(S)-2-(3,4-dichloro-phenoxy)-butyl]-4,5-dihydro-oxazol-2-ylamine;
(S)-4-[(S)-2-(4-chloro-2-fluoro-phenoxy)-butyl]-4,5-dihydro-oxazol-2-ylamine;
(S)-4-[(S)-2-(3-benzyloxy-phenoxy)-butyl]-4,5-dihydro-oxazol-2-ylamine;
3-[(S)-1-((S)-2-amino-4,5-dihydro-oxazol-4-ylmethyl)-propoxy]-phenol;
(S)-4-[(S)-2-(2,4,5-trifluoro-phenoxy)-butyl]-4,5-dihydro-oxazol-2-ylamine;
(S)-4-[(S)-2-(naphthalen-2-yloxy)-butyl]-4,5-dihydro-oxazol-2-ylamine;
(S)-4-[(S)-2-(2,4-dichloro-phenoxy)-butyl]-4,5-dihydro-oxazol-2-ylamine;
(S)-4-[(S)-3-(4-fluoro-phenyl)-butyl]-4,5-dihydro-oxazol-2-ylamine;
(S)-4-[(R)-3-(4-fluoro-phenyl)-butyl]-4,5-dihydro-oxazol-2-ylamine;
(4 S)-4-[3-(3,5-difluoro-phenyl)-pentyl]-4,5-dihydro-oxazol-2-ylamine;
(S)-4-[(S)-1-(4-fluoro-phenyl)-ethoxymethyl]-4,5-dihydro-oxazol-2-ylamine;
(S)-4-((S)-1-phenyl-propoxymethyl)-4,5-dihydro-oxazol-2-ylamine;

(S)-4-{2-[1-(4-fluoro-phenyl)-cyclopropyl]-ethyl}-4,5-dihydro-oxazol-2-ylamine;
(S)-4-{2-[1-(2,4-difluoro-phenyl)-cyclopropyl]-ethyl}-4,5-dihydro-oxazol-2-ylamine;
(S)-4-{2-[1-(3-chloro-4-fluoro-phenyl)-cyclopropyl]-ethyl}-4,5-dihydro-oxazol-2-ylamine;
(S)-4-{2-[1-(3,4-difluoro-phenyl)-cyclopropyl]-ethyl}-4,5-dihydro-oxazol-2-ylamine;
(S)-4-{2-[1-(4-chloro-phenyl)-cyclobutyl]-ethyl}-4,5-dihydro-oxazol-2-ylamine;
(S)-4-{2-[1-(3,5-difluoro-phenyl)-cyclopropyl]-ethyl}-4,5-dihydro-oxazol-2-ylamine;
(S)-4-{2-[1-(3-chloro-5-fluoro-phenyl)-cyclopropyl]-ethyl}-4,5-dihydro-oxazol-2-ylamine;
(S)-4-{2-[1-(4-bromo-phenyl)-cyclopropyl]-ethyl}-4,5-dihydro-oxazol-2-ylamine;
(S)-4-{2-[(3-chloro-phenyl)-dimethyl-silanyl]-ethyl}-4,5-dihydro-oxazol-2-ylamine; and
(S)-4-{2-[(4-chloro-phenyl)-dimethyl-silanyl]-ethyl}-4,5-dihydro-oxazol-2-ylamine.

2. The compound of claim 1, selected from the group consisting of
(S)-4-[2-(4-benzyl-phenoxy)-ethyl]-4,5-dihydro-oxazol-2-ylamine;
(S)-4-[2-(4'-fluoro-biphenyl-4-yloxy)-ethyl]-4,5-dihydro-oxazol-2-ylamine;
(S)-4-[2-(4-chloro-3-fluoro-phenoxy)-ethyl]-4,5-dihydro-oxazol-2-ylamine;
(S)-4-[2-(4-bromo-phenoxy)-ethyl]-4,5-dihydro-oxazol-2-ylamine;
(S)-4-[2-(3,4-dichloro-phenoxy)-ethyl]-4,5-dihydro-oxazol-2-ylamine; and
(S)-4-[2-(4-chloro-2-fluoro-phenoxy)-ethyl]-4,5-dihydro-oxazol-2-ylamine.

3. The compound of claim 1, selected from the group consisting of
(S)-4-[2-(4-methoxy-phenoxy)-ethyl]-4,5-dihydro-oxazol-2-ylamine;
(S)-4-[2-(4-trifluoromethyl-phenoxy)-ethyl]-4,5-dihydro-oxazol-2-ylamine;
3-[2-((S)-2-amino-4,5-dihydro-oxazol-4-yl)-ethoxy]-benzonitrile;
3-[2-((S)-2-amino-4,5-dihydro-oxazol-4-yl)-ethoxy]-benzoic acid methyl ester;
(S)-4-[2-(3,5-difluoro-phenoxy)-ethyl]-4,5-dihydro-oxazol-2-ylamine; and
3-[2-((S)-2-amino-4,5-dihydro-oxazol-4-yl)-ethoxy]-benzoic acid benzyl ester.

4. The compound of claim 1, selected from the group consisting of
(S)-4-[(S)-2-(4-chloro-phenoxy)-propyl]-4,5-dihydro-oxazol-2-ylamine;
(S)-4-[(S)-2-(4-fluoro-phenoxy)-propyl]-4,5-dihydro-oxazol-2-ylamine;
(S)-4-[(S)-2-(3-chloro-phenoxy)-propyl]-4,5-dihydro-oxazol-2-ylamine;
(S)-4-[(S)-2-(3,4-difluoro-phenoxy)-propyl]-4,5-dihydro-oxazol-2-ylamine;
(S)-4-[(S)-2-(4-chloro-3-fluoro-phenoxy)-propyl]-4,5-dihydro-oxazol-2-ylamine;
(S)-4-[(S)-2-(4-bromo-phenoxy)-propyl]-4,5-dihydro-oxazol-2-ylamine;
(S)-4-[(S)-2-(3-chloro-4-fluoro-phenoxy)-propyl]-4,5-dihydro-oxazol-2-ylamine; and
(S)-4-[(S)-2-(4-chloro-2-fluoro-phenoxy)-propyl]-4,5-dihydro-oxazol-2-ylamine.

5. The compound of claim 1, selected from the group consisting of
(S)-4-[(S)-2-(2,4-difluoro-phenoxy)-propyl]-4,5-dihydro-oxazol-2-ylamine;
(S)-4-[(S)-2-(3,4-dichloro-phenoxy)-propyl]-4,5-dihydro-oxazol-2-ylamine;
3-[(S)-2-((S)-2-amino-4,5-dihydro-oxazol-4-yl)-1-methyl-ethoxy]-benzonitrile;
(S)-4-[(S)-2-(4-phenoxy-phenoxy)-propyl]-4,5-dihydro-oxazol-2-ylamine;
(S)-4-(S)-2-phenoxy-propyl)-4,5-dihydro-oxazol-2-ylamine;
(S)-4-[(R)-2-(3-chloro-phenoxy)-propyl]-4,5-dihydro-oxazol-2-ylamine;
(S)-4-[(R)-2-(3-chloro-4-fluoro-phenoxy)-propyl]-4,5-dihydro-oxazol-2-ylamine; and
(S)-4-[(R)-2-(3,4-dichloro-phenoxy)-propyl]-4,5-dihydro-oxazol-2-ylamine.

6. The compound of claim 1, selected from the group consisting of
(S)-4-[(S)-2-(4-chloro-phenoxy)-butyl]-4,5-dihydro-oxazol-2-ylamine;
(S)-4-(S)-2-phenoxy-butyl)-4,5-dihydro-oxazol-2-ylamine;
(S)-4-[(S)-2-(4-bromo-phenoxy)-butyl]-4,5-dihydro-oxazol-2-ylamine;
(S)-4-[(S)-2-(3-chloro-phenoxy)-butyl]-4,5-dihydro-oxazol-2-ylamine;
(S)-4-[(S)-2-(4-chloro-3-fluoro-phenoxy)-butyl]-4,5-dihydro-oxazol-2-ylamine;
(S)-4-[(S)-2-(2,4-difluoro-phenoxy)-butyl]-4,5-dihydro-oxazol-2-ylamine;
(S)-4-[(S)-2-(4-fluoro-phenoxy)-butyl]-4,5-dihydro-oxazol-2-ylamine;
(S)-4-[(S)-2-(3,4-difluoro-phenoxy)-butyl]-4,5-dihydro-oxazol-2-ylamine; and
(S)-4-[(S)-2-(3-chloro-4-fluoro-phenoxy)-butyl]-4,5-dihydro-oxazol-2-ylamine.

7. The compound of claim 1, selected from the group consisting of
(S)-4-[(S)-2-(4-trifluoromethyl-phenoxy)-butyl]-4,5-dihydro-oxazol-2-ylamine;
(S)-4-[(S)-2-(3,4-dichloro-phenoxy)-butyl]-4,5-dihydro-oxazol-2-ylamine;
(S)-4-[(S)-2-(4-chloro-2-fluoro-phenoxy)-butyl]-4,5-dihydro-oxazol-2-ylamine;
(S)-4-[(S)-2-(3-benzyloxy-phenoxy)-butyl]-4,5-dihydro-oxazol-2-ylamine;
3-[(S)-1-(S)-2-amino-4,5-dihydro-oxazol-4-ylmethyl)-propoxy]-phenol;
(S)-4-[(S)-2-(2,4,5-trifluoro-phenoxy)-butyl]-4,5-dihydro-oxazol-2-ylamine;
(S)-4-[(S)-2-(naphthalen-2-yloxy)-butyl]-4,5-dihydro-oxazol-2-ylamine; and
(S)-4-[(S)-2-(2,4-dichloro-phenoxy)-butyl]-4,5-dihydro-oxazol-2-ylamine.

8. The compound of claim 1, selected from the group consisting of
(S)-4-[(S)-3-(4-fluoro-phenyl)-butyl]-4,5-dihydro-oxazol-2-ylamine;
(S)-4-[(R)-3-(4-fluoro-phenyl)-butyl]-4,5-dihydro-oxazol-2-ylamine; and
(4S)-4-[3-(3,5-difluoro-phenyl)-pentyl]-4,5-dihydro-oxazol-2-ylamine.

9. The compound of claim 1, selected from the group consisting of
- (S)-4-[(S)-1-(4-fluoro-phenyl)-ethoxymethyl]-4,5-dihydro-oxazol-2-ylamine; and
- (S)-4-((S)-1-phenyl-propoxymethyl)-4,5-dihydro-oxazol-2-ylamine.

10. The compound of claim 1, selected from the group consisting of
- (S)-4-{2-[1-(4-fluoro-phenyl)-cyclopropyl]-ethyl}-4,5-dihydro-oxazol-2-ylamine;
- (S)-4-{2-[1-(2,4-difluoro-phenyl)-cyclopropyl]-ethyl}-4,5-dihydro-oxazol-2-ylamine;
- (S)-4-{2-[1-(3-chloro-4-fluoro-phenyl)-cyclopropyl]-ethyl}-4,5-dihydro-oxazol-2-ylamine;
- (S)-4-{2-[1-(3,4-difluoro-phenyl)-cyclopropyl]-ethyl}-4,5-dihydro-oxazol-2-ylamine;
- (S)-4-{2-[1-(4-chloro-phenyl)-cyclobutyl]-ethyl}-4,5-dihydro-oxazol-2-ylamine;
- (S)-4-{2-[1(3,5-difluoro-phenyl)-cyclopropyl]-ethyl}-4,5-dihydro-oxazol-2-ylamine;
- (S)-4-{2-[1-(3-chloro-5-fluoro-phenyl)-cyclopropyl]-ethyl}-4,5-dihydro-oxazol-2-ylamine; and
- (S)-4-{2-[1-(4-bromo-phenyl)-cyclopropyl]-ethyl}-4,5-dihydro-oxazol-2-ylamine.

11. The compound of claim 1, selected from the group consisting of
- (S)-4-{2-[(3-chloro-phenyl)-dimethyl-silanyl]-ethyl}-4,5-dihydro-oxazol-2-ylamine; and
- (S)-4-{2-[(4-chloro-phenyl)-dimethyl-silanyl]-ethyl}-4,5-dihydro-oxazol-2-ylamine.

12. A pharmaceutical composition comprising a therapeutically effective amount of a compound selected from the group consisting of
- (S)-4-[2-(4-benzyl-phenoxy)-ethyl]-4,5-dihydro-oxazol-2-ylamine;
- (S)-4-[2-(4'-fluoro-biphenyl-4-yloxy)-ethyl]-4,5-dihydro-oxazol-2-ylamine;
- (S)-4-[2-(4-chloro-3-fluoro-phenoxy)-ethyl]-4,5-dihydro-oxazol-2-ylamine;
- (S)-4-[2-(4-bromo-phenoxy)-ethyl]-4,5-dihydro-oxazol-2-ylamine;
- (S)-4-[2-(3,4-dichloro-phenoxy)-ethyl]-4,5-dihydro-oxazol-2-ylamine;
- (S)-4-[2-(4-chloro-2-fluoro-phenoxy)-ethyl]-4,5-dihydro-oxazol-2-ylamine;
- (S)-4-[2-(4-methoxy-phenoxy)-ethyl]-4,5-dihydro-oxazol-2-ylamine;
- (S)-4-[2-(4-trifluoromethyl-phenoxy)-ethyl]-4,5-dihydro-oxazol-2-ylamine;
- 3-[2-((S)-2-amino-4,5-dihydro-oxazol-4-yl)-ethoxy]-benzonitrile;
- 3-[2-((S)-2-amino-4,5-dihydro-oxazol-4-yl)-ethoxy]-benzoic acid methyl ester;
- (S)-4-[2-(3,5-difluoro-phenoxy)-ethyl]-4,5-dihydro-oxazol-2-ylamine;
- 3-[2-((S)-2-amino-4,5-dihydro-oxazol-4-yl)-ethoxy]-benzoic acid benzyl ester;
- (S)-4-[(S)-2-(4-chloro-phenoxy)-propyl]-4,5-dihydro-oxazol-2-ylamine;
- (S)-4-[(S)-2-(4-fluoro-phenoxy)-propyl]-4,5-dihydro-oxazol-2-ylamine;
- (S)-4-[(S)-2-(3-chloro-phenoxy)-propyl]-4,5-dihydro-oxazol-2-ylamine;
- (S)-4-[(S)-2-(3,4-difluoro-phenoxy)-propyl]-4,5-dihydro-oxazol-2-ylamine;
- (S)-4-[(S)-2-(4-chloro-3-fluoro-phenoxy)-propyl]-4,5-dihydro-oxazol-2-ylamine;
- (S)-4-[(S)-2-(4-bromo-phenoxy)-propyl]-4,5-dihydro-oxazol-2-ylamine;
- (S)-4-[(S)-2-(3-chloro-4-fluoro-phenoxy)-propyl]-4,5-dihydro-oxazol-2-ylamine;
- (S)-4-[(S)-2-(4-chloro-2-fluoro-phenoxy)-propyl]-4,5-dihydro-oxazol-2-ylamine;
- (S)-4-[(S)-2-(2,4-difluoro-phenoxy)-propyl]-4,5-dihydro-oxazol-2-ylamine;
- (S)-4-[(S)-2-(3,4-dichloro-phenoxy)-propyl]-4,5-dihydro-oxazol-2-ylamine;
- 3-[(S)-2-(S)-2-amino-4,5-dihydro-oxazol-4-yl)-1-methyl-ethoxy]-benzonitrile;
- (S)-4-[(S)-2-(4-phenoxy-phenoxy)-propyl]-4,5-dihydro-oxazol-2-ylamine;
- (S)-4-(S)-2-phenoxy-propyl)-4,5-dihydro-oxazol-2-ylamine;
- (S)-4-[(R)-2-(3-chloro-phenoxy)-propyl]-4,5-dihydro-oxazol-2-ylamine;
- (S)-4-[(R)-2-(3-chloro-4-fluoro-phenoxy)-propyl]-4,5-dihydro-oxazol-2-ylamine;
- (S)-4-[(R)-2-(3,4-dichloro-phenoxy)-propyl]-4,5-dihydro-oxazol-2-ylamine;
- (S)-4-[(S)-2-(4-chloro-phenoxy)-butyl]-4,5-dihydro-oxazol-2-ylamine;
- (S)-4-(S)-2-phenoxy-butyl)-4,5-dihydro-oxazol-2-ylamine;
- (S)-4-[(S)-2-(4-bromo-phenoxy)-butyl]-4,5-dihydro-oxazol-2-ylamine;
- (S)-4-[(S)-2-(3-chloro-phenoxy)-butyl]-4,5-dihydro-oxazol-2-ylamine;
- (S)-4-[(S)-2-(4-chloro-3-fluoro-phenoxy)-butyl]-4,5-dihydro-oxazol-2-ylamine;
- (S)-4-[(S)-2-(2,4-difluoro-phenoxy)-butyl]-4,5-dihydro-oxazol-2-ylamine;
- (S)-4-[(S)-2-(4-fluoro-phenoxy)-butyl]-4,5-dihydro-oxazol-2-ylamine;
- (S)-4-[(S)-2-(3,4-difluoro-phenoxy)-butyl]-4,5-dihydro-oxazol-2-ylamine;
- (S)-4-[(S)-2-(3-chloro-4-fluoro-phenoxy)-butyl]-4,5-dihydro-oxazol-2-ylamine;
- (S)-4-[(S)-2-(4-trifluoromethyl-phenoxy)-butyl]-4,5-dihydro-oxazol-2-ylamine;
- (S)-4-[(S)-2-(3,4-dichloro-phenoxy)-butyl]-4,5-dihydro-oxazol-2-ylamine;
- (S)-4-[(S)-2-(4-chloro-2-fluoro-phenoxy)-butyl]-4,5-dihydro-oxazol-2-ylamine;
- (S)-4-[(S)-2-(3-benzyloxy-phenoxy)-butyl]-4,5-dihydro-oxazol-2-ylamine;
- 3-[(S)-1-(S)-2-amino-4,5-dihydro-oxazol-4-ylmethyl)-propoxy]-phenol;
- (S)-4-[(S)-2-(2,4,5-trifluoro-phenoxy)-butyl]-4,5-dihydro-oxazol-2-ylamine;
- (S)-4-[(S)-2-(naphthalen-2-yloxy)-butyl]-4,5-dihydro-oxazol-2-ylamine;
- (S)-4-[(S)-2-(2,4-dichloro-phenoxy)-butyl]-4,5-dihydro-oxazol-2-ylamine;
- (S)-4-[(S)-3-(4-fluoro-phenyl)-butyl]-4,5-dihydro-oxazol-2-ylamine;
- (S)-4-[(R)-3-(4-fluoro-phenyl)-butyl]-4,5-dihydro-oxazol-2-ylamine;
- (4S)-4-[3-(3,5-difluoro-phenyl)-pentyl]-4,5-dihydro-oxazol-2-ylamine;
- (S)-4-[(S)-1-(4-fluoro-phenyl)-ethoxymethyl]-4,5-dihydro-oxazol-2-ylamine;
- (S)-4-((S)-1-phenyl-propoxymethyl)-4,5-dihydro-oxazol-2-ylamine;

(S)-4-{2-[1-(4-fluoro-phenyl)-cyclopropyl]-ethyl}-4,5-dihydro-oxazol-2-ylamine;
(S)-4-{2-[1-(2,4-difluoro-phenyl)-cyclopropyl]-ethyl}-4,5-dihydro-oxazol-2-ylamine;
(S)-4-{2-[1-(3-chloro-4-fluoro-phenyl)-cyclopropyl]-ethyl}-4,5-dihydro-oxazol-2-ylamine;
(S)-4-{2-[1-(3,4-difluoro-phenyl)-cyclopropyl]-ethyl}-4,5-dihydro-oxazol-2-ylamine;
(S)-4-{2-[1-(4-chloro-phenyl)-cyclobutyl]-ethyl}-4,5-dihydro-oxazol-2-ylamine;
(S)-4-{2-[1-(3,5-difluoro-phenyl)-cyclopropyl]-ethyl}-4,5-dihydro-oxazol-2-ylamine;
(S)-4-{2-[1-(3-chloro-5-fluoro-phenyl)-cyclopropyl]-ethyl}-4,5-dihydro-oxazol-2-ylamine;
(S)-4-{2-[1-(4-bromo-phenyl)-cyclopropyl]-ethyl}-4,5-dihydro-oxazol-2-ylamine;
(S)-4-{2-[(3-chloro-phenyl)-dimethyl-silanyl]-ethyl}-4,5-dihydro-oxazol-2-ylamine; and
(S)-4-{2-[(4-chloro-phenyl)-dimethyl-silanyl]-ethyl}-4,5-dihydro-oxazol-2-ylamine.

13. The composition of claim 12, wherein the compound is selected from the group consisting of
(S)-4-[2-(4-benzyl-phenoxy)-ethyl]-4,5-dihydro-oxazol-2-ylamine;
(S)-4-[2-(4'-fluoro-biphenyl-4-yloxy)-ethyl]-4,5-dihydro-oxazol-2-ylamine;
(S)-4-[2-(4-chloro-3-fluoro-phenoxy)-ethyl]-4,5-dihydro-oxazol-2-ylamine;
(S)-4-[2-(4-bromo-phenoxy)-ethyl]-4,5-dihydro-oxazol-2-ylamine;
(S)-4-[2-(3,4-dichloro-phenoxy)-ethyl]-4,5-dihydro-oxazol-2-ylamine; and
(S)-4-[2-(4-chloro-2-fluoro-phenoxy)-ethyl]-4,5-dihydro-oxazol-2-ylamine.

14. The composition of claim 12, wherein the compound is selected from the group consisting of
(S)-4-[2-(4-methoxy-phenoxy)-ethyl]-4,5-dihydro-oxazol-2-ylamine;
(S)-4-[2-(4-trifluoromethyl-phenoxy)-ethyl]-4,5-dihydro-oxazol-2-ylamine;
3-[2-((S)-2-amino-4,5-dihydro-oxazol-4-yl)-ethoxy]-benzonitrile;
3-[2-((S)-2-amino-4,5-dihydro-oxazol-4-yl)-ethoxy]-benzoic acid methyl ester;
(S)-4-[2-(3,5-difluoro-phenoxy)-ethyl]-4,5-dihydro-oxazol-2-ylamine; and
3-[2-((S)-2-amino-4,5-dihydro-oxazol-4-yl)-ethoxy]-benzoic acid benzyl ester.

15. The composition of claim 12, wherein the compound is selected from the group consisting of
(S)-4-[(S)-2-(4-chloro-phenoxy)-propyl]-4,5-dihydro-oxazol-2-ylamine;
(S)-4-[(S)-2-(4-fluoro-phenoxy)-propyl]-4,5-dihydro-oxazol-2-ylamine;
(S)-4-[(S)-2-(3-chloro-phenoxy)-propyl]-4,5-dihydro-oxazol-2-ylamine;
(S)-4-[(S)-2-(3,4-difluoro-phenoxy)-propyl]-4,5-dihydro-oxazol-2-ylamine;
(S)-4-[(S)-2-(4-chloro-3-fluoro-phenoxy)-propyl]-4,5-dihydro-oxazol-2-ylamine;
(S)-4-[(S)-2-(4-bromo-phenoxy)-propyl]-4,5-dihydro-oxazol-2-ylamine;
(S)-4-[(S)-2-(3-chloro-4-fluoro-phenoxy)-propyl]-4,5-dihydro-oxazol-2-ylamine; and
(S)-4-[(S)-2-(4-chloro-2-fluoro-phenoxy)-propyl]-4,5-dihydro-oxazol-2-ylamine.

16. The composition of claim 12, wherein the compound is selected from the group consisting of
(S)-4-[(S)-2-(2,4-difluoro-phenoxy)-propyl]-4,5-dihydro-oxazol-2-ylamine;
(S)-4-[(S)-2-(3,4-dichloro-phenoxy)-propyl]-4,5-dihydro-oxazol-2-ylamine;
3-[(S)-2-((S)-2-amino-4,5-dihydro-oxazol-4-yl)-1-methyl-ethoxy]-benzonitrile;
(S)-4-[(S)-2-(4-phenoxy-phenoxy)-propyl]-4,5-dihydro-oxazol-2-ylamine;
(S)-4-((S)-2-phenoxy-propyl)-4,5-dihydro-oxazol-2-ylamine;
(S)-4-[(R)-2-(3-chloro-phenoxy)-propyl]-4,5-dihydro-oxazol-2-ylamine;
(S)-4-[(R)-2-(3-chloro-4-fluoro-phenoxy)-propyl]-4,5-dihydro-oxazol-2-ylamine; and
(S)-4-[(R)-2-(3,4-dichloro-phenoxy)-propyl]-4,5-dihydro-oxazol-2-ylamine.

17. The composition of claim 12, wherein the compound is selected from the group consisting of
(S)-4-[(S)-2-(4-chloro-phenoxy)-butyl]-4,5-dihydro-oxazol-2-ylamine;
(S)-4-(S)-2-phenoxy-butyl)-4,5-dihydro-oxazol-2-ylamine;
(S)-4-[(S)-2-(4-bromo-phenoxy)-butyl]-4,5-dihydro-oxazol-2-ylamine;
(S)-4-[(S)-2-(3-chloro-phenoxy)-butyl]-4,5-dihydro-oxazol-2-ylamine;
(S)-4-[(S)-2-(4-chloro-3-fluoro-phenoxy)-butyl]-4,5-dihydro-oxazol-2-ylamine;
(S)-4-[(S)-2-(2,4-difluoro-phenoxy)-butyl]-4,5-dihydro-oxazol-2-ylamine;
(S)-4-[(S)-2-(4-fluoro-phenoxy)-butyl]-4,5-dihydro-oxazol-2-ylamine;
(S)-4-[(S)-2-(3,4-difluoro-phenoxy)-butyl]-4,5-dihydro-oxazol-2-ylamine; and
(S)-4-[(S)-2-(3-chloro-4-fluoro-phenoxy)-butyl]-4,5-dihydro-oxazol-2-ylamine.

18. The composition of claim 12, wherein the compound is selected from the group consisting of
(S)-4-[(S)-2-(4-trifluoromethyl-phenoxy)-butyl]-4,5-dihydro-oxazol-2-ylamine;
(S)-4-[(S)-2-(3,4-dichloro-phenoxy)-butyl]-4,5-dihydro-oxazol-2-ylamine;
(S)-4-[(S)-2-(4-chloro-2-fluoro-phenoxy)-butyl]-4,5-dihydro-oxazol-2-ylamine;
(S)-4-[(S)-2-(3-benzyloxy-phenoxy)-butyl]-4,5-dihydro-oxazol-2-ylamine;
3-[(S)-1-(S)-2-amino-4,5-dihydro-oxazol-4-ylmethyl)-propoxy]-phenol;
(S)-4-[(S)-2-(2,4,5-trifluoro-phenoxy)-butyl]-4,5-dihydro-oxazol-2-ylamine;
(S)-4-[(S)-2-(naphthalen-2-yloxy)-butyl]-4,5-dihydro-oxazol-2-ylamine; and
(S)-4-[(S)-2-(2,4-dichloro-phenoxy)-butyl]-4,5-dihydro-oxazol-2-ylamine.

19. The composition of claim 12, wherein the compound is selected from the group consisting of
(S)-4-[(S)-3-(4-fluoro-phenyl)-butyl]-4,5-dihydro-oxazol-2-ylamine;
(S)-4-[(R)-3-(4-fluoro-phenyl)-butyl]-4,5-dihydro-oxazol-2-ylamine; and
(4S)-4-[3-(3,5-difluoro-phenyl)-pentyl]-4,5-dihydro-oxazol-2-ylamine.

20. The composition of claim 12, wherein the compound is selected from the group consisting of
- (S)-4-[(S)-1-(4-fluoro-phenyl)-ethoxymethyl]-4,5-dihydro-oxazol-2-ylamine; and
- (S)-4-((S)-1-phenyl-propoxymethyl)-4,5-dihydro-oxazol-2-ylamine.

21. The composition of claim 12, wherein the compound is selected from the group consisting of
- (S)-4-{2-[1-(4-fluoro-phenyl)-cyclopropyl]-ethyl}-4,5-dihydro-oxazol-2-ylamine;
- (S)-4-{2-[1-(2,4-difluoro-phenyl)-cyclopropyl]-ethyl}-4,5-dihydro-oxazol-2-ylamine;
- (S)-4-{2-[1-(3-chloro-4-fluoro-phenyl)-cyclopropyl]-ethyl}-4,5-dihydro-oxazol-2-ylamine;
- (S)-4-{2-[1-(3,4-difluoro-phenyl)-cyclopropyl]-ethyl}-4,5-dihydro-oxazol-2-ylamine;
- (S)-4-{2-[1-(4-chloro-phenyl)-cyclobutyl]-ethyl}-4,5-dihydro-oxazol-2-ylamine;
- (S)-4-{2-[1(3,5-difluoro-phenyl)-cyclopropyl]-ethyl}-4,5-dihydro-oxazol-2-ylamine;
- (S)-4-{2-[1-(3-chloro-5-fluoro-phenyl)-cyclopropyl]-ethyl}-4,5-dihydro-oxazol-2-ylamine; and
- (S)-4-{2-[1-(4-bromo-phenyl)-cyclopropyl]-ethyl}-4,5-dihydro-oxazol-2-ylamine.

22. The composition of claim 12, wherein the compound is selected from the group consisting of
- (S)-4-{2-[(3-chloro-phenyl)-dimethyl-silanyl]-ethyl}-4,5-dihydro-oxazol-2-ylamine; and
- (S)-4-{2-[(4-chloro-phenyl)-dimethyl-silanyl]-ethyl}-4,5-dihydro-oxazol-2-ylamine.

* * * * *